US008674075B2

(12) United States Patent
Zheng et al.

(10) Patent No.: US 8,674,075 B2
(45) Date of Patent: Mar. 18, 2014

(54) CHIMERIC PEPTIDES FOR THE REGULATION OF GTPASES

(75) Inventors: Yi Zheng, Cincinnati, OH (US); David A. Williams, Cincinnati, OH (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/584,745

(22) Filed: Aug. 13, 2012

(65) Prior Publication Data

US 2012/0329725 A1    Dec. 27, 2012

Related U.S. Application Data

(63) Continuation of application No. 13/036,964, filed on Feb. 28, 2011, now Pat. No. 8,242,246, which is a continuation of application No. 12/348,762, filed on Jan. 5, 2009, now Pat. No. 7,915,384, which is a continuation of application No. 10/918,648, filed on Aug. 12, 2004, now abandoned.

(60) Provisional application No. 60/494,719, filed on Aug. 13, 2003.

(51) Int. Cl.
*C07K 14/00* (2006.01)
*A61K 38/00* (2006.01)

(52) U.S. Cl.
USPC .......................................... 530/350; 514/1.1

(58) Field of Classification Search
None
See application file for complete search history.

(56) References Cited

U.S. PATENT DOCUMENTS

| | | | |
|---|---|---|---|
| 4,997,834 | A | 3/1991 | Muro et al. |
| 5,492,898 | A | 2/1996 | Bertics et al. |
| 6,117,850 | A | 9/2000 | Patchen et al. |
| 6,451,825 | B1 | 9/2002 | Uehata et al. |
| 6,620,591 | B1 | 9/2003 | Dunlay et al. |
| 6,642,263 | B2 | 11/2003 | Sun et al. |

FOREIGN PATENT DOCUMENTS

| | | |
|---|---|---|
| CA | 2467557 | 5/2003 |
| WO | WO 97/30992 | 8/1997 |
| WO | WO 99/40783 | 8/1999 |
| WO | WO 01/78761 | 10/2001 |
| WO | WO 01/83745 | 11/2001 |
| WO | WO 01/93900 | 12/2001 |
| WO | WO 01/97608 | 12/2001 |
| WO | WO 03/011277 | 2/2003 |
| WO | WO 03/042239 | 5/2003 |
| WO | WO 2004/091654 | 10/2004 |
| WO | WO 2005/017160 | 2/2005 |
| WO | WO 2005/056024 | 6/2005 |

OTHER PUBLICATIONS

Abo et al., Activation of the NADPH oxidase involves the small GTP-binding protein p21rac1., Nature, 1991, vol. 353, Issue 6345, pp. 668-670.
Allen, W.E. et al., A role for Cdc42 in macrophage chemotaxis., J Cell Biol, 1998, vol. 141, Issue 5, pp. 1147-1157.
Benard et al., Characterization of Rac and Cdc42 Activation in Chemoattractant-stimulated Human Neutrophils Using a Novel Assay for Active GTPases, J. Biol. Chem, 1999. vol. 274, Issue 19, pp. 13198-13204.
Chieregatti et al., Myr 7 is a novel myosin IX-RhoGAP expressed in rat brain, Journal of Cell Science, 1998, vol. 111, pp. 3597-3608.
Croker et al., The Rac2 guanosine triphosphatase regulates B lymphocyte antigen receptor responses and chemotaxis and is required for establishment of B-1a and marginal zone B lymphocytes., J. Immunol., Apr. 2002, vol. 168, issue 7, pp. 3376-3386.
Del Pozo et al., Integrins regulate GTP-Rac localized effector interactions through dissociation of Rho-GDI., Nat Cell Biol, Mar. 2002, vol. 4, Issue 3, pp. 232-239.
Diekmann et al., Rac GTPase interacts with GAPs and target proteins through multiple effector sites., EMBO J., Nov. 1995, vol. 14, Issue 21, pp. 5297-5305.
EP Office Action dated May 14, 2007 for European Patent Application No. 04781185.6.
Etienne-Manneville et al., Rho GTPases in cell biology., Nature, 2002, vol. 420, Issue 6919, pp. 629-635.
File History of U.S. Appl. No. 10/918,328, as of Jun. 21, 2007.
File History of U.S. Appl. No. 10/918,328, for the period of Jun. 22, 2007-Sep. 18, 2007.
File History of U.S. Appl. No. 11/003,935, as of Jun. 21, 2007.
File History of U.S. Appl. No. 11/003,935, for the period of Jun. 22, 2007-Sep. 18, 2007.
Fritz et al., Rho GTPases in human breast tumours: expression and mutation analyses and correlation with clinical parameters, British Journal of Cancer, 2002, vol. 87, pp. 635-644.
Gao Yuan et al., Rational design and characterization of a Rac GTPase-specific small molecule inhibitor, Proceedings of the National Academy of Sciences of the United States of America, May 18, 2004, vol. 101, Issue 20, pp. 7618-7623.

(Continued)

*Primary Examiner* — Suzanne M Noakes
*Assistant Examiner* — Jae W Lee
(74) *Attorney, Agent, or Firm* — Fish & Richardson P.C.

(57) ABSTRACT

Chimeric peptides or fusion proteins are disclosed that include a RhoGAP activity domain and at least one specificity domain that targets a specific Rho protein. The fusion proteins can be used to inhibit any GTPase activity within a cell. The fusion proteins are particularly advantageous for the treatment of cancer. The present invention generally relates to chimeric peptides capable of regulating GTPases, and more particularly, to methods of targeting individual GTPases by using GTPase-activating proteins. Such proteins may be used for the treatment of cancers and other GTPase-related diseases. This invention relates to nucleic acid molecules and the encoded GTPase activating proteins, and variants thereof, and to the use of these molecules in the characterization, diagnosis, prevention, and treatment of cell signaling, immune, and cell proliferative disorders, particularly cancer. Disclosed herein are compounds and methods for regulating transcription of a selected gene.

17 Claims, 3 Drawing Sheets

(56) References Cited

OTHER PUBLICATIONS

Gottig et al., Role of the monomeric GTPase Rho in hernatopoietic progenitor cell migration and transplantation, Eur. J. Immunol, 2006, vol. 36, pp. 180-189.
Gu et al., Deletion of a DNA polymerase beta gene segment in T cells using cell type-specific gene targeting., Science, Jul. 1994, vol. 265, Issue 5168, pp. 103-106.
Gu Yi et al., Hematopoietic cell regulation by Rac1 and Rac2 guanosine triphosphates, Science, 2003, vol. 302, Issue 5644, pp. 445-449.
Gu, Y. et al., Rac2, a hematopoiesis-specific Rho GTPase, specifically regulates mast cell protease gene expression in bone marrow-derived mast cells, Mollecular and Cellular Biology, Nov. 2002, vol. 22, Issue 21, pp. 7645-7657.
Gu, Y. et al., RhoH, a hematopoietic-specific Rho GTPase, regulates proliferation, survival, migration and engraftment of hematopoietic progenitor cells, Hematopoiesis, Feb. 2005, vol. 105, Issue 4, pp. 1467-1475.
Hakoshima, T. et al., Structural Basis of the Rho GTPase signaling, J. Biochem., 2003, vol. 134,, pp. 327-331.
Hall, Rho GTPases and the actin cytoskeleton., Science, Jan. 1998, vol. 279, Issue 5350, pp. 509-514.
Henschler et al., SDF-1 alpha—induced intracellular calcium transient involves Rho GTPase signalling and is required for migration of hematopoietic progenitor cells, Bioch. and Biophys. Res. Com., 2003, vol. 311, pp. 1067-1071.
Innocenti et al., Phosphoinositide 3-kinase activates Rac by entering in a complex with Eps8, Abi1, and Sos-1., J Cell Biol, Jan. 2003, vol. 160, Issue 1, pp. 17-23.
International Search Report dated Feb. 2, 2005 for PCT Application No. PCT/US2004/026493.
Judkins et al., Single nucleotide polymorphisms in clinical genetic testing: the characterization of the clinical significance of genetic variants and their application in clinical research fro BRCA1, Mutation Research. 2005, vol. 573, pp. 168-179.
Kennedy et al., The PI 3-kinase/Akt signaling pathway delivers an anti-apoptotic signal., Genes Dev, Mar. 1997, vol. 11, Issue 6, pp. 701-713.
Kisselev, Structure, 2002, vol. 10, pp. 8-9.
Knaus et al., Regulation of phagocyte oxygen radical production by the GTP-binding protein Rac 2., Science, Dec. 1991, vol. 254, Issue 5037, pp. 1512-1515.
Li et al., Role of the guanosine triphosphatase Rac2 in T helper 1 cell differentiation., Science, Jun. 2000, vol. 288, Issue 5474, pp. 2219-2222.
Li, X. et al., The hematopoiesis-specific GTP-binding protein RhoH is GTPase deficient and modulates activities of other Rho GTPases by an inhibitory function., Molecular and Cellular Biology, Feb. 2002, vol. 22, Issue 4, pp. 1158-1171.
Llevadot, J. et al., HMG-CoA reductase inhibitor mobilizes bone marrow-derived endothelial progenitor cells, J. Clin. Investig., Aug. 2001, vol. 108, Issue 3, pp. 399-405.
MeSH results for "bcr", Retrieved from the Internet <URL: http://www.ncbi.nlm.nih.gov/sites/entrez>, searched on Sep. 23, 2008.
MeSH results for "p190", Tretrieved from the Internet <URL: http://www.ncbi.nlm.nih.gov/sites/entrez>, searched on Sep. 23, 2008.
Michaelson et al., Differential localization of Rho GTPases in live cells: regulation by hypervariable regions and RhoGDI binding, Journal of Cell Biology, Jan. 2001, vol. 152, Issue 1, pp. 11-126.
Minden et al., Differential activation of ERK and JNK mitogen-activated protein kinases by Raf-1 and MEKK., Science, Dec. 1994, vol. 266, Issue 5191, pp. 1719-1732.
Moebest et al., Blood, Nov. 2000, vol. 96, Issue 11, part 1, pp. 687a.
Moll et al., The murine rac1 gene: cDNA cloning, tissue distribution and regulated expression of rac1 mRNA by disassembly of actin microfilaments., Oncogene, May 1991, vol. 6, Issue 5, pp. 863-866.
Moon et al., Rho GTPase-activating proteins in cell regulation, Trends in Cell Biology, Jan. 2003, vol. 13, Issue 1, pp. 13-22.
Narumiya et al., rho gene products, botulinum C3 exoenzyme and cell adhesion, Cell. Signal., 1993, vol. 5, Issue 1, pp. 9-19.
Ngo et al., The Protein Folding Problem and Teritary Structure Prediction 1994, pp. 433 and 492-495.
Nobes et al., Rho, rac, and cdc42 GTPases regulate the assembly of multimolecular focal complexes associated with actin stress fibers, lamellipodia, and filopodia., Cell, Apr. 1995, vol. 81, Issue 1, pp. 53-62.
Olson et al., An essential role for Rho, Rac, and Cdc42 GTPases in cell cycle progression through G1., Science, Sep. 1995, vol. 269, Issue 5228, pp. 1270-1272.
Palacios et al., Long-term culture of lymphohematopoietic stem cells., Proc Natl Acad Sci U S A, May 1996, vol. 93, Issue 11, pp. 5247-5252.
Papayannopoulou et al., Homing and trafficking of hemopoietic progenitor cells., Acta Haematol, 1997, vol. 97, Issue 1-2, pp. 97-104.
Ridely et al., The small GTP-binding protein rac regulates growth factor-induced membrande ruffling., Cell, 1992, vol. 70, Issue 3, pp. 401-410.
Roberts et al., Deficiency of the hematopoietic cell-specific Rho family GTPase Rac2 is characterized by abnormalities in neutrophil function and host defense., Immunity, Feb. 1999, vol. 10, Issue 2, pp. 183-196.
Sahai et al., Rho-GTPases and Cancer, Cancer, Feb. 2002, vol. 2, Issue 2, pp. 133-142.
Sekine et al., Asparagine residue in the rho gene product is the modification site for botulinum ADP-ribosyltransferase., J. Biol. Chem., 1989, vol. 264, pp. 8602-8605.
Sherr et al., Inhibitors of mammalian G1 cyclin-dependent kinases., Genes Dev., May 1995, vol. 9, Issue 10, pp. 1149-1163.
Shirsat et al., A member of the ras gene superfamily is expressed specifically in T, B and myeloid hemopoietic cells., Oncogene, May 1990, vol. 5, Issue 5, pp. 769-772.
Somlyo, Signal transduction: Rhomantic interludes raise blood pressure, Nature, 1997, vol. 389, pp. 908-910.
Srinivasan et al., Rac and Cdc42 play distinct roles in regulating PI(3,4,5)P3 and polarity during neutrophil chemotaxis., J. Cell Biol, Feb. 2003, vol. 160, Issue 3, pp. 375-385.
Tao et al., The TRQQRP motif licated near the C-terminus of Rac2 is essential for Rac2 biologic functions and intracellular localization, Blood, Sep. 2002, vol. 100, Issue 5, pp. 1686-1687.
U.S. National Library of Medicine's controlled vocabulary database used for indexing articles fro MEDLINE/PubMed, Retrieved from the Internet <URL: http://www.ncbi.nlm.nih.gov/sites/entrez?db=mesh>, searched on Jun. 13, 2007.
Uehata et al., Calcium sensitization of smooth muscle mediated by a Rho-associated protein kinase in hypertension, Nature, 1997, vol. 389, pp. 990-994.
Van Aelst et al., Rho GTPasesa and signaling networks., Genes Dev., Sep. 1997, vol. 11, Issue 18, pp. 2295-2322.
Vojtek et al., Rho family members: Activators of MAP kinase cascades, Cell, 1995, vol. 82, pp. 527-52.
Wang et al., A novel strategy for specifically down-regulating individual Rho GTPase activity in tumor cells, Journal of Biological Chemistry, Nov. 2003, vol. 278, Issue 45, pp. 44617-44625.
Wang et al., The GTPase and Rho GAP Domains of p190, a Tumor Suppressor Protein That Binds the Mr 120,000 Ras GAP, Independently Function as Anti-Ras Tumor Suppressors, Cancer Research, 1997, vol. 57, pp. 2478-2484.
Wennerberg et al., Rho-family GTPases: It's not only Rac and Rho (and I like it), Journal of Cell Science, Mar. 2004, vol. 117, Issue 8, pp. 1301-1312.
Williams et al., Dominant negative mutation of the hematopoietic-specific Rho GTPase, Rac2, is associated with a human phagocyte immunodeficiency., Blood, Sep. 2000, vol. 96, Issue 5, pp. 1646-1654.
Wishart et al., A Single Mutation Converts a Novel Phosphosyrosine Binding Domain into a Dual-specificity Phosphatase, Journal of Biological Chemistry, 1995, vol. 270, Issue 45, pp. 26782-26785.
Witkowski et al., Conversion of a beta-ketoacyl synthase to a malonyl decarboxylase by replacement of the active-site cysteine with glutamine., Biochemistry, 1999, vol. 38, Issue 36, pp. 11643-11650.

(56) References Cited

OTHER PUBLICATIONS

Yang et al., Rac and Cdc42 GTPases control hematopoietic stem cell shape adhesion, migration, and mobilization., Proc Natl Acad Sci U S A, May 2001, vol. 98, Issue 10, pp. 5614-5618.

Yang et al., Rac2 stimulates Akt activation affecting BAD/Bcl-XL expression while mediating survival and actin function in primary mast cells., Immunity, May 2000, vol. 12, Issue 5, pp. 557-568.

Zhang et al., Regulation of RhoA GTP hydrolysis by the GTPase-activating proteins p190, p50RhoGAP, Bcr, and 3BP-1, Biochemistry, 1998, vol. 37, Issue 15, pp. 5249-5257.

SEQUENCE LISTING

```
<160> NUMBER OF SEQ ID NOS: 28

<210> SEQ ID NO 1
<211> LENGTH: 4542
<212> TYPE: DNA
<213> ORGANISM: Rattus sp.

<400> SEQUENCE: 1
atgatgatgg caagaaagca agatgtccga atccccacct acaacatcag tgtggtggga      60
ttgtccggca ctgagaagga gaaaggccag tgcggcattg ggaagtcttg tctatgtaac     120
cgctttgtgc gcccaagtgc tgatgagttt cacctggacc acacttctgt cctcagcacc     180
agtgactttg gtgggcgggt ggtcaataat gaccatttc tgtactgggg agaagttagc      240
cgctccctgg aggactgtgt ggaatgtaag atgcacattg tggagcagac tgagtttatt     300
gacgatcaga cttttcaacc tcatcgaagc acggcactgc agccctacat caagagagcc     360
gcagccacca agcttgcttc agctgaaaaa ctcatgtatt tttgcactga ccagctaggg     420
ctggagcaag actttgagca gaaacagatg ccagatggga agctgctggt tgacggtttc     480
```

```
cttctgggca tcgatgttag caggggcatg aacaggaact tcgatgacca gctcaagttt    540
gtctccaatc tctacaatca gcttgcaaaa acaaaaaagc ccatagtaat agtcctgacc    600
aagtgtgatg agggtgttga gcggtacatt agagatgcac atacttttgc cttaagcaaa    660
aagaacctcc aggttgtaga gacctctgca aggtccaatg tgaatgtgga cttggctttc    720
acgaccttag tgcaactcat tgataagagt cgagggaaga cgaaaatcat cccttacttt    780
gaagctctca agcagcagag tcagcagata gctacagcaa aggacaagta tgagtggttg    840
gtgagccgca ttgtgaaaag tcacaatgag aactggctga gtgtcagccg aaagatgcag    900
gcctcccctg agtaccagga ctatgtctat ctggaaggga cacagaaagc caagaagctc    960
ttcctgcagc acattcaccg cctcaagcat gagcatattg agcgccggag aaagctgtac   1020
ctggcagccc tgccattggc tttttgaagcc ctcataccta atctagatga agtagaccac   1080
ctgagctgca ttaaagcaaa aaagctgtta gagactaagc cagagttctt aaagtggttt   1140
gttgtacttg aagagacacc atgggatgaa accagccaca ttgacaacat ggaaaatgag   1200
cggattccct ttgacttgat ggatactgtc cctgctgagc agttgtatga cccacttg    1260
gagaagctga ggaatgagag gaagagagct gagatgcgaa gggctttcaa agaaaacctg   1320
gagacctctc ctttcataac tcctgggaaa ccttgggaag aagctcgtag ttttattatg   1380
aatgaagact tctaccagtg gctggaagaa tctgtgtaca tggacatcta tggcaagcac   1440
caaaagcaga ttatagaccg ggcaaaggaa gagttccaag agttgctttt ggagtattca   1500
gaattgtttt atgagctgga gctggatgct aaacccagta aggaaaagat gggtgttatc   1560
caggatgttc tgggtgaaga gcaacgattt aaagcattgc agaaactcca agcagagcgt   1620
gatgccctca ttctgaagca cattcatttt gtgtaccacc caacaaagga acatgccca    1680
agctgtccag cttgcgtaga tgctaagatt gaacatttga tcagttctcg ctttatccga   1740
ccatctgata ggaatcagaa gaactctttg tctgacccca atattgatag gatcaatttg   1800
gttattttag gcaaagatgg ccttgcccga gagttagcca atgaaattcg agctctttgt   1860
acaaatgatg acaagtatgt aatagatggt aaaatgtatg agctttctct gaggccaata   1920
gaggggaatg ttgccgttcc tgtgaactct ttccagacac caaccttcca accccatggc   1980
tgtctctgcc tttacaattc aaaggagtcg ctgtcctatg tggtggagag tatagagaag   2040
agcagagaat ctacactggg caggcgggat aatcacttag tccacctccc cttgacttta   2100
attttagtta acaagagagg ggacacaagt ggagagactc tgcacagctt aatacagcaa   2160
ggccagcaga ttgctagcaa acttcagtgt gtctttcttg atcctgcgtc tgctggcatt   2220
ggttatggac gcaacattaa cgagaagcag atcagtcaag ttctgaaggg actcctggac   2280
tctaagcgca acttaaacct ggttagttct actgctagta tcaaagattt ggctgatgtg   2340
gaccttcgaa ttgtcatgtg tctcatgtgt ggtgatcctt ttagtgcaga tgacattctc   2400
tctcctgtcc tgcagtccca aacttgtaaa tcttcccact gtgggagcag caactctgtt   2460
ttacttgaac ttccaattgg agtacacaag aagcgcattg agctgtctgt tctttcatac   2520
cattcctcat ttagcatccg aaagagccgg ttggttcatg gtacattgt ttttattca    2580
gccaaacgta aggcctcctt ggcaatgtta cgtgcctttc tttgtgaagt gcaggatatt   2640
atccccatcc agcttgtcgc actcactgat ggcgctatag atgtcctgga caatgactta   2700
agtcgagagc agctaacaga gggagaggaa attgcacaag aaattgatgg gagattcaca   2760
agcatccctt gtgccaccc ccagcataaa ctcgagctct ccatcccctt ttttaaagat    2820
gtggtggaga aaaagaacat aatcgaggcc acacacatgt acgataatgt ggctgaggcc   2880
```

```
tgcagcacca ctgaggaggt attcaactcc cccagggctg ggtcacccct ctgcaattca   2940
aacttacagg actcagaaga agatgtggag cctccatcgt accacctttt tcgggaagat   3000
gcgacattgc cctccctgtc caaagatcat tccaagttct caatgagct ggagggaaac    3060 gacgggctgt ctttcataat gagcaacttt gagagtaaac tgaacaacaa agtacctcca   3120
ccagtcaaac caaagcctcc tgtgcatttt gagatcacaa agatctttc ttacttagac    3180 caaggtcatc gggagggaca gaggaagtct atgtcttcta gccctggat gcctcaggat    3240 ggatttgatc cttctgacta cgcagagccc atggatgctg tggtcaagcc aaggaatgag   3300
gaagaaaaca tatactcagt gccccacgac agcacccagg gcaagatcat taccattcgg   3360
aacatcaaca agcccagtc caatggcagt ggcaatggtt ctgacagtga gatggacaca    3420
agctctctag agcgaggccg caaagtatct gcagtgagta gcctgtgct gtacaggacg    3480 agatgcaccc gcctggggcg gtttgctagt taccgcacca gcttcagtgt tgggagtgat   3540
gatgagctgg gacccatccg aaagaaagag gaggaccagg catcccaagg ttataaaggg   3600
gacaatgctg tcattcctta tgaaacagat gaggacccca ggaggaggaa tatccttcga   3660
agtctaagga ggaacaccaa gaaaccaaag cccaaacccc gaccatccat cacaaaggca   3720
acctgggaga gtaactattt tggggtgcct ttaacaacag tggtgactcc agagaagccg   3780
atacccattt tcattgaaag atgcattgag tacattgaag ccacaggact aagcacagaa   3840
ggcatctacc gggtcagcgg aaacaagtca gaaatggaaa gtttgcaaag acagtttgat   3900
caagatcaca atctggacct ggcagagaaa gacttcactg tgaacactgt ggcaggggcc   3960
atgaagagtt ttttctcgga gctaccagac ccctggtac atacagcat gcagattgac    4020 ttggtggaag ctcacaagat caacgacagg gagcagaagc tgcatgctct gaaggaagtg   4080
ctgaagaagt tccctaagga gaaccatgaa gtcttcaaat atgtcatctc ccacctgaac   4140
agagtcagcc acaacaacaa ggtgaatctt atgaccagtg agaacctgtc catctgcttc   4200
tggcccacgt tgatgcggcc tgacttcagc agcatggacg cactcacagc cactcgatcc   4260
taccagacca tcatcgagct cttcatccag cagtgcccct tcttcttcta caacggccg    4320 atcagtgagc caccggggc tgcgctggct cccccttcagc catggcaccc actgtcccct   4380
tcctcacctc tacacctgct accagtcagc catcacctcc ccagtcacct cctccaaccc   4440
ctcagtcccc aatgcagcca ttgctctcct ctcagctcca agccgaacac acgctgtgag   4500
ccaccacagc ccaggaagca ggaaaatcag ttgtcttctt ga                      4542
```

<210> SEQ ID NO 2
<211> LENGTH: 1513
<212> TYPE: PRT
<213> ORGANISM: Rattus sp.
<220> FEATURE:
<221> NAME/KEY: DOMAIN
<222> LOCATION: (1261)..(1431)
<223> OTHER INFORMATION: p190RhoGAP domain
<400> SEQUENCE: 2

```
Met Met Met Ala Arg Lys Gln Asp Val Arg Ile Pro Thr Tyr Asn Ile
1               5                   10                  15

Ser Val Val Gly Leu Ser Gly Thr Glu Lys Glu Lys Gly Gln Cys Gly
            20                  25                  30

Ile Gly Lys Ser Cys Leu Cys Asn Arg Phe Val Arg Pro Ser Ala Asp
        35                  40                  45

Glu Phe His Leu Asp His Thr Ser Val Leu Ser Thr Ser Asp Phe Gly
    50                  55                  60
```

-continued

```
Gly Arg Val Val Asn Asn Asp His Phe Leu Tyr Trp Gly Glu Val Ser
 65                  70                  75                  80

Arg Ser Leu Glu Asp Cys Val Glu Cys Lys Met His Ile Val Glu Gln
                 85                  90                  95

Thr Glu Phe Ile Asp Asp Gln Thr Phe Gln Pro His Arg Ser Thr Ala
            100                 105                 110

Leu Gln Pro Tyr Ile Lys Arg Ala Ala Thr Lys Leu Ala Ser Ala
        115                 120                 125

Glu Lys Leu Met Tyr Phe Cys Thr Asp Gln Leu Gly Leu Glu Gln Asp
    130                 135                 140

Phe Glu Gln Lys Gln Met Pro Asp Gly Lys Leu Leu Val Asp Gly Phe
145                 150                 155                 160

Leu Leu Gly Ile Asp Val Ser Arg Gly Met Asn Arg Asn Phe Asp Asp
                165                 170                 175

Gln Leu Lys Phe Val Ser Asn Leu Tyr Asn Gln Leu Ala Lys Thr Lys
            180                 185                 190

Lys Pro Ile Val Ile Val Leu Thr Lys Cys Asp Glu Gly Val Glu Arg
        195                 200                 205

Tyr Ile Arg Asp Ala His Thr Phe Ala Leu Ser Lys Lys Asn Leu Gln
    210                 215                 220

Val Val Glu Thr Ser Ala Arg Ser Asn Val Asn Val Asp Leu Ala Phe
225                 230                 235                 240

Thr Thr Leu Val Gln Leu Ile Asp Lys Ser Arg Gly Lys Thr Lys Ile
                245                 250                 255

Ile Pro Tyr Phe Glu Ala Leu Lys Gln Gln Ser Gln Gln Ile Ala Thr
            260                 265                 270

Ala Lys Asp Lys Tyr Glu Trp Leu Val Ser Arg Ile Val Lys Ser His
        275                 280                 285

Asn Glu Asn Trp Leu Ser Val Ser Arg Lys Met Gln Ala Ser Pro Glu
    290                 295                 300

Tyr Gln Asp Tyr Val Tyr Leu Glu Gly Thr Gln Lys Ala Lys Lys Leu
305                 310                 315                 320

Phe Leu Gln His Ile His Arg Leu Lys His Glu His Ile Glu Arg Arg
                325                 330                 335

Arg Lys Leu Tyr Leu Ala Ala Leu Pro Leu Ala Phe Glu Ala Leu Ile
            340                 345                 350

Pro Asn Leu Asp Glu Val Asp His Leu Ser Cys Ile Lys Ala Lys Lys
        355                 360                 365

Leu Leu Glu Thr Lys Pro Glu Phe Leu Lys Trp Phe Val Val Leu Glu
    370                 375                 380

Glu Thr Pro Trp Asp Glu Thr Ser His Ile Asp Asn Met Glu Asn Glu
385                 390                 395                 400

Arg Ile Pro Phe Asp Leu Met Asp Thr Val Pro Ala Glu Gln Leu Tyr
                405                 410                 415

Glu Thr His Leu Glu Lys Leu Arg Asn Glu Arg Lys Arg Ala Glu Met
            420                 425                 430

Arg Arg Ala Phe Lys Glu Asn Leu Glu Thr Ser Pro Phe Ile Thr Pro
        435                 440                 445

Gly Lys Pro Trp Glu Glu Ala Arg Ser Phe Ile Met Asn Glu Asp Phe
    450                 455                 460

Tyr Gln Trp Leu Glu Glu Ser Val Tyr Met Asp Ile Tyr Gly Lys His
465                 470                 475                 480

Gln Lys Gln Ile Ile Asp Arg Ala Lys Glu Glu Phe Gln Glu Leu Leu
```

```
                485                 490                 495
Leu Glu Tyr Ser Glu Leu Phe Tyr Glu Leu Glu Leu Asp Ala Lys Pro
            500                 505                 510

Ser Lys Glu Lys Met Gly Val Ile Gln Asp Val Leu Gly Glu Glu Gln
            515                 520                 525

Arg Phe Lys Ala Leu Gln Lys Leu Gln Ala Glu Arg Asp Ala Leu Ile
            530                 535                 540

Leu Lys His Ile His Phe Val Tyr His Pro Thr Lys Glu Thr Cys Pro
545                 550                 555                 560

Ser Cys Pro Ala Cys Val Asp Ala Lys Ile Glu His Leu Ile Ser Ser
                565                 570                 575

Arg Phe Ile Arg Pro Ser Asp Arg Asn Gln Lys Asn Ser Leu Ser Asp
            580                 585                 590

Pro Asn Ile Asp Arg Ile Asn Leu Val Ile Leu Gly Lys Asp Gly Leu
            595                 600                 605

Ala Arg Glu Leu Ala Asn Glu Ile Arg Ala Leu Cys Thr Asn Asp Asp
            610                 615                 620

Lys Tyr Val Ile Asp Gly Lys Met Tyr Glu Leu Ser Leu Arg Pro Ile
625                 630                 635                 640

Glu Gly Asn Val Ala Val Pro Val Asn Ser Phe Gln Thr Pro Thr Phe
                645                 650                 655

Gln Pro His Gly Cys Leu Cys Leu Tyr Asn Ser Lys Glu Ser Leu Ser
            660                 665                 670

Tyr Val Val Glu Ser Ile Glu Lys Ser Arg Glu Ser Thr Leu Gly Arg
            675                 680                 685

Arg Asp Asn His Leu Val His Leu Pro Leu Thr Leu Ile Leu Val Asn
690                 695                 700

Lys Arg Gly Asp Thr Ser Gly Glu Thr Leu His Ser Leu Ile Gln Gln
705                 710                 715                 720

Gly Gln Gln Ile Ala Ser Lys Leu Gln Cys Val Phe Leu Asp Pro Ala
                725                 730                 735

Ser Ala Gly Ile Gly Tyr Gly Arg Asn Ile Asn Glu Lys Gln Ile Ser
            740                 745                 750

Gln Val Leu Lys Gly Leu Leu Asp Ser Lys Arg Asn Leu Asn Leu Val
            755                 760                 765

Ser Ser Thr Ala Ser Ile Lys Asp Leu Ala Asp Val Asp Leu Arg Ile
770                 775                 780

Val Met Cys Leu Met Cys Gly Asp Pro Phe Ser Ala Asp Ile Leu
785                 790                 795                 800

Ser Pro Val Leu Gln Ser Gln Thr Cys Lys Ser Ser His Cys Gly Ser
            805                 810                 815

Ser Asn Ser Val Leu Leu Glu Leu Pro Ile Gly Val His Lys Lys Arg
            820                 825                 830

Ile Glu Leu Ser Val Leu Ser Tyr His Ser Ser Phe Ser Ile Arg Lys
            835                 840                 845

Ser Arg Leu Val His Gly Tyr Ile Val Phe Tyr Ser Ala Lys Arg Lys
850                 855                 860

Ala Ser Leu Ala Met Leu Arg Ala Phe Leu Cys Glu Val Gln Asp Ile
865                 870                 875                 880

Ile Pro Ile Gln Leu Val Ala Leu Thr Asp Gly Ala Ile Asp Val Leu
                885                 890                 895

Asp Asn Asp Leu Ser Arg Glu Gln Leu Thr Glu Gly Glu Glu Ile Ala
            900                 905                 910
```

```
Gln Glu Ile Asp Gly Arg Phe Thr Ser Ile Pro Cys Ser His Pro Gln
    915                 920                 925
His Lys Leu Glu Leu Phe His Pro Phe Phe Lys Asp Val Val Glu Lys
    930                 935                 940
Lys Asn Ile Ile Glu Ala Thr His Met Tyr Asp Asn Val Ala Glu Ala
945                 950                 955                 960
Cys Ser Thr Thr Glu Glu Val Phe Asn Ser Pro Arg Ala Gly Ser Pro
                965                 970                 975
Leu Cys Asn Ser Asn Leu Gln Asp Ser Glu Glu Asp Val Glu Pro Pro
            980                 985                 990
Ser Tyr His Leu Phe Arg Glu Asp  Ala Thr Leu Pro Ser  Leu Ser Lys
        995                 1000                1005
Asp His  Ser Lys Phe Ser Met  Glu Leu Glu Gly Asn  Asp Gly Leu
    1010                1015                1020
Ser Phe  Ile Met Ser Asn Phe  Glu Ser Lys Leu Asn  Asn Lys Val
    1025                1030                1035
Pro Pro  Pro Val Lys Pro Lys  Pro Pro Val His Phe  Glu Ile Thr
    1040                1045                1050
Lys Asp  Leu Ser Tyr Leu Asp  Gln Gly His Arg Glu  Gly Gln Arg
    1055                1060                1065
Lys Ser  Met Ser Ser Ser Pro  Trp Met Pro Gln Asp  Gly Phe Asp
    1070                1075                1080
Pro Ser  Asp Tyr Ala Glu Pro  Met Asp Ala Val Val  Lys Pro Arg
    1085                1090                1095
Asn Glu  Glu Glu Asn Ile Tyr  Ser Val Pro His Asp  Ser Thr Gln
    1100                1105                1110
Gly Lys  Ile Ile Thr Ile Arg  Asn Ile Asn Lys Ala  Gln Ser Asn
    1115                1120                1125
Gly Ser  Gly Asn Gly Ser Asp  Ser Glu Met Asp Thr  Ser Ser Leu
    1130                1135                1140
Glu Arg  Gly Arg Lys Val Ser  Ala Val Ser Lys Pro  Val Leu Tyr
    1145                1150                1155
Arg Thr  Arg Cys Thr Arg Leu  Gly Arg Phe Ala Ser  Tyr Arg Thr
    1160                1165                1170
Ser Phe  Ser Val Gly Ser Asp  Asp Glu Leu Gly Pro  Ile Arg Lys
    1175                1180                1185
Lys Glu  Glu Asp Gln Ala Ser  Gln Gly Tyr Lys Gly  Asp Asn Ala
    1190                1195                1200
Val Ile  Pro Tyr Glu Thr Asp  Glu Asp Pro Arg Arg  Arg Asn Ile
    1205                1210                1215
Leu Arg  Ser Leu Arg Arg Asn  Thr Lys Lys Pro Lys  Pro Lys Pro
    1220                1225                1230
Arg Pro  Ser Ile Thr Lys Ala  Thr Trp Glu Ser Asn  Tyr Phe Gly
    1235                1240                1245
Val Pro  Leu Thr Thr Val Val  Thr Pro Glu Lys Pro  Ile Pro Ile
    1250                1255                1260
Phe Ile  Glu Arg Cys Ile Glu  Tyr Ile Glu Ala Thr  Gly Leu Ser
    1265                1270                1275
Thr Glu  Gly Ile Tyr Arg Val  Ser Gly Asn Lys Ser  Glu Met Glu
    1280                1285                1290
Ser Leu  Gln Arg Gln Phe Asp  Gln Asp His Asn Leu  Asp Leu Ala
    1295                1300                1305
Glu Lys  Asp Phe Thr Val Asn  Thr Val Ala Gly Ala  Met Lys Ser
    1310                1315                1320
```

Phe Phe Ser Glu Leu Pro Asp Pro Leu Val Pro Tyr Ser Met Gln
     1325                1330                1335

Ile Asp Leu Val Glu Ala His Lys Ile Asn Asp Arg Glu Gln Lys
     1340                1345                1350

Leu His Ala Leu Lys Glu Val Leu Lys Lys Phe Pro Lys Glu Asn
     1355                1360                1365

His Glu Val Phe Lys Tyr Val Ile Ser His Leu Asn Arg Val Ser
     1370                1375                1380

His Asn Asn Lys Val Asn Leu Met Thr Ser Glu Asn Leu Ser Ile
     1385                1390                1395

Cys Phe Trp Pro Thr Leu Met Arg Pro Asp Phe Ser Ser Met Asp
     1400                1405                1410

Ala Leu Thr Ala Thr Arg Ser Tyr Gln Thr Ile Ile Glu Leu Phe
     1415                1420                1425

Ile Gln Gln Cys Pro Phe Phe Phe Tyr Asn Arg Pro Ile Ser Glu
     1430                1435                1440

Pro Pro Gly Ala Ala Leu Ala Pro Leu Gln Pro Trp His Pro Leu
     1445                1450                1455

Ser Pro Ser Ser Pro Leu His Leu Leu Pro Val Ser His His Leu
     1460                1465                1470

Pro Ser His Leu Leu Gln Pro Leu Ser Pro Gln Cys Ser His Cys
     1475                1480                1485

Ser Pro Leu Ser Ser Lys Pro Asn Thr Arg Cys Glu Pro Pro Gln
     1490                1495                1500

Pro Arg Lys Gln Glu Asn Gln Leu Ser Ser
     1505                1510

<210> SEQ ID NO 3
<211> LENGTH: 1320
<212> TYPE: DNA
<213> ORGANISM: Homo sapiens

<400> SEQUENCE: 3
atggatccgc tctcagagct gcaggatgat ctgaccttgg atgacaccag cgaggctctg        60
aaccagctga agctggcctc catcgatgag aagaactggc cctcggatga atgcctgac        120 ttccccaagt cagatgactc caaaagcagc tccccggaac ttgtcacaca cctgaagtgg        180
gatgacccat actatgacat cgcccggcac cagatcgtgg aggtggcagg agatgacaag        240
tatgggcgga gatcattgt gtttagtgcc tgtcgaatgc cccccagcca ccagctcgac        300
cacagcaagc tcctggggta cctgaagcac accctggacc agtacgtgga gagtgactac        360
acacttctgt atctgcacca cggcctgacc agcgacaaca gccctccct cagctggctc        420 cgtgatgcct accgggagtt tgaccgcaag tacaagaaga catcaaggc cttgtacatc        480 gtgcatccaa ccatgttcat caaaactctg ctcatcctct tcaagcccct catcagcttc        540
aagttcgggc agaagatctt ctatgtgaat tacctgagcg agctgagcga gcacgtgaag        600
ctggagcagc tggggatccc tcgccaagtg ctcaaatatg cgacttcct gaaatccaca        660 cagaagagcc ccgcgacagc ccccaagccc atgccccac ggcccccct gcccaaccag        720 cagtttggag tctcgctgca gcacctccag gagaagaatc cagagcagga gcccattccc        780
attgtactca gggagactgt tgcctactta caggcccacg ctctcaccac cgagggcatc        840
ttccggaggt cggccaacac ccaagtggtc cgggaagtgc agcagaagta caacatgggg        900
ctgcctgtgg atttcgacca gtacaatgag ctgcacctgc agcagtcat cctcaagacc        960

-continued

```
ttcctccggg agcttcctga gccccctgctc acctttgacc tctaccccca tgtggtgggc    1020
ttcctcaaca ttgatgaaag ccagagggtg ccagcgacac tgcaggtcct ccagacgctg    1080
cccgaggaga actaccaggt gcttcgtttc ctgactgctt tcctggtgca gatttctgca    1140
cacagtgacc agaacaagat gaccaacact aacctggctg ttgttttcgg ccctaacctg    1200
ctgtgggcca aggatgcggc catcaccctc aaggccatta atcccatcaa caccttcacc    1260
aagttccttc tggatcacca aggggagctg ttcccaagcc cggacccccag cgggctctga    1320

<210> SEQ ID NO 4
<211> LENGTH: 439
<212> TYPE: PRT
<213> ORGANISM: Homo sapiens
<220> FEATURE:
<221> NAME/KEY: DOMAIN
<222> LOCATION: (257)..(426)
<223> OTHER INFORMATION: Cdc42GAP domain

<400> SEQUENCE: 4

Met Asp Pro Leu Ser Glu Leu Gln Asp Asp Leu Thr Leu Asp Asp Thr
1               5                   10                  15

Ser Glu Ala Leu Asn Gln Leu Lys Leu Ala Ser Ile Asp Glu Lys Asn
                20                  25                  30

Trp Pro Ser Asp Glu Met Pro Asp Phe Pro Lys Ser Asp Asp Ser Lys
            35                  40                  45

Ser Ser Ser Pro Glu Leu Val Thr His Leu Lys Trp Asp Asp Pro Tyr
        50                  55                  60

Tyr Asp Ile Ala Arg His Gln Ile Val Glu Val Ala Gly Asp Asp Lys
65                  70                  75                  80

Tyr Gly Arg Lys Ile Ile Val Phe Ser Ala Cys Arg Met Pro Pro Ser
                85                  90                  95

His Gln Leu Asp His Ser Lys Leu Leu Gly Tyr Leu Lys His Thr Leu
                100                 105                 110

Asp Gln Tyr Val Glu Ser Asp Tyr Thr Leu Leu Tyr Leu His His Gly
            115                 120                 125

Leu Thr Ser Asp Asn Lys Pro Ser Leu Ser Trp Leu Arg Asp Ala Tyr
        130                 135                 140

Arg Glu Phe Asp Arg Lys Tyr Lys Lys Asn Ile Lys Ala Leu Tyr Ile
145                 150                 155                 160

Val His Pro Thr Met Phe Ile Lys Thr Leu Leu Ile Leu Phe Lys Pro
                165                 170                 175

Leu Ile Ser Phe Lys Phe Gly Gln Lys Ile Phe Tyr Val Asn Tyr Leu
            180                 185                 190

Ser Glu Leu Ser Glu His Val Lys Leu Glu Gln Leu Gly Ile Pro Arg
        195                 200                 205

Gln Val Leu Lys Tyr Asp Asp Phe Leu Lys Ser Thr Gln Lys Ser Pro
    210                 215                 220

Ala Thr Ala Pro Lys Pro Met Pro Pro Arg Pro Pro Leu Pro Asn Gln
225                 230                 235                 240

Gln Phe Gly Val Ser Leu Gln His Leu Gln Glu Lys Asn Pro Glu Gln
                245                 250                 255

Glu Pro Ile Pro Ile Val Leu Arg Glu Thr Val Ala Tyr Leu Gln Ala
            260                 265                 270

His Ala Leu Thr Thr Glu Gly Ile Phe Arg Arg Ser Ala Asn Thr Gln
        275                 280                 285

Val Val Arg Glu Val Gln Gln Lys Tyr Asn Met Gly Leu Pro Val Asp
    290                 295                 300
```

Phe Asp Gln Tyr Asn Glu Leu His Leu Pro Ala Val Ile Leu Lys Thr
305                 310                 315                 320

Phe Leu Arg Glu Leu Pro Glu Pro Leu Leu Thr Phe Asp Leu Tyr Pro
            325                 330                 335

His Val Val Gly Phe Leu Asn Ile Asp Glu Ser Gln Arg Val Pro Ala
            340                 345                 350

Thr Leu Gln Val Leu Gln Thr Leu Pro Glu Glu Asn Tyr Gln Val Leu
        355                 360                 365

Arg Phe Leu Thr Ala Phe Leu Val Gln Ile Ser Ala His Ser Asp Gln
    370                 375                 380

Asn Lys Met Thr Asn Thr Asn Leu Ala Val Val Phe Gly Pro Asn Leu
385                 390                 395                 400

Leu Trp Ala Lys Asp Ala Ala Ile Thr Leu Lys Ala Ile Asn Pro Ile
            405                 410                 415

Asn Thr Phe Thr Lys Phe Leu Leu Asp His Gln Gly Glu Leu Phe Pro
            420                 425                 430

Ser Pro Asp Pro Ser Gly Leu
            435

<210> SEQ ID NO 5
<211> LENGTH: 3684
<212> TYPE: DNA
<213> ORGANISM: Homo sapiens

<400> SEQUENCE: 5

| | | | | | | |
|---|---|---|---|---|---|---|
| atggtggacc | cggtgggctt | cgcggaggcg | tggaaggcgc | agttcccgga | ctcagagccc | 60 |
| ccgcgcatgg | agctgcgctc | agtgggcgac | atcgagcagg | agctgagcg | ctgcaaggcc | 120 |
| tccattcggc | gcctggagca | ggaggtgaac | caggagcgct | tccgcatgat | ctacctgcag | 180 |
| acgttgctgg | ccaaggaaaa | gaagagctat | gaccggcagc | gatggggctt | ccggcgcgcg | 240 |
| gcgcaggccc | ccgacggcgc | ctccgagccc | cgagcgtccg | cgtcgcgccc | gcagccagcg | 300 |
| cccgccgacg | gagccgaccc | gccgcccgcc | gaggagcccg | aggcccggcc | cgacggcgag | 360 |
| ggttctccgg | gtaaggccag | gcccgggacc | gcccgcaggc | ccggggcagc | cgcgtcgggg | 420 |
| gaacgggacg | accggggacc | ccccgccagc | gtggcggcgc | tcaggtccaa | cttcgagcgg | 480 |
| atccggaagg | ccatggcca | gccggggcg | gacgccgaga | gcccttcta | cgtgaacgtc | 540 |
| gagtttcacc | acgagcgcgg | cctggtgaag | gtcaacgaca | aagaggtgtc | ggaccgcatc | 600 |
| agctcccttg | gcagccaggc | catgcagatg | gagcgcaaaa | agtcccagca | cggcgcgggc | 660 |
| tcgagcgtgg | gggatgcatc | caggcccct | taccggggac | gctcctcgga | gagcagctgc | 720 |
| ggcgtcgacg | gcgactacga | ggacgccgag | ttgaacccc | gcttcctgaa | ggacaacctg | 780 |
| atcgacgcca | atggcggtag | caggcccct | tggccgcccc | tggagtacca | gccctaccag | 840 |
| agcatctacg | tcgggggcat | catggaaggg | gagggcaagg | gcccgctcct | gcgcagccag | 900 |
| agcacctctg | agcaggagaa | cgccttacc | tggccccgca | ggtcctactc | ccccggagt | 960 |
| tttgaggatt | gcgaggcgg | ctataccccg | gactgcagct | ccaatgagaa | cctcacctcc | 1020 |
| agcgaggagg | acttctcctc | tggccagtcc | agccgcgtgt | ccccaagccc | caccacctac | 1080 |
| cgcatgttcc | gggacaaaag | ccgctctccc | tcgcagaact | cgcaacagtc | cttcgacagc | 1140 |
| agcagtcccc | ccacgccgca | gtgccataag | cggcaccggc | actgcccggt | tgtcgtgtcc | 1200 |
| gaggccacca | tcgtgggcgt | ccgcaagacc | gggcagatct | ggcccaacga | tgacgagggc | 1260 |
| gccttccatg | gagacgcaga | tggctcgttc | ggaacaccac | ctggatacgg | ctgcgctgca | 1320 |

```
gaccgggcag aggagcagcg ccggcaccaa gatgggctgc cctacattga tgactcgccc    1380
tcctcatcgc cccacctcag cagcaagggc aggggcagcc gggatgcgct ggtctcggga    1440
gccctgaagt ccactaaagc gagtgagctg gacttggaaa agggcttgga gatgagaaaa    1500
tgggtcctgt cgggaatcct ggctagcgag gagacttacc tgagccacct ggaggcactg    1560
ctgctgccca tgaagccttt gaaagccgct gccaccacct ctcagccggt gctgacgagt    1620
cagcagatcg agaccatctt cttcaaagtg cctgagctct acgagatcca aggagtcc      1680
tatgatgggc tcttcccccg cgtgcagcag tggagccacc agcagcgggt gggcgacctc    1740
ttccagaagc tggccagcca gctgggtgtg taccgggcct tcgtggacaa ctacggagtt    1800
gccatggaaa tggctgagaa gtgctgtcag gccaatgctc agtttgcaga aatctccgag    1860
aacctgagag ccagaagcaa caaagatgcc aaggatccaa cgaccaagaa ctctctggaa    1920
actctgctct acaagcctgt ggaccgtgtg acgaggagca cgctggtcct ccatgacttg    1980
ctgaagcaca ctcctgccag ccaccctgac caccccttgc tgcaggacgc cctccgcatc    2040
tcacagaact tcctgtccag catcaatgag gagatcacac cccgacggca gtccatgacg    2100
gtgaagaagg gagagcaccg gcagctgctg aaggacagct tcatggtgga gctggtggag    2160
ggggcccgca agctgcggca cgtcttcctg ttcaccgacc tgcttctctg caccaagctc    2220
aagaagcaga gcggaggcaa aacgcagcag tatgactgca aatggtacat tccgctcacg    2280
gatctcagct tccagatggt ggatgaactg gaggcagtgc ccaacatccc cctggtgccc    2340
gatgaggagc tggacgcttt gaagatcaag atctcccaga tcaagagtga catccagaga    2400
gagaagaggg cgaacaaggg cagcaaggct acggagaggc tgaagaagaa gctgtcggag    2460
caggagtcac tgctgctgct tatgtctccc agcatggcct tcagggtgca cagccgcaac    2520
ggcaagagtt acacgttcct gatctcctct gactatgagc gtgcagagtg gagggagaac    2580
atccgggagc agcagaagaa gtgtttcaga agcttctccc tgacatccgt ggagctgcag    2640
atgctgacca actcgtgtgt gaaactccag actgtccaca gcattccgct gaccatcaat    2700
aaggaagatg atgagtctcc ggggctctat gggtttctga atgtcatcgt ccactcagcc    2760
actggatttta agcagagttc aaatctgtac tgcaccctgg aggtggattc ctttgggtat    2820
tttgtgaata agcaaagac gcgcgtctac agggacacag ctgagccaaa ctggaacgag    2880
ctggaccccgc aggccctgca ggacagagac tggcagcgca ccgtcatcgc catgaatggg    2940
atcgaagtaa agctctcggt caagttcaac agcagggagt tcagcttgaa gaggatgccg    3000
tccccgaaaac agacagggt cttcggagtc aagattgctg tggtcaccaa gagagagagg    3060
tccaaggtgc cctacatcgt gcgccagtgc gtggaggaga tcgagcgccg aggcatggag    3120
gaggtgggca tctaccgcgt gtccggtgtg gccacggaca tccaggcact gaaggcagcc    3180
ttcgacgtca ataacaagga tgtgtcggtg atgatgagcg agatggacgt gaacgccatc    3240
gcaggcacgc tgaagctgta cttccgtgag ctgcccgagc cctcttcac tgacgagttc    3300
taccccaact tcgcagaggg catcgctctt tcagacccgg ttgcaaagga gagctgcatg    3360
ctcaacctgc tgctgtccct gccggaggcc aacctgctca ccttccttttt ccttctggac    3420
cacctgaaaa gggtggcaga gaaggaggca gtcaataaga tgtccctgca caacctcgcc    3480
acggtctttg gccccacgct gctccggccc tccgagaagg agagcaagct ccctgccaac    3540
cccagccagc ctatcaccat gactgacagc tggtccttgg aggtcatgtc ccaggtccag    3600
gtgctgctgt acttcctgca gctggaggcc atccctgccc cggacagcaa gagacagagc    3660
atcctgttct ccaccgaagt ctaa                                           3684
```

```
<210> SEQ ID NO 6
<211> LENGTH: 1227
<212> TYPE: PRT
<213> ORGANISM: Homo sapiens
<220> FEATURE:
<221> NAME/KEY: DOMAIN
<222> LOCATION: (1014)..(1205)
<223> OTHER INFORMATION: BcrGAP domain

<400> SEQUENCE: 6

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365
```

```
Ser Pro Ser Gln Asn Ser Gln Gln Ser Phe Asp Ser Ser Pro Pro
    370                 375                 380

Thr Pro Gln Cys His Lys Arg His Arg His Cys Pro Val Val Val Ser
385                     390                 395                 400

Glu Ala Thr Ile Val Gly Val Arg Lys Thr Gly Gln Ile Trp Pro Asn
                    405                 410                 415

Asp Asp Glu Gly Ala Phe His Gly Asp Ala Asp Gly Ser Phe Gly Thr
                420                 425                 430

Pro Pro Gly Tyr Gly Cys Ala Ala Asp Arg Ala Glu Glu Arg Arg
                435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                     470                 475                 480

Ala Leu Lys Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
                500                 505                 510

Tyr Leu Ser His Leu Glu Ala Leu Leu Leu Pro Met Lys Pro Leu Lys
            515                 520                 525

Ala Ala Ala Thr Thr Ser Gln Pro Val Leu Thr Ser Gln Gln Ile Glu
530                 535                 540

Thr Ile Phe Phe Lys Val Pro Glu Leu Tyr Glu Ile His Lys Glu Ser
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
                580                 585                 590

Ala Phe Val Asp Asn Tyr Gly Val Ala Met Glu Met Ala Glu Lys Cys
            595                 600                 605

Cys Gln Ala Asn Ala Gln Phe Ala Glu Ile Ser Glu Asn Leu Arg Ala
610                 615                 620

Arg Ser Asn Lys Asp Ala Lys Asp Pro Thr Thr Lys Asn Ser Leu Glu
625                 630                 635                 640

Thr Leu Leu Tyr Lys Pro Val Asp Arg Val Thr Arg Ser Thr Leu Val
                645                 650                 655

Leu His Asp Leu Leu Lys His Thr Pro Ala Ser His Pro Asp His Pro
            660                 665                 670

Leu Leu Gln Asp Ala Leu Arg Ile Ser Gln Asn Phe Leu Ser Ser Ile
        675                 680                 685

Asn Glu Glu Ile Thr Pro Arg Arg Gln Ser Met Thr Val Lys Lys Gly
            690                 695                 700

Glu His Arg Gln Leu Leu Lys Asp Ser Phe Met Val Glu Leu Val Glu
705                 710                 715                 720

Gly Ala Arg Lys Leu Arg His Val Phe Leu Phe Thr Asp Leu Leu Leu
                725                 730                 735

Cys Thr Lys Leu Lys Lys Gln Ser Gly Gly Lys Thr Gln Gln Tyr Asp
            740                 745                 750

Cys Lys Trp Tyr Ile Pro Leu Thr Asp Leu Ser Phe Gln Met Val Asp
            755                 760                 765

Glu Leu Glu Ala Val Pro Asn Ile Pro Leu Val Pro Asp Glu Glu Leu
    770                 775                 780

Asp Ala Leu Lys Ile Lys Ile Ser Gln Ile Lys Ser Asp Ile Gln Arg
```

```
                785                 790                 795                 800
Glu Lys Arg Ala Asn Lys Gly Ser Lys Ala Thr Glu Arg Leu Lys Lys
                    805                 810                 815
Lys Leu Ser Glu Gln Glu Ser Leu Leu Leu Met Ser Pro Ser Met
                820                 825                 830
Ala Phe Arg Val His Ser Arg Asn Gly Lys Ser Tyr Thr Phe Leu Ile
                835                 840                 845
Ser Ser Asp Tyr Glu Arg Ala Glu Trp Arg Glu Asn Ile Arg Glu Gln
                850                 855                 860
Gln Lys Lys Cys Phe Arg Ser Phe Ser Leu Thr Ser Val Glu Leu Gln
865                 870                 875                 880
Met Leu Thr Asn Ser Cys Val Lys Leu Gln Thr Val His Ser Ile Pro
                    885                 890                 895
Leu Thr Ile Asn Lys Glu Asp Asp Glu Ser Pro Gly Leu Tyr Gly Phe
                    900                 905                 910
Leu Asn Val Ile Val His Ser Ala Thr Gly Phe Lys Gln Ser Ser Asn
                    915                 920                 925
Leu Tyr Cys Thr Leu Glu Val Asp Ser Phe Gly Tyr Phe Val Asn Lys
                    930                 935                 940
Ala Lys Thr Arg Val Tyr Arg Asp Thr Ala Glu Pro Asn Trp Asn Glu
945                 950                 955                 960
Leu Asp Pro Gln Ala Leu Gln Asp Arg Asp Trp Gln Arg Thr Val Ile
                    965                 970                 975
Ala Met Asn Gly Ile Glu Val Lys Leu Ser Val Lys Phe Asn Ser Arg
                    980                 985                 990
Glu Phe Ser Leu Lys Arg Met Pro Ser Arg Lys Gln Thr Gly Val Phe
                    995                 1000                1005
Gly Val Lys Ile Ala Val Val Thr Lys Arg Glu Arg Ser Lys Val
                    1010                1015                1020
Pro Tyr Ile Val Arg Gln Cys Val Glu Glu Ile Glu Arg Arg Gly
                    1025                1030                1035
Met Glu Glu Val Gly Ile Tyr Arg Val Ser Gly Val Ala Thr Asp
                    1040                1045                1050
Ile Gln Ala Leu Lys Ala Ala Phe Asp Val Asn Asn Lys Asp Val
                    1055                1060                1065
Ser Val Met Met Ser Glu Met Asp Val Asn Ala Ile Ala Gly Thr
                    1070                1075                1080
Leu Lys Leu Tyr Phe Arg Glu Leu Pro Glu Pro Leu Phe Thr Asp
                    1085                1090                1095
Glu Phe Tyr Pro Asn Phe Ala Glu Gly Ile Ala Leu Ser Asp Pro
                    1100                1105                1110
Val Ala Lys Glu Ser Cys Met Leu Asn Leu Leu Leu Ser Leu Pro
                    1115                1120                1125
Glu Ala Asn Leu Leu Thr Phe Leu Phe Leu Leu Asp His Leu Lys
                    1130                1135                1140
Arg Val Ala Glu Lys Glu Ala Val Asn Lys Met Ser Leu His Asn
                    1145                1150                1155
Leu Ala Thr Val Phe Gly Pro Thr Leu Leu Arg Pro Ser Glu Lys
                    1160                1165                1170
Glu Ser Lys Leu Pro Ala Asn Pro Ser Gln Pro Ile Thr Met Thr
                    1175                1180                1185
Asp Ser Trp Ser Leu Glu Val Met Ser Gln Val Gln Val Leu Leu
                    1190                1195                1200
```

```
Tyr Phe Leu Gln Leu Glu Ala Ile Pro Ala Pro Asp Ser Lys Arg
    1205                1210                1215

Gln Ser Ile Leu Phe Ser Thr Glu Val
    1220                1225

<210> SEQ ID NO 7
<211> LENGTH: 280
<212> TYPE: PRT
<213> ORGANISM: Artificial
<220> FEATURE:
<223> OTHER INFORMATION: chimeric fusion peptide/p190RhoGAP plus c-
      terminus tail section of the targeted GTPase

<400> SEQUENCE: 7

Val Pro Leu Thr Thr Val Val Thr Pro Glu Lys Pro Ile Pro Ile Phe
1               5                   10                  15

Ile Glu Arg Cys Ile Glu Tyr Ile Glu Ala Thr Gly Leu Ser Thr Glu
                20                  25                  30

Gly Ile Tyr Arg Val Ser Gly Asn Lys Ser Glu Met Glu Ser Leu Gln
            35                  40                  45

Arg Gln Phe Asp Gln Asp His Asn Leu Asp Leu Ala Glu Lys Asp Phe
        50                  55                  60

Thr Val Asn Thr Val Ala Gly Ala Met Lys Ser Phe Phe Ser Glu Leu
65                  70                  75                  80

Pro Asp Pro Leu Val Pro Tyr Ser Met Gln Ile Asp Leu Val Glu Ala
                85                  90                  95

His Lys Ile Asn Asp Arg Glu Gln Lys Leu His Ala Leu Lys Glu Val
            100                 105                 110

Leu Lys Lys Phe Pro Lys Glu Asn His Glu Val Phe Lys Tyr Val Ile
        115                 120                 125

Ser His Leu Asn Arg Val Ser His Asn Asn Lys Val Asn Leu Met Thr
    130                 135                 140

Ser Glu Asn Leu Ser Ile Cys Phe Trp Pro Thr Leu Met Arg Pro Asp
145                 150                 155                 160

Phe Ser Ser Met Asp Ala Leu Thr Ala Thr Arg Ser Tyr Gln Thr Ile
                165                 170                 175

Ile Glu Leu Phe Ile Gln Gln Cys Pro Phe Phe Phe Tyr Asn Arg Pro
            180                 185                 190

Ile Ser Glu Pro Pro Gly Ala Ala Leu Ala Pro Leu Gln Pro Trp His
        195                 200                 205

Pro Leu Ser Pro Ser Ser Pro Leu His Leu Leu Pro Val Ser His His
    210                 215                 220

Leu Pro Ser His Leu Leu Gln Pro Leu Ser Pro Gln Cys Ser His Cys
225                 230                 235                 240

Ser Pro Leu Ser Ser Lys Pro Asn Thr Arg Cys Glu Pro Pro Gln Pro
                245                 250                 255

Arg Lys Gln Glu Asn Gln Leu Ser Leu Gln Ala Arg Gly Lys
            260                 265                 270

Lys Lys Ser Gly Cys Leu Val Leu
        275                 280

<210> SEQ ID NO 8
<211> LENGTH: 283
<212> TYPE: PRT
<213> ORGANISM: Artificial
<220> FEATURE:
<223> OTHER INFORMATION: chimeric fusion peptide/p190RhoGAP plus c-
      terminus tail section of the targeted GTPase
```

<400> SEQUENCE: 8

```
Val Pro Leu Thr Thr Val Val Thr Pro Glu Lys Pro Ile Pro Ile Phe
1               5                   10                  15

Ile Glu Arg Cys Ile Glu Tyr Ile Glu Ala Thr Gly Leu Ser Thr Glu
                20                  25                  30

Gly Ile Tyr Arg Val Ser Gly Asn Lys Ser Glu Met Glu Ser Leu Gln
            35                  40                  45

Arg Gln Phe Asp Gln Asp His Asn Leu Asp Leu Ala Glu Lys Asp Phe
        50                  55                  60

Thr Val Asn Thr Val Ala Gly Ala Met Lys Ser Phe Phe Ser Glu Leu
65                  70                  75                  80

Pro Asp Pro Leu Val Pro Tyr Ser Met Gln Ile Asp Leu Val Glu Ala
                85                  90                  95

His Lys Ile Asn Asp Arg Glu Gln Lys Leu His Ala Leu Lys Glu Val
                100                 105                 110

Leu Lys Lys Phe Pro Lys Glu Asn His Glu Val Phe Lys Tyr Val Ile
            115                 120                 125

Ser His Leu Asn Arg Val Ser His Asn Asn Lys Val Asn Leu Met Thr
    130                 135                 140

Ser Glu Asn Leu Ser Ile Cys Phe Trp Pro Thr Leu Met Arg Pro Asp
145                 150                 155                 160

Phe Ser Ser Met Asp Ala Leu Thr Ala Thr Arg Ser Tyr Gln Thr Ile
                165                 170                 175

Ile Glu Leu Phe Ile Gln Gln Cys Pro Phe Phe Phe Tyr Asn Arg Pro
            180                 185                 190

Ile Ser Glu Pro Pro Gly Ala Ala Leu Ala Pro Leu Gln Pro Trp His
        195                 200                 205

Pro Leu Ser Pro Ser Ser Pro Leu His Leu Leu Pro Val Ser His His
    210                 215                 220

Leu Pro Ser His Leu Leu Gln Pro Leu Ser Pro Gln Cys Ser His Cys
225                 230                 235                 240

Ser Pro Leu Ser Ser Lys Pro Asn Thr Arg Cys Glu Pro Pro Gln Pro
                245                 250                 255

Arg Lys Gln Glu Asn Gln Leu Ser Ser Leu Gly Lys Arg Tyr Gly Ser
            260                 265                 270

Gln Asn Gly Cys Ile Asn Cys Cys Lys Val Leu
        275                 280
```

<210> SEQ ID NO 9
<211> LENGTH: 298
<212> TYPE: PRT
<213> ORGANISM: Artificial
<220> FEATURE:
<223> OTHER INFORMATION: chimeric fusion peptide/p190RhoGAP plus c-
      terminus tail section of the targeted GTPase

<400> SEQUENCE: 9

```
Val Pro Leu Thr Thr Val Val Thr Pro Glu Lys Pro Ile Pro Ile Phe
1               5                   10                  15

Ile Glu Arg Cys Ile Glu Tyr Ile Glu Ala Thr Gly Leu Ser Thr Glu
                20                  25                  30

Gly Ile Tyr Arg Val Ser Gly Asn Lys Ser Glu Met Glu Ser Leu Gln
            35                  40                  45

Arg Gln Phe Asp Gln Asp His Asn Leu Asp Leu Ala Glu Lys Asp Phe
        50                  55                  60

Thr Val Asn Thr Val Ala Gly Ala Met Lys Ser Phe Phe Ser Glu Leu
```

```
                65                  70                  75                  80
Pro Asp Pro Leu Val Pro Tyr Ser Met Gln Ile Asp Leu Val Glu Ala
                85                  90                  95

His Lys Ile Asn Asp Arg Glu Gln Lys Leu His Ala Leu Lys Glu Val
            100                 105                 110

Leu Lys Lys Phe Pro Lys Glu Asn His Glu Val Phe Lys Tyr Val Ile
        115                 120                 125

Ser His Leu Asn Arg Val Ser His Asn Asn Lys Val Asn Leu Met Thr
    130                 135                 140

Ser Glu Asn Leu Ser Ile Cys Phe Trp Pro Thr Leu Met Arg Pro Asp
145                 150                 155                 160

Phe Ser Ser Met Asp Ala Leu Thr Ala Thr Arg Ser Tyr Gln Thr Ile
                165                 170                 175

Ile Glu Leu Phe Ile Gln Gln Cys Pro Phe Phe Phe Tyr Asn Arg Pro
            180                 185                 190

Ile Ser Glu Pro Pro Gly Ala Ala Leu Ala Pro Leu Gln Pro Trp His
        195                 200                 205

Pro Leu Ser Pro Ser Ser Pro Leu His Leu Leu Pro Val Ser His His
    210                 215                 220

Leu Pro Ser His Leu Leu Gln Pro Leu Ser Pro Gln Cys Ser His Cys
225                 230                 235                 240

Ser Pro Leu Ser Ser Lys Pro Asn Thr Arg Cys Glu Pro Pro Gln Pro
                245                 250                 255

Arg Lys Gln Glu Asn Gln Leu Ser Ser Leu Gln Lys Arg Tyr Gly Ser
            260                 265                 270

Gln Asn Gly Cys Ile Asn Cys Cys Lys Val Leu Leu Gln Val Arg Lys
        275                 280                 285

Asn Lys Arg Arg Arg Gly Cys Pro Ile Leu
    290                 295

<210> SEQ ID NO 10
<211> LENGTH: 215
<212> TYPE: PRT
<213> ORGANISM: Artificial
<220> FEATURE:
<223> OTHER INFORMATION: chimeric fusion peptide/Cdc42GAP plus c-
      terminus tail section of the targeted GTPase

<400> SEQUENCE: 10

Leu Pro Asn Gln Gln Phe Gly Val Ser Leu Gln His Leu Gln Glu Lys
1               5                   10                  15

Asn Pro Glu Gln Glu Pro Ile Pro Ile Val Leu Arg Glu Thr Val Ala
            20                  25                  30

Tyr Leu Gln Ala His Ala Leu Thr Thr Glu Gly Ile Phe Arg Arg Ser
        35                  40                  45

Ala Asn Thr Gln Val Val Arg Glu Val Gln Gln Lys Tyr Asn Met Gly
    50                  55                  60

Leu Pro Val Asp Phe Asp Gln Tyr Asn Glu Leu His Leu Pro Ala Val
65                  70                  75                  80

Ile Leu Lys Thr Phe Leu Arg Glu Leu Pro Glu Pro Leu Leu Thr Phe
                85                  90                  95

Asp Leu Tyr Pro His Val Val Gly Phe Leu Asn Ile Asp Glu Ser Gln
            100                 105                 110

Arg Val Pro Ala Thr Leu Gln Val Leu Gln Thr Leu Pro Glu Glu Asn
        115                 120                 125

Tyr Gln Val Leu Arg Phe Leu Thr Ala Phe Leu Val Gln Ile Ser Ala
```

```
                130                 135                 140
His Ser Asp Gln Asn Lys Met Thr Asn Thr Asn Leu Ala Val Val Phe
145                 150                 155                 160

Gly Pro Asn Leu Leu Trp Ala Lys Asp Ala Ala Ile Thr Leu Lys Ala
                165                 170                 175

Ile Asn Pro Ile Asn Thr Phe Thr Lys Phe Leu Leu Asp His Gln Gly
                180                 185                 190

Glu Leu Phe Pro Ser Pro Asp Pro Ser Gly Leu Pro Glu Pro Lys Lys
                195                 200                 205

Ser Arg Arg Cys Val Leu Leu
    210                 215

<210> SEQ ID NO 11
<211> LENGTH: 244
<212> TYPE: PRT
<213> ORGANISM: Artificial
<220> FEATURE:
<223> OTHER INFORMATION: chimeric fusion peptide/BcrGAP plus c-
      terminus tail section of the targeted GTPase

<400> SEQUENCE: 11

Leu Lys Arg Met Pro Ser Arg Lys Gln Thr Gly Val Phe Gly Val Lys
1               5                   10                  15

Ile Ala Val Val Thr Lys Arg Glu Arg Ser Lys Val Pro Tyr Ile Val
                20                  25                  30

Arg Gln Cys Val Glu Glu Ile Glu Arg Arg Gly Met Glu Glu Val Gly
            35                  40                  45

Ile Tyr Arg Val Ser Gly Val Ala Thr Asp Ile Gln Ala Leu Lys Ala
        50                  55                  60

Ala Phe Asp Val Asn Asn Lys Asp Val Ser Val Met Met Ser Glu Met
65                  70                  75                  80

Asp Val Asn Ala Ile Ala Gly Thr Leu Lys Leu Tyr Phe Arg Glu Leu
                85                  90                  95

Pro Glu Pro Leu Phe Thr Asp Glu Phe Tyr Pro Asn Phe Ala Glu Gly
                100                 105                 110

Ile Ala Leu Ser Asp Pro Val Ala Lys Glu Ser Cys Met Leu Asn Leu
            115                 120                 125

Leu Leu Ser Leu Pro Glu Ala Asn Leu Leu Thr Phe Leu Phe Leu Leu
        130                 135                 140

Asp His Leu Lys Arg Val Ala Glu Lys Glu Ala Val Asn Lys Met Ser
145                 150                 155                 160

Leu His Asn Leu Ala Thr Val Phe Gly Pro Thr Leu Leu Arg Pro Ser
                165                 170                 175

Glu Lys Glu Ser Lys Leu Pro Ala Asn Pro Ser Gln Pro Ile Thr Met
                180                 185                 190

Thr Asp Ser Trp Ser Leu Glu Val Met Ser Gln Val Gln Val Leu Leu
            195                 200                 205

Tyr Phe Leu Gln Leu Glu Ala Ile Pro Ala Pro Asp Ser Lys Arg Gln
        210                 215                 220

Ser Ile Leu Phe Ser Thr Glu Val Pro Val Lys Arg Lys Arg Lys
225                 230                 235                 240

Cys Leu Leu Leu

<210> SEQ ID NO 12
<211> LENGTH: 244
<212> TYPE: PRT
<213> ORGANISM: Artificial
```

-continued

```
<220> FEATURE:
<223> OTHER INFORMATION: chimeric fusion peptide/BcrGAP plus c-
      terminus tail section of the targeted GTPase

<400> SEQUENCE: 12

Leu Lys Arg Met Pro Ser Arg Lys Gln Thr Gly Val Phe Gly Val Lys
1               5                   10                  15

Ile Ala Val Val Thr Lys Arg Glu Arg Ser Lys Val Pro Tyr Ile Val
                20                  25                  30

Arg Gln Cys Val Glu Glu Ile Glu Arg Arg Gly Met Glu Glu Val Gly
            35                  40                  45

Ile Tyr Arg Val Ser Gly Val Ala Thr Asp Ile Gln Ala Leu Lys Ala
        50                  55                  60

Ala Phe Asp Val Asn Asn Lys Asp Val Ser Val Met Met Ser Glu Met
65                  70                  75                  80

Asp Val Asn Ala Ile Ala Gly Thr Leu Lys Leu Tyr Phe Arg Glu Leu
                85                  90                  95

Pro Glu Pro Leu Phe Thr Asp Glu Phe Tyr Pro Asn Phe Ala Glu Gly
            100                 105                 110

Ile Ala Leu Ser Asp Pro Val Ala Lys Glu Ser Cys Met Leu Asn Leu
        115                 120                 125

Leu Leu Ser Leu Pro Glu Ala Asn Leu Leu Thr Phe Leu Phe Leu Leu
    130                 135                 140

Asp His Leu Lys Arg Val Ala Glu Lys Glu Ala Val Asn Lys Met Ser
145                 150                 155                 160

Leu His Asn Leu Ala Thr Val Phe Gly Pro Thr Leu Leu Arg Pro Ser
                165                 170                 175

Glu Lys Glu Ser Lys Leu Pro Ala Asn Pro Ser Gln Pro Ile Thr Met
            180                 185                 190

Thr Asp Ser Trp Ser Leu Glu Val Met Ser Gln Val Gln Val Leu Leu
        195                 200                 205

Tyr Phe Leu Gln Leu Glu Ala Ile Pro Ala Pro Asp Ser Lys Arg Gln
    210                 215                 220

Ser Ile Leu Phe Ser Thr Glu Val Pro Thr Arg Gln Gln Lys Arg Ala
225                 230                 235                 240

Cys Ser Leu Leu

<210> SEQ ID NO 13
<211> LENGTH: 244
<212> TYPE: PRT
<213> ORGANISM: Artificial
<220> FEATURE:
<223> OTHER INFORMATION: chimeric fusion peptide/BcrGAP plus c-
      terminus tail section of the targeted GTPase

<400> SEQUENCE: 13

Leu Lys Arg Met Pro Ser Arg Lys Gln Thr Gly Val Phe Gly Val Lys
1               5                   10                  15

Ile Ala Val Val Thr Lys Arg Glu Arg Ser Lys Val Pro Tyr Ile Val
                20                  25                  30

Arg Gln Cys Val Glu Glu Ile Glu Arg Arg Gly Met Glu Glu Val Gly
            35                  40                  45

Ile Tyr Arg Val Ser Gly Val Ala Thr Asp Ile Gln Ala Leu Lys Ala
        50                  55                  60

Ala Phe Asp Val Asn Asn Lys Asp Val Ser Val Met Met Ser Glu Met
65                  70                  75                  80

Asp Val Asn Ala Ile Ala Gly Thr Leu Lys Leu Tyr Phe Arg Glu Leu
```

```
                    85                  90                  95
Pro Glu Pro Leu Phe Thr Asp Glu Phe Tyr Pro Asn Phe Ala Glu Gly
            100                 105                 110

Ile Ala Leu Ser Asp Pro Val Ala Lys Glu Ser Cys Met Leu Asn Leu
            115                 120                 125

Leu Leu Ser Leu Pro Glu Ala Asn Leu Leu Thr Phe Leu Phe Leu Leu
            130                 135                 140

Asp His Leu Lys Arg Val Ala Glu Lys Glu Ala Val Asn Lys Met Ser
145                 150                 155                 160

Leu His Asn Leu Ala Thr Val Phe Gly Pro Thr Leu Leu Arg Pro Ser
                165                 170                 175

Glu Lys Glu Ser Lys Leu Pro Ala Asn Pro Ser Gln Pro Ile Thr Met
            180                 185                 190

Thr Asp Ser Trp Ser Leu Glu Val Met Ser Gln Val Gln Val Leu Leu
            195                 200                 205

Tyr Phe Leu Gln Leu Glu Ala Ile Pro Ala Pro Asp Ser Lys Arg Gln
            210                 215                 220

Ser Ile Leu Phe Ser Thr Glu Val Pro Val Lys Lys Pro Gly Lys Lys
225                 230                 235                 240

Cys Thr Val Phe
```

```
<210> SEQ ID NO 14
<211> LENGTH: 15
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 14

Leu Gln Ala Arg Arg Gly Lys Lys Lys Ser Gly Cys Leu Val Leu
1               5                   10                  15

<210> SEQ ID NO 15
<211> LENGTH: 18
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 15

Leu Gln Lys Arg Tyr Gly Ser Gln Asn Gly Cys Ile Asn Cys Cys Lys
1               5                   10                  15

Val Leu

<210> SEQ ID NO 16
<211> LENGTH: 15
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 16

Leu Gln Val Arg Lys Asn Lys Arg Arg Arg Gly Cys Pro Ile Leu
1               5                   10                  15

<210> SEQ ID NO 17
<211> LENGTH: 12
<212> TYPE: PRT
<213> ORGANISM: Artificial
```

```
<220> FEATURE:
<223> OTHER INFORMATION: synthetic construct/c-terminus tail section of
      the targeted GTPase

<400> SEQUENCE: 17

Pro Glu Pro Lys Lys Ser Arg Arg Cys Val Leu Leu
1               5                   10

<210> SEQ ID NO 18
<211> LENGTH: 12
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 18

Pro Val Lys Lys Arg Lys Arg Lys Cys Leu Leu Leu
1               5                   10

<210> SEQ ID NO 19
<211> LENGTH: 12
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 19

Pro Thr Arg Gln Gln Lys Arg Ala Cys Ser Leu Leu
1               5                   10

<210> SEQ ID NO 20
<211> LENGTH: 12
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 20

Pro Val Lys Lys Pro Gly Lys Lys Cys Thr Val Phe
1               5                   10

<210> SEQ ID NO 21
<211> LENGTH: 12
<212> TYPE: PRT
<213> ORGANISM: Artificial
<220> FEATURE:
<223> OTHER INFORMATION: synthetic construct of a membrane-translocating
      peptide

<400> SEQUENCE: 21

Pro Thr Arg Gln Gln Lys Arg Pro Cys Ser Leu Leu
1               5                   10

<210> SEQ ID NO 22
<211> LENGTH: 14
<212> TYPE: PRT
<213> ORGANISM: Artificial
<220> FEATURE:
<223> OTHER INFORMATION: synthetic construct of a membrane-translocating
      peptide

<400> SEQUENCE: 22

Pro Gln Pro Thr Arg Gln Gln Lys Arg Pro Cys Ser Leu Leu
1               5                   10
```

```
<210> SEQ ID NO 23
<211> LENGTH: 16
<212> TYPE: PRT
<213> ORGANISM: Artificial
<220> FEATURE:
<223> OTHER INFORMATION: synthetic construct of a membrane-translocating
      peptide

<400> SEQUENCE: 23

Gly Arg Arg Arg Arg Arg Arg Arg Gly Thr Arg Gln Gln Lys Arg Pro
1               5                   10                  15

<210> SEQ ID NO 24
<211> LENGTH: 16
<212> TYPE: PRT
<213> ORGANISM: Artificial
<220> FEATURE:
<223> OTHER INFORMATION: synthetic construct of a membrane-translocating
      peptide

<400> SEQUENCE: 24

Gly Arg Arg Arg Arg Arg Arg Arg Gly Arg Pro Arg Gln Thr Gln Lys
1               5                   10                  15

<210> SEQ ID NO 25
<211> LENGTH: 20
<212> TYPE: PRT
<213> ORGANISM: Artificial
<220> FEATURE:
<223> OTHER INFORMATION: synthetic construct of a membrane-translocating
      peptide

<400> SEQUENCE: 25

Gly Arg Arg Arg Arg Arg Arg Arg Gly Thr Arg Gln Gln Lys Arg Pro
1               5                   10                  15

Cys Ser Leu Leu
            20

<210> SEQ ID NO 26
<211> LENGTH: 78
<212> TYPE: DNA
<213> ORGANISM: Artificial
<220> FEATURE:
<223> OTHER INFORMATION: DNA primer sequence used in PCR

<400> SEQUENCE: 26
gcgaattctc acaagacaag gcaaccagat tttttcttcc cacgtctagc ttgcagagaa        60
gacaactgat tttcctgc                                                     78

<210> SEQ ID NO 27
<211> LENGTH: 85
<212> TYPE: DNA
<213> ORGANISM: Artificial
<220> FEATURE:
<223> OTHER INFORMATION: DNA primer sequence used in PCR

<400> SEQUENCE: 27
gcgaattctc atagcacctt gcagcagttg atgcagccgt tctgggagcc gtagcttctg        60
cagagaagac aactgatttt cctgc                                             85

<210> SEQ ID NO 28
<211> LENGTH: 78
<212> TYPE: DNA
<213> ORGANISM: Artificial
<220> FEATURE:
<223> OTHER INFORMATION: DNA primer sequence used in PCR
```

```
<400> SEQUENCE: 28
gcgaattctc agagaatggg acagcccctc cgacgcttgt tcttgcggac ctggagagaa        60
gacaactgat tttcctgc                                                      78
```

CHIMERIC PEPTIDES FOR THE REGULATION OF GTPASES

RELATED APPLICATIONS

This application is a continuation of U.S. application Ser. No. 13/036,964, filed Feb. 28, 2011 and published as U.S. Patent Application Publication Number 2011-0212898 on Sep. 1, 2011, which is a continuation of U.S. patent application Ser. No. 12/348,762, filed Jan. 5, 2009 and published as U.S. Patent Application Publication Number 2009-0203617 on Aug. 13, 2009 and issued as U.S. Pat. No. 7,915,384, which is a continuation of U.S. application Ser. No. 10/918,648, filed Aug. 12, 2004 and published as U.S. Patent Application Publication Number 2005-0069553 on Mar. 31, 2005, now abandoned, which claims priority to U.S. Provisional application 60/494,719, filed Aug. 13, 2003. The entireties of the aforementioned applications are hereby incorporated by reference.

This invention was made with government support under GM60523 awarded by the National Institutes of Health. The government has certain rights in the invention.

REFERENCE TO SEQUENCE LISTING

The present application is being filed along with a Sequence Listing in electronic format. The Sequence Listing is provided as a file entitled CHMC21001C2.TXT, created Feb. 28, 2011, which is 57.4 Kb in size. The information in the electronic format of the Sequence Listing is incorporated herein by reference in its entirety.

FIELD OF THE INVENTION

The present invention generally relates to chimeric peptides capable of regulating GTPases, and more particularly, to methods of targeting individual GTPases by using GTPase-activating proteins. Such proteins may be used for the treatment of cancers and other GTPase-related diseases.

BACKGROUND OF THE INVENTION

The Ras-related Rho family of small GTPases is involved in a wide variety of cellular processes, including the regulation of the actin cytoskeletal organization, cell-to-cell or cell-to-extracellular matrix adhesion, intracellular membrane trafficking, gene transcription, apoptosis and cell cycle progression. Like the GTPase, Ras, the Rho family of GTPases exist in an inactive, GDP-bound and an active, GTP-bound conformation. Rho GTPases are activated by a class of positive regulators, the Dbl family guanine nucleotide exchange factors (GEFs[1]) that catalyze the release of bound GDP and facilitate the binding of GTP, whereas deactivation of Rho proteins is achieved through their intrinsic GTP-hydrolytic activities that are further stimulated by a class of negative regulators, the GTPase-activating proteins (GAPs). A third class of regulators of Rho GTPases, the Rho GDP-dissociation inhibitors, can negatively impact Rho protein activities by sequestering them in the GDP-bound state and preventing effective cycling between the two conformational states. Upon binding to GTP, Rho GTPases may further interact with an array of potential effector molecules to elicit cellular responses.

It has become increasingly clear that Rho proteins play important roles in many aspects of cancer development and each member of the Rho family may be involved to a different extent at different tumor progression stages. For example, it was shown that constitutively active RhoA has oncogenic potential and RhoA acts as a signaling component in Ras-induced transformation. Furthermore, RhoA promotes the invasiveness of rat hepatoma cells and induces metastasis of NIH 3T3 fibroblasts, while RhoC was revealed as a key regulator of migration and metastasis in a human melanoma cell line. Upon introduction into normal mammalian epithelial cells, RhoC readily caused transformation and invasion, leading to an inflammatory breast cancer cell phenotype. On the other hand, RhoB is required for the apoptotic responses induced by farnesyltransferase inhibitors or DNA damaging agents and may have a suppressor or negative modifier function in cancer progression. Unlike Ras, there are no reports of mutation-caused constitutive activation of Rho proteins in tumors. Recent studies of primary human tumors revealed that many Rho GTPases, including RhoA and RhoC, are highly expressed in a variety of cancer types such as colon, lung, testicular germ cell, head and neck squamous cell carcinoma, pancreatic ductal adenocarcinoma, and inflammatory breast, and in some cases, the Rho protein upregulation and/or overexpression correlates with poor prognosis. These observations help put Rho proteins in a lineup of potential molecular targets for anti-cancer therapy.

SUMMARY OF THE INVENTION

One embodiment is a chimeric polypeptide, having: a GAP activity domain; and at least one targeting domain, wherein said targeting domain targets at least one specific GTPase protein. In one aspect, the targeting domain is a C-terminal sequence from a GTPase. (is derived from a C-terminal sequence of GTPase. In a further aspect, the chimeric polypeptide also has a membrane translocating protein domain. In one aspect, the GTPase is a Rho GTPase. In a further aspect, the chimeric peptide also has 6-12 amino acids at either end of the chimeric polypeptide. In one aspect, the Rho C-terminal sequence is C-terminal to the GAP activity domain. Alternatively, it is N-terminal to the GAP activity domain. In one aspect, the GAP activity domain is a peptide sequence containing the minimum structural domain necessary for GTPase activating protein activity. In a further aspect, the GAP activity domain is a Rho family GAP selected from the group consisting of p50RhoGAP, p190, p122-RhoGAP, p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants. Alternatively, the GAP domain is a polypeptide fragment of a GAP GTPase domain from a GAP protein, wherein the fragment comprises at least 15, 20, 25, 30, 40, 50, 60, 70, 80, 90, 100, 125, 150, 170, 200, 250 or more contiguous amino acids of the amino acid sequence of a GAP protein.

In one aspect, the specificity domain is derived from the C-terminus amino acid sequence of a GTPase selected from the group consisting of RhoA, RhoB, RhoC, Cdc42, Rac1, Rac2, Rac3, TC10, RhoG, RhoD, Chp, WRCH1, TCL, and RIF. In a further aspect, the specificity domain is a GTPase fragment comprises at least 1, 2, 3, 4, 5, 6, 7, 8, 9, 10, 11, 12, 13, 14, 15, 16, 17, 18, 19, 20, 21, 22, 23, 24, 25, 30, or more contiguous amino acids of the C-terminus amino acid sequence of a GTPase.

The chimeric polypeptide, wherein the C-terminal sequence is from one of the members of the RhoGTPase family. In one aspect, the RhoGTPase is selected from the group consisting of RhoA, RhoB, RhoC, Cdc42, Rac1, Rac2, Rac3, TC10, RhoG, RhoD, Chp, WRCH1, TCL, and RIF.

A further embodiment is a chimeric polypeptide as defined above, wherein the GAP domain peptide is a polypeptide fragment of a GAP GTPase domain from a GAP protein, wherein the fragment comprises an amino acid sequence of the formula: $X_N$-GAP-$X_C$, wherein "GAP" is the polypeptide fragment of a GAP GTPase domain from a GAP protein, wherein $X_N$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40 or more contiguous amino acids of the N-terminus amino acid sequence of a GAP protein; and wherein $X_C$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more contiguous amino acids of the C-terminus amino acid sequence of a GAP protein.

In one aspect, the $X_N$ is a polypeptide fragment wherein the fragment having at least 1, 2, 3, 4, 5, 6, 7, 8, 9, 10, 11, 12, 13, 14, 15, 16, 17, 18 or more contiguous amino acids of an amino acid sequence selected from the group consisting of amino acids 1-1260 of SEQ ID NO: 2, amino acids 1-256 of SEQ ID NO: 4, amino acids 1-1013 of SEQ ID NO: 6, or fragments thereof. In a further aspect, the $X_N$ is selected from the group consisting of amino acids 1249-1260 of SEQ ID NO: 2, amino acids 237-256 of SEQ ID NO: 4, amino acids 996-1013 of SEQ ID NO: 6, or fragments thereof. In a further aspect, the $X_C$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more contiguous amino acids of the amino acids 1432-1513 of SEQ ID NO:2, amino acids 427-439 of SEQ ID NO:4, amino acids 1206-1227 of SEQ ID NO:6, or fragments thereof. In one aspect, the $X_C$ is selected from the group consisting of amino acids 1432-1513 of SEQ ID NO:2, amino acids 427-439 of SEQ ID NO:4, amino acids 1206-1227 of SEQ ID NO:6, and fragments thereof. In one aspect, the targeting polypeptide specificity domain is a peptide fragment wherein the fragment comprises at least 1, 2, 3, 4, 5, 6, 7, 8, 9, 10, 11, 12, 13, 14, 15, 16, 17, 18 or more contiguous amino acids of a sequence selected from the group consisting of the amino acid sequences: SEQ ID NO:14, SEQ ID NO:15, SEQ ID NO:16, SEQ ID NO:17, SEQ ID NO:18, SEQ ID NO:19, SEQ ID NO:20 and fragments thereof. In a further aspect, the targeting polypeptide fragment comprises an amino acid sequence selected from the group consisting of amino acids: SEQ ID NO:14, SEQ ID NO:15, SEQ ID NO:16, SEQ ID NO:17, SEQ ID NO:18, SEQ ID NO:19, SEQ ID NO:20 and fragments thereof. A further aspect is a chimeric polypeptide further having a membrane-translocating peptide, which may have a membrane-associating isoprenylation modification. In one aspect, the membrane translocating protein comprises a lipid modified peptide. In a further aspect, the membrane translocating protein is a peptide of about 8 to about 50 residues. In a further aspect, the membrane-translocating peptide is a peptide of about 8 to about 50 residues comprising at least eight consecutive residues of an amino acid sequence selected from the group consisting of: SEQ ID NO:21, SEQ ID NO:22, SEQ ID NO:23, SEQ ID NO:24, SEQ ID NO:25, and fragments thereof. In one aspect, the membrane-translocating peptide is an amino acid sequence having about 8 to about 24 residues comprising at least eight consecutive residues of an amino acid sequence selected from the group consisting of: SEQ ID NO:21, SEQ ID NO:22, SEQ ID NO:23, SEQ ID NO:24, SEQ ID NO:25, and fragments thereof. In a further aspect, the membrane-translocating peptide is a sequence of amino acids generally of a length of about 8 to about 50 or more amino acid residues, wherein at least 55% of the residues are hydrophobic such that they have a hydrophobic, lipid-soluble portion. In one aspect, the membrane translocation sequence the amino acid sequence is selected from the group consisting of Pro-Thr-Arg-Gln-Gln-Lys-Arg-Pro-Cys-Ser-Leu-Leu (SEQ ID NO:21), Pro-Gln-Pro-Thr-Arg-Gln-Gln-Lys-Arg-Pro-Cys-Ser-Leu-Leu, (SEQ ID NO:22), Gly-Arg-Arg-Arg-Arg-Arg-Arg-Arg-Gly-Thr-Arg-Gln-Gln-Lys-Arg-Pro, (SEQ ID NO:23), Gly-Arg-Arg-Arg-Arg-Arg-Arg-Arg-Gly-Arg-Pro-Arg-Gln-Thr-Gln-Lys, (SEQ ID NO:24), and Gly-Arg-Arg-Arg-Arg-Arg-Arg-Arg-Gly-Thr-Arg-Gln-Gln-Lys-Arg-Pro-Cys-Leu-Leu (SEQ ID NO:25). In a further aspect, the chimeric polypeptide comprises at least 15, 20, 30, 40, 50, 60, 70, 80, 90, 100, 125, 150, 175, 200, 250 amino acids (e.g., contiguous amino acids) of an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13.

The chimeric polypeptide of claim 1, wherein the chimeric polypeptide comprises an amino acid sequence selected from the group consisting of SEQ ID NO:7, SEQ ID NO:8, SEQ ID NO:9, SEQ ID NO:10, SEQ ID NO:11, SEQ ID NO:12, or SEQ ID NO:13.

One embodiment is a composition having a polypeptide as described above in a pharmaceutically acceptable carrier.

A further embodiment is a method of treating a disease related to up-regulation of GTPase activity in a mammal, by administering to the mammal a composition as disclosed above in an amount effective to reduce the GTPase activity. In one aspect, the disease is a GTP hydrolysis-related disorder.

One embodiment is a method for modulating GTPase activity in a cell, by: contacting said cell with an active compound that modulates GTPase activity, wherein the active compound is a chimeric polypeptide comprising: a) a GAP activity domain and b) at least one specificity domain. In one aspect, a step of Administering the composition to the patient in an amount effective to inhibit GTPase activity is provided. In one aspect, the cancer is characterized by increased activity of a GTPase.

BRIEF DESCRIPTION OF THE DRAWINGS

FIG. 1 depicts the fusion peptides RhoA-C (SEQ ID NO:14), RhoB-C (SEQ ID NO:15), RhoC-C (SEQ ID NO:16), Cdc42-C (SEQ ID NO:17), Rac1-C (SEQ ID NO:18), Rac2-C (SEQ ID NO:19), and Rac3-C (SEQ ID NO:20).

DETAILED DESCRIPTION OF THE PREFERRED EMBODIMENT

Figure 1:
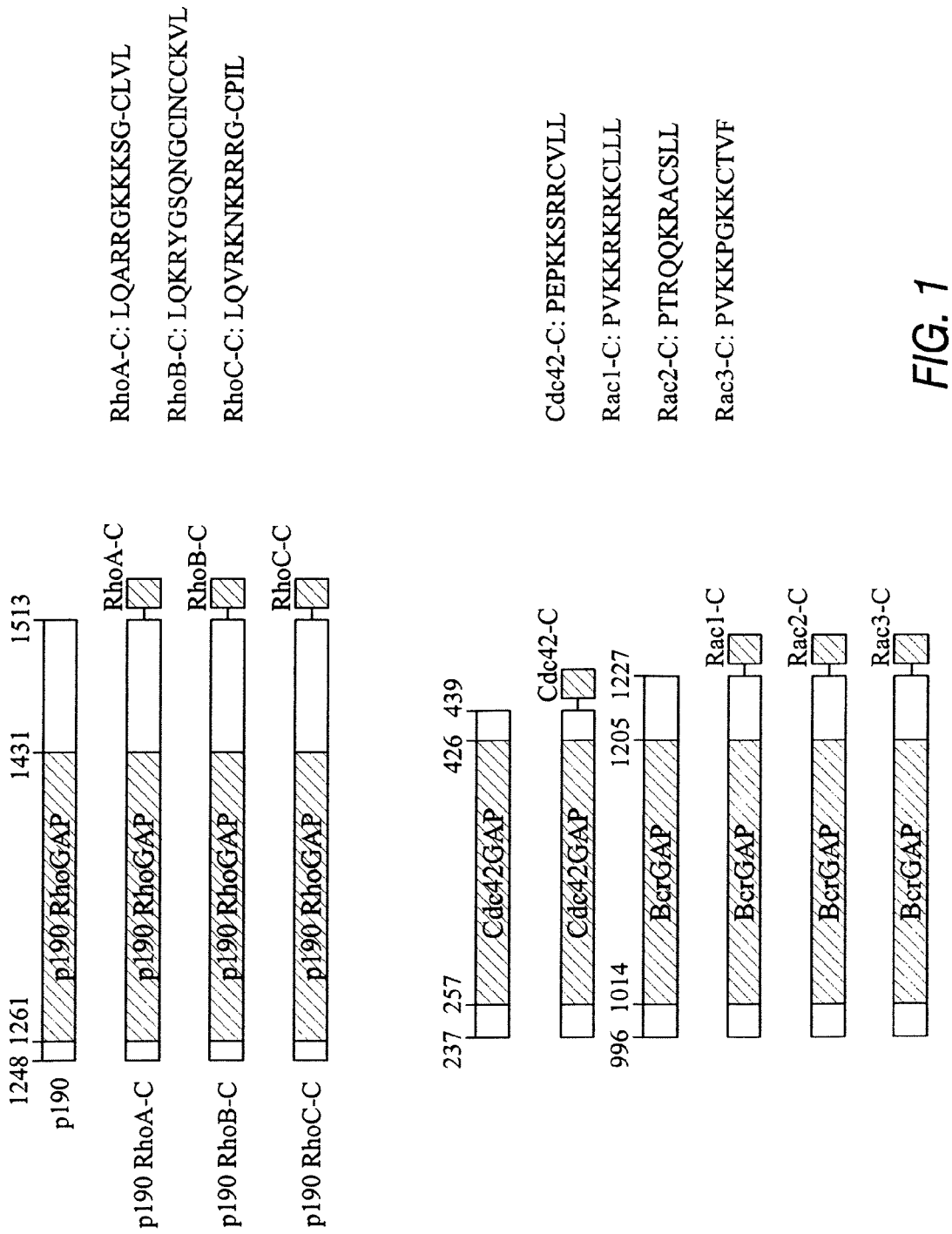
FIG. 1 is a graphical depiction of the fusion peptides between some example GAP domains and various C-terminal intracellular targeting sequences. In particular.

The disclosed compounds are potent and selective regulators of GTPases. These compounds can be used to specifically target GTPases in a very specific manner, for example, RhoA can be targeted without affecting RhoB or RhoC or other Rho GTPase activity in cells. This can be used to treat disorders in cells, such as human tumor cells. Further, these inhibitors can be used to treat diseases, such as cancer, that are associated with GTPase disregulation. The disclosure details how such an approach targeting specific GTPase activity could be useful in reversing cell phenotypes associated with disregulation of a distinct subtype of a GTPase, such as a Rho GTPase.

Currently available molecular tools to target Rho GTPase pathways at the small G-protein level include the dominant negative mutants of Rho proteins (Feig, L. A., 1999, Nat. Cell Biol. 1, E25-E27, herein incorporated by reference in its entirety), the p21-binding domain (PBD) of effectors and a class of bacterial toxins that can modify Rho GTPase functions. Although they have been widely used in cell biological studies, each of these reagents has their own drawbacks. The dominant negative forms of Rho proteins act by sequestering the upstream GEF activators of endogenous Rho GTPases and tend to be non-specific among closely related Rho family members. Further, due to their non-catalytic nature, a 3-5 fold overexpression vs. the endogenous Rho protein level is typically needed for effective blockage of the endogenous activity, and this may not be desirable in many in vivo situations. Similarly, the limited specificity of effector PBDs and bacterial toxins such as *C. botulinum* C3-transferase is worrisome in terms of differentiating the roles of highly homologous isoforms such as RhoA, RhoB and RhoC. Furthermore, very little is known about the anti-cancer potential of these Rho GTPases inhibitors.

Since Rho GAPs have been established as the major class of negative regulators of Rho GTPase signaling and some of them are actually known for their tumor suppressor function, another possible approach for inhibiting Rho GTPase activities in tumor cells is to employ Rho GAPs as antagonists for Rho activities. The conserved GAP domain in Rho GAPs contains the necessary and sufficient structural determinants for Rho protein recognition and GTPase catalysis and displays limited substrate specificity. For example, the RhoGAP domain of p190 RhoGAP can catalyze GTP hydrolysis of RhoA, RhoB and RhoC equally well but works weakly on Rac or Cdc42. It depends on other regulatory domains in the RhoGAP to direct and regulate substrate selection and catalysis in vivo. Conversely, although Rho proteins may share up to 90% sequence identity, each Rho subtype appears to play distinct roles in cellular transformation and metastasis. The differences in Rho GTPase functions may come in part from their distinct subcellular localization patterns that are mostly determined by the unique C-terminal hypervariable sequences in each case (Qui, et al. 1995, PNAS 92, 11781-11785, herein incorporated by reference in its entirety). Although RhoA, RhoB and RhoC are equally effective in stimulating actin stress fiber formation and focal complex assembly in NIH 3T3 cells, RhoA and RhoB are capable of transforming cells whereas RhoC induces cell migration.

The disclosure herein provides methods and compositions of novel chimeric polypeptides and nucleic acids coding for chimeric GAP proteins or polypeptides (CGP). The activities of a chimeric GAP polypeptides can be assayed, e.g., as described below in the examples or according to methods that the skilled worker would know. The chimera comprise at least two regions: a GAP region (GAP peptide) which has a basic function of inhibition of the GTPases and has some function in specificity. However, the GAP peptide possesses only so much specificity as can target a family of GTPases. Further specificity can be provided by a targeting peptide (targeting region). This peptide includes a domain or motif which targets the chimeric protein to a specific part of the cell. The targeting peptide can be placed N-terminal or C-terminal to the GAP domain. The peptide may also include a membrane translocating domain which allows the fusion or chimeric protein to be moved across lipid membranes. These regions, the motifs and domains, and the minimum region for activity will be further described herein and with reference to the Examples.

Thus, one embodiment relates to compounds and their uses, particularly in the pharmaceutical industry. Compounds are disclosed having anti-proliferative activities. Further, methods for treating various diseases associated with abnormal cell proliferation, including cancer, by administering the compounds are disclosed. The compounds can be included in pharmaceutical compositions that are useful for treating any diseases associated with abnormal GTPase activity and particularly useful to treat cancers.

Rho GTPases are exemplary GTPases and key regulators of multiple cell functions related to cancer development. They affect cell-to-cell or cell-to-extracellular matrix adhesion, cell movement and morphological transformation, gene induction, apoptosis and cell cycle progression. Moreover, RhoA, Rac1 and Cdc42 have been implicated as essential components for Ras induced transformation. Accumulating evidence points to specific roles of individual members of Rho family in different aspects of tumor development, including increased proliferation, loss of contact inhibition, transformation, invasion into the adjacent tissues and metastasis to the distant organs. Similar to Ras, Rho GTPases and the signaling pathways controlled by them may therefore make attractive targets for therapeutic intervention in cancer.

The RhoGAP family regulatory proteins of Rho GTPases include over 70 mammalian members (Moon, et al. 2003 *Trends Cell Biol.* 13, 13-22, herein included by reference in its entirety). The GAP activities of RhoGAPs are tightly controlled in cells via complex protein-protein or protein-lipid interactions so that the Rho GTPases would not be in the off-state all the time. Many RhoGAP domains, however, appear to represent a constitutively active structural module and display limited specificity toward the Rho GTPase substrates. Under overexpression or microinjection conditions, the RhoGAP domain alone could cause Rho GTPase downregulation and disruption of certain Rho-mediated cellular functions (Ridley, et al. 1993 *EMBO J.* 12, 5151-60). This likely is due to partial saturation of intracellular compartments by the introduced RhoGAP domain and may not be desirable in studies to extract more specific function of individual members of Rho GTPases. In this context, the concern for specificity when utilizing RhoGAP domain alone for downregulation of Rho proteins is similar to the use of dominant negative Rho GTPases or bacterial toxins.

Methods and compounds herein take advantage of the negative regulatory role of the RhoGAP domain to specifically downregulate individual Rho protein activity. Examples of such methods and compounds include but are not limited to: p190GAP, Cdc42GAP or BcrGAP fused with the RhoA, RhoB, RhoC, Cdc42, Rac1, Rac2 and Rac3 C-terminal sequences are useful for specific downregulation of the respective cellular Rho GTPase activities.

Previous gene targeting studies of RhoB function have shown that distinct from the positive influence on tumor growth or metastasis by RhoA or RhoC, RhoB may act as a negative modifier or suppressor in cancer development, mediating cellular responses to DNA damage or farnesyltransferase inhibitors. Thus, achieving specific targeting of different subtypes of Rho proteins is highly desirable in the treatment of cell proliferation diseases, e.g., tumor cells to reverse the growth and/or invasion phenotypes caused by overexpression of RhoA or RhoC while preserving the tumor suppressor function of RhoB.

One embodiment is RhoGAP-Rho chimeras that are biochemically active as GAPs for Rho GTPases in vitro and localized to the distinct intracellular locations specified by the C-terminal sequences of Rho peptides. The RhoGAP based approach specifically downregulates the biochemical and biological activity of individual Rho subtypes in cells.

The discovery of nucleic acid sequences encoding GTPase-activating proteins and variants thereof provides new compositions that are useful in the characterization, diagnosis, prevention, and treatment of cell proliferative disorders, including cancer. One embodiment provides for Rho-specific chimeric peptides.

A further embodiment is methods for importing the biologically active chimeric peptides into intact cells. Such molecules can be engineered by forming a complex by attaching an importation competent signal peptide sequence to a selected biologically active chimeric GAP molecule and administering the complex to the cell.

Before the present proteins, nucleotide sequences, and methods are described, it is understood that the methods and compositions disclosed herein are not limited to the particular methodology, protocols, cell lines, vectors, and reagents described as these may vary. It is also to be understood that the terminology used herein is for the purpose of describing particular embodiments only, and is not intended to limit the scope of the present invention that will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the cell lines, vectors, and methodologies that are reported in the publications that might be used in connection with the invention. Nothing herein is to be construed as an admission that the invention is not entitled to antedate such disclosure by virtue of prior invention.

DEFINITIONS

"Active" or "activity" for the purposes herein refers to form(s) of a GTPase or GAP polypeptide that retain a biological and/or an immunological activity of native or naturally-occurring GAP, wherein "biological" activity refers to a biological function (either inhibitory or stimulatory) caused by a native or naturally-occurring GAP.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W and G. S. Dveksler (1995) PCR Primer, a Laboratory Manual, Cold Spring Harbor Press, Plainview, N.Y.).

The term "antisense", as used herein, refers to nucleotide sequences that are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promote, that permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. "Biological activity" refers to a function or set of activities performed by a molecule in a biological context (i.e., in an organism or an in vitro facsimile thereof). Biological activities may include the induction of extracellular matrix secretion from responsive cell lines, the induction of hormone secretion, the induction of chemotaxis, the induction of mitogenesis, the induction of differentiation, or the inhibition of cell division of responsive cells. A recombinant protein or peptide is considered to be biologically active if it exhibits one or more biological activities of its native counterpart.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and PLURONICS.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhne-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

As used herein, a "chimeric GAP polypeptide" or "CGP" means a polypeptide, or a nucleic acid coding for a chimeric GAP polypeptide, which polypeptide has a specific binding affinity for a G-proteins (in particular RhoA, RhoB, RhoC, Cdc42, Rac1, Rac2, Rac3, TC10, RhoG, RhoD, Chp, WRCH1, TCL, and RIF). By specific binding affinity, it is meant that the polypeptide has a binding preference for one or more specific G-proteins. Various chimeric GAP peptide fusion products are shown graphically in FIG. 1.

A "chimeric gene" refers to a sequence of DNA in which nucleotide sequences not naturally occurring together are linked. As used to describe this aspect, the term "chimeric" requires that the amino acid sequence of the chimeric molecule include at least one stretch of amino acids (preferably stretches of 50-300, or more amino acids) from the naturally-occurring polypeptide from which it was derived. Thus, the chimeric polypeptide is a "hybrid" or "mosaic" of two or more polypeptides. By "chimeric" is meant that the polypeptide is not identical to any naturally occurring polypeptide sequence (or fragment of a natural polypeptide sequence).

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

A "clone" is a population of cells derived from a single cell or common ancestor by mitosis. A "cell line" is a derivative of a primary cell culture that is capable of stable growth in vitro for many generations.

A DNA "coding sequence" or a "nucleotide sequence encoding" a particular protein, is a DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, that depend upon binding between nucleic acids strands.

"Consensus", as used herein, refers to a nucleic acid sequence that has been re-sequenced to resolve uncalled bases, or that has been extended using XL-PCR (Perkin Elmer, Norwalk, Conn.) in the 5' and/or the 3' direction and re-sequenced, or that has been assembled from the overlapping sequences of more than one Incyte clone using the GELVIEW Fragment Assembly system (GCG, Madison, Wis.), or that has been both extended and assembled.

DNA "control sequences" refer collectively to promoter sequences, ribosome binding sites, polyadenylation signals, transcription termination sequences, upstream regulatory domains, enhancers, and the like, that collectively provide for the transcription and translation of a coding sequence in a host cell.

A "covalent bond" is defined as the formation of a sigma bond between two organic molecules. A "non-covalent bond" is meant to include all interactions other than a covalent bond. Non-covalent bonds include ionic interactions, hydrogen bonding, pi-pi bonding, hydrophobic interactions, and van der Waals interactions.

The term "cytotoxic agent" as used herein refers to a substance that inhibits or prevents the function of cells and/or causes destruction of cells. The term is intended to include radioactive isotopes, chemotherapeutic agents, and toxins such as enzymatically active toxins of bacterial, fungal, plant or animal origin, or fragments thereof.

A "deletion", as used herein, refers to a change in either amino acid or nucleotide sequence in which one or more amino acid or nucleotide residues, respectively, are absent.

The term "derivative", as used herein, refers to the chemical modification of a nucleic acid encoding GAP or the encoded GAP. Illustrative of such modifications would be replacement of hydrogen by an alkyl, acyl, or amino group. A nucleic acid derivative would encode a polypeptide, that retains essential biological characteristics of the natural molecule.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. After digestion, the reaction is electrophoresed directly on an agarose or polyacrylamide gel to isolate the desired fragment.

A "DNA construct" is a DNA molecule, or a clone of such a molecule, either single- or double-stranded that has been modified through human intervention to contain segments of DNA combined and juxtaposed in a manner that as a whole would not otherwise exist in nature.

A "double-stranded DNA molecule" refers to the polymeric form of deoxyribonucleotides (bases: adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

An "effective amount" or "therapeutically effective amount" of an active agent disclosed herein is an amount capable of modulating, to some extent, the activity of at least one GTPase within a target cell and preferably is an amount capable of modulating, to some extent, the growth or activity of a target cell. The term includes an amount capable of invoking a growth inhibitory, cytostatic and/or cytotoxic effect and/or apoptosis of the target cells. An "effective amount" may be determined empirically and in a routine manner. An "effective amount" of a polypeptide disclosed herein or an antagonist thereof, in reference to inhibition of neoplastic cell growth, tumor growth or cancer cell growth, is an amount capable of inhibiting, to some extent, the growth of target cells. The term includes an amount capable of invoking a growth inhibitory, cytostatic and/or cytotoxic effect and/or apoptosis of the target cells.

The term "encoding" refers generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence that promotes expression of the sense strand. The information is convertible using the standard, or a modified, genetic code. See, e.g., Watson et al., (1987) The Molecular Biology of the Gene (4th ed.) vols. 1&2, Benjamin, Menlo Park, Calif., herein incorporated by reference in its entirety "Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2-15 µg of the target DNA in 10 mM MgCl$_2$, 1 mM dithiothreitol, 50 mM NaCl, 10 mM Tris (pH 7.5) buffer at about 37° C. in the presence of 8 units of the Klenow fragment of DNA polymerase I and 250 µM of each of the four deoxynucleoside triphosphates. The incubation generally is terminated after 30 min. phenol and chloroform extraction and ethanol precipitation.

GTPases

A "Rho GTPase" is a small, membrane-bound, Ras-related GTP-binding protein that functions by binding and hydrolyzing GTP. Rho GTPases function as molecular switches, cycling between an inactive GDP-bound conformation and an active GTP-bound conformation and include RhoA, RhoB, RhoC, Cdc42, Rac1, Rac2, Rac3, TC10, RhoG, RhoD, Chp, WRCH1, TCL, and RIF. The terms "RhoGTPase" or "Rho GTPase protein polypeptide" refer to a protein or polypeptide sequence of a Ras-related GTP-binding protein, variants or fragments thereof obtained from any species, particularly mammalian, including bovine, ovine, porcine, murine, equine, and preferably human, from any source whether natural, synthetic, semi-synthetic, or recombinant.

GAP Proteins and Domains

A key group of regulatory molecules for the Rho GTPases is the Rho GTPase-activating proteins (GAPs). Rho GAPs preferentially recognize the GTP-bound form of a Rho GTPase and stimulate the intrinsic GTPase activity to hydrolyze the bound GTP to GDP. Rho GAPs therefore function as negative regulators or suppressors of Rho GTPase by stimulating the conversion of the Rho GTPase from the active GTP-bound form to the inactive GDP-bound form.

The term "GTPase activating protein" or "GAP", as used herein, refers to the amino acid sequences of GTPase activating proteins obtained from any species, particularly mammalian, including bovine, ovine, porcine, murine, equine, and preferably human, from any source whether natural, synthetic, semi-synthetic, or recombinant. "GAPs" refers to more than one GAP. Generally, Rho GAP proteins share an approximately 170-190 amino acid homology region, designated as the Rho GAP domain, that appears to contain the minimum structural domain necessary for GAP activity. Rho GAP proteins share 20-24% amino acid identity in this domain, however, certain specific residues are highly conserved.

A number of GAPs that are active on proteins of the Rho family have been identified (reviewed in Lamarche and Hall, TIG 10:436-440, 1994). These include p50RhoGAP (Lancaster et al., J. Biol. Chem. 269:1137-1142, 1994), Myr5 (Reinhard et al., EMBO J. 14:697-704, 1995), and p190 (Settleman et al., Nature 359:153-154, 1992) that are also active on Rac and Cdc42. Another GAP, p122-RhoGAP (Homma and Emori, EMBO J. 14:286-291, 1995) appears to be specific for Rho. In addition, rhoGAPs include p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants (Moon, S. Y. and Zheng, Y. (2003) Rho GTPase-activating proteins in cell regulation, *Trends Cell Biol.* 13, 14-23. Peck, J., Douglas, G., Wu, C. H., and Burbelo, P. D. (2002) Human RhoGAP domain-containing proteins: structure, function and evolution relationship. *FEBS Letters* 528, 27-34).

The terms "GAP polypeptide" and "GAP" as used herein and when immediately followed by a numerical designation refer to various polypeptides, wherein the complete designation (i.e., GAP/number) refers to specific polypeptide sequences as described herein. The terms "GAP/number polypeptide" and "GAP/number" wherein the term "number" is provided as an actual numerical designation as used herein encompass native sequence polypeptides and polypeptide variants (that are further defined herein). The GAP polypeptides described herein may be isolated from a variety of sources, such as from human tissue types or from another source, or prepared by recombinant or synthetic methods. The term "GAP polypeptide" refers to each individual GAP/number polypeptide disclosed herein. All disclosures in this specification that refer to the "GAP polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide-individually. The term "GAP polypeptide" also includes variants of the GAP/number polypeptides disclosed herein.

"GAP polypeptide variant" means an active GAP polypeptide as defined above or below having at least about 80% amino acid sequence identity with a full-length native sequence GAP polypeptide sequence as disclosed herein (e.g., SEQ ID NO:2; SEQ ID NO:4; SEQ ID NO:6), a GAP polypeptide sequence lacking the signal peptide as disclosed herein, an extracellular domain of a GAP polypeptide, with or without the signal peptide, as disclosed herein or any other fragment of a full-length GAP polypeptide sequence as disclosed herein. Such GAP polypeptide variants include, for instance, GAP polypeptides wherein one or more amino acid residues are added, or deleted, at the N- or C-terminus of the full-length native amino acid sequence. Ordinarily, a GAP polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence GAP polypeptide sequence as disclosed herein, a GAP polypeptide sequence lacking the signal peptide as disclosed herein, an extracellular domain of a GAP polypeptide, with or without the signal peptide, as disclosed herein or any other specifically defined fragment of a full-length GAP polypeptide sequence as disclosed herein. Ordinarily, GAP variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

Other GAP variants, can be produced with reference to the following reviews, herein incorporated by reference in their entirety: Chardin, P. *Curr Biol*. 2003 Sep. 16; 13(18); R702-4 GTPase regulation: getting a Rnd Rock and Rho inhibition; Bernads, A. *Biochim Biophys Acta*. 2003 Mar. 17; 1603(2); 47-82 GAPs galore! A survey of putative Ras superfamily GTPase activating proteins in man and *Drosophila*; Douglas, et al. *FEBS letters* 2002 Sep. 25; 528 (1-3); 27-34 Human RhoGAP domain-containing proteins: structure function and evolutionary relationships; Moon S Y, Zheng, Y. *Trends Cell Biol*. 2003 January; 13(1):13-22 Rho GTPase-activating proteins in cell regulation; Lamarche N, Hall A. *Trends Genet*. 1994 December; 10(12); 436-40 GAPs for rho-related GTPases.

The minimum structural domain necessary is the minimum amount of amino acids which are necessary to impart the inhibitory activity on the GAP domain. Thus, for example, truncations, substitutions and other minor changes may be made to the GAP domain and still provide for enough activity to produce a useful fusion protein.

GAP Variants, Homologs, Motifs, and Minimum Region Necessary for Activity

The following references and studies have identified motifs, sequence similarities, and the minimum region necessary for the activity of the GAP domain. These references and this information can be used to produce GAP variants and to identify the smallest number of amino acids within the GAP region necessary for imparting the activity of the region. Further, these references can be used to identify homologs and the regions necessary within those homologs.

For example, Bernards, et al. Biochimica Biophys acta, 1603, 2003, ppg. 47-82 (herein incorporated by reference in its entirety) discusses the crystal structure and residues that are conserved. The crystal structure of a 334 amino acid fragment of p120GAP catalytic domain revealed a fully alpha-helical domain structure. Residues that are conserved among RasGAPs are present in a central 218 residue domain that corresponds to the minimal segment of neurofibromin that retains full catalytic activity. The structure of a 333 residue GAP domain fragment of neurofibromin has also been determined, revealing a similar overall structure. A crystal structure of the RasGAP-334 complex identified that the GAPs promote Ras-GTP hydrolysis by properly aligning the catalytically important Gln61 in the switch II region of Ras and by contributing an arginine finger residue.

The 3D structures of an approximately 230 amino acid C-terminal segment representing the catalytic domain of p50PhoGAP in a complex with Rho A GDP has also been determined. The fully alpha-helical catalytic domain that is sometimes referred to as a breakpoint cluster region-homology or BH domain includes a core consisting of four bundled helices that includes most residues conserved among RhoGAPs. Similar to what was found for RasGAPs, an essential arginine residue of p50RhoGAP protrudes into the GTPase active site.

Distantly related RasGAPs and RhoGAPs include homologous arginine fingers that directly participate in catalysis. Potential arginine fingers have been identified in GAPs for most Ras superfamily members.

Examples of the motifs found in the GAPs are provided in Lamarche, et al. *TIG* December 1994, Vol. 10, No. 12 (herein incorporated by reference in its entirety). Further, the structure, function and evolutionary relationships to homologs are provided in Peck, et al. *FEBS letters*, 528, 2002, pages 27-34, and Moon, et al. *Trends in Cell Biol*. V. 13, No. 1, January 2003, both of which are herein incorporated by reference in their entirety.

As used interchangeably herein, a "GAP activity", "biological activity of GAP," or "functional activity of GAP," includes at least one activity exerted by a GAP protein, polypeptide or nucleic acid molecule on a GAP-responsive cell or tissue, or on a GAP protein substrate, as determined in vivo, or in vitro, according to standard techniques. In one embodiment, a GAP activity is a direct activity, such as an association with a GAP-target molecule. As used herein, a "target molecule" or "binding partner" is a molecule with which a GAP protein binds or interacts in nature, such that GAP-mediated function is achieved. A GAP target molecule can be a non-GAP molecule or a GAP protein or chimeric polypeptide. In an exemplary embodiment, a GAP target molecule is a GAP ligand, e.g., a GTPase. Alternatively, a GAP activity is an indirect activity, such as a cellular signaling activity mediated by interaction of the GAP protein with a GAP ligand, e.g., a GTPase. Preferably, a GAP activity is the ability to modulate the hydrolysis of GTP via, e.g., interactions with GTPase molecules.

In another embodiment, a chimeric GAP molecule is identified based on the presence of a "GAP domain" in the protein or corresponding nucleic acid molecule. As used herein, the term "GAP domain" includes a protein domain or variant or truncated domain having an amino acid sequence of from about 50 to about 300 amino acid residues. In a further embodiment, the GAP domain has about 150 amino acid residues. In a further embodiment a GAP domain has from about 120 to about 265 amino acid residues. In a further embodiment, the GAP domain has from about 140 to about 205 amino acid residues, or from about 145 to about 175 amino acids. In one embodiment the GAP domain is a RhoGAP domain. In another preferred embodiment, a GAP domain has at least about 40%, 50%, 60%, 70% 80% 90% 95%, 97%, 98%, 99%, or 100% sequence identity with a RhoGAP domain of human p190GAP (e.g., residues 1261-1431 of SEQ ID NO:2). In a further embodiment, the conserved regions have from about 40% to about 100% identity, including but not limited to: 40%, 50%, 60%, 70% 80% 90% 95%, 97%, 98%, 99%, or 100%. In a further embodiment, the nonconserved regions have from about 10% to about 100% identity, including but not limited to: 20%, 30%, 40%, 50%, 60%, 70%, 80%, 90%, and 95%.

In another embodiment, a chimeric GAP molecule is identified based on the presence of a "Cdc42GAP domain" in the protein or corresponding nucleic acid molecule. As used herein, the term "Cdc42GAP domain" includes a protein domain having an amino acid sequence of about 150 amino acid residues. Preferably, a Cdc42GAP domain includes at least about 120-265, more preferably about 140-205 amino acid residues, or about 145-175 amino acids. In another preferred embodiment, a Cdc42GAP domain has at least about 40%, 50%, 60%, 70% 80% 90% 95%, 97%, 98%, 99%, or 100% sequence identity with a Cdc42GAP domain of human or rat Cdc42GAP (e.g., residues 257-426 of SEQ ID NO:4).

In another embodiment, a chimeric GAP molecule is identified based on the presence of a "BcrGAP domain" in the protein or corresponding nucleic acid molecule. As used herein, the term "BcrGAP domain" includes a protein domain having an amino acid sequence of about 150 amino acid residues. Preferably, a BcrGAP domain includes at least about 120-265, more preferably about 140-235 amino acid residues, or about 145-195 amino acids. In another preferred embodiment, a BcrGAP domain has at least about 40%, 50%, 60%, 70% 80% 90% 95%, 97%, 98%, 99%, or 100% sequence identity with a BcrGAP domain of human or rat BcrGAP (e.g., residues 1014-1205 of SEQ ID NO:6).

In a further embodiment, the GAP domain is provided from at least one of the following protein sequences:

"GAP polynucleotide" or "GAP nucleic acid sequence" means a nucleic acid molecule that encodes an active GAP polypeptide as defined herein and that has at least about 80% nucleic acid sequence identity with a nucleotide acid sequence encoding a full-length native sequence GAP polypeptide sequence as disclosed herein, a full-length native sequence GAP polypeptide sequence lacking the signal peptide as disclosed herein, an extracellular domain of a GAP polypeptide, with or without the signal peptide, as disclosed herein or any other fragment of a full-length GAP polypeptide sequence as disclosed herein. Ordinarily, a GAP variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence GAP polypeptide sequence as disclosed herein, a full-length native sequence GAP polypeptide sequence or any other fragment of a full-length GAP polypeptide sequence as disclosed herein (e.g., SEQ ID NO:1; SEQ ID NO:3; SEQ ID NO:5). Variants do not encompass the native nucleotide sequence.

Additional Definitions and Explanations

The phrases "gene amplification" and "gene duplication" are used interchangeably and refer to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

A "gene fusion" is a DNA construction (performed in vitro or in vivo) that results in the coding sequences from one gene (the "responder") being transcribed and/or translated under the direction of the controlling sequences of another gene (the "controller"). Responder genes can be divided into two classes, reporters and effectors, with analytical or manipulative roles, respectively.

A "growth inhibitory agent" when used herein refers to a compound or composition that inhibits growth of a cell, especially cancer cell overexpressing any of the genes identified herein, either in vitro or in vivo. Thus, the growth inhibitory agent is one, that significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence that lacks even a partial degree of complementarity (e.g., less than about 30% identity); in the absence of non-specific binding, the probe will not hybridize to the second non-complementary target sequence.

A "host cell" is a cell that has been transformed, or is capable of transformation, by an exogenous DNA sequence.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration.

Administration "in combination with" one or more further therapeutic agents includes simultaneous (concurrent) and consecutive administration in any order.

An "insertion" or "addition", as used herein, refers to a change in an amino acid or nucleotide sequence resulting in the addition of one or more amino acid or nucleotide residues, respectively, as compared to the naturally occurring molecule.

An "isolated" nucleic acid is a nucleic acid, e.g., an RNA, DNA, or a mixed polymer, that is substantially separated from other DNA sequences that naturally accompany a native human sequence, e.g., ribosomes, polymerases, and many other human genome sequences. The term embraces a nucleic acid sequence that has been removed from its naturally occurring environment, and includes recombinant or cloned DNA isolates and chemically synthesized analogs or analogs biologically synthesized by heterologous systems. A substantially pure molecule includes isolated forms of the molecule. An isolated nucleic acid will generally be a homogenous composition of molecules, but will, in some embodiments, contain minor heterogeneity. This heterogeneity is typically found at the polymer ends or portions not critical to a desired biological function or activity.

"Isolated," when used to describe the various polypeptides disclosed herein, means polypeptide that has been identified and separated and/or recovered from at least one component of its natural environment. Preferably, the isolated polypeptide is free of association with substantially all contaminant components with which it is naturally associated and that substantially interfere with its activity. Contaminant components of its natural environment are materials that would typically interfere with diagnostic or therapeutic uses for the polypeptide, and may include enzymes, hormones, and other proteinaceous or non-proteinaceous solutes.

Two or more DNA coding sequences are said to be "joined" when, as a result of in-frame fusions between the DNA coding sequences or as a result of the removal of intervening sequences by normal cellular processing, the DNA coding sequences are translated into a polypeptide fusion.

The word "label" when used herein refers to a detectable compound or composition that is conjugated directly or indirectly to the peptide or nucleotide so as to generate a "labeled" entity. The label may be detectable by itself (e.g. radioisotope labels or fluorescent labels) or, in the case of an enzymatic label, may catalyze chemical alteration of a substrate compound or composition, that is detectable.

A "liposome" is a small vesicle composed of various types of lipids, phospholipids and/or surfactant that is useful for delivery of a drug (such as a GAP polypeptide) to a mammal. The components of the liposome are commonly arranged in a bilayer formation, similar to the lipid arrangement of biological membranes.

The term "mimetic", as used herein, refers to a molecule, the structure of which is developed from knowledge of the structure of GAP or portions thereof and, as such, is able to effect some or all of the actions of the molecules related to Rho proteins.

"Ligation" refers to the process of forming phosphodiester bonds between two double stranded nucleic acid fragments. Unless otherwise provided, ligation is accomplished using known buffers and conditions with T4 DNA ligase ("ligase") and approximately equimolar amounts of the DNA fragments to be ligated.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "modulate", as used herein, refers to a change or an alteration in the biological activity of at least one GTPase. Modulation may be an increase or a decrease in protein activity, a change in binding characteristics, or any other change in the biological, functional or other properties of a GTPase.

A "native sequence GAP polypeptide" comprises a polypeptide having the same amino acid sequence as the corresponding GAP polypeptide derived from nature. Such native sequence GAP polypeptides can be isolated from nature or can be produced by recombinant or synthetic means. The term "native sequence GAP polypeptide" specifically encompasses naturally-occurring truncated or secreted forms of the specific GAP polypeptide (e.g., an extracellular domain sequence), naturally-occurring variant forms (e.g., alternatively spliced forms) and naturally-occurring allelic variants of the polypeptide. In various embodiments, the native sequence GAP polypeptides disclosed herein are mature or full-length native sequence polypeptides comprising the full-length amino acids sequences shown in the accompanying figures. Start and stop codons are shown in bold font and underlined in the figures. However, while the GAP polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the GAP polypeptides.

"Nucleic acid sequence" as used herein refers to an oligonucleotide, nucleotide, or polynucleotide, and fragments or portions thereof, and to DNA or RNA of genomic or synthetic origin that may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

"Oligonucleotides" refers to either a single stranded polydeoxynucleotide or two complementary polydeoxynucleotide strands, that may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The "pathology" of cancer includes all phenomena that compromise the well-being of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Percent (%) amino acid sequence identity" with respect to the GAP polypeptide sequences identified herein is defined as the percentage of amino acid residues in a candidate sequence that are identical with the amino acid residues in the specific GAP polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST software. Those skilled in the art can determine appropriate parameters for measuring alignment, including any algorithms needed to achieve maximal alignment over the full length of the sequences being compared.

The term "polypeptide" refers to a polymer of amino acids and its equivalent and does not refer to a specific length of the product; thus, peptides, oligopeptides and proteins are included within the definition of a polypeptide. This term also does not exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring.

A "polypeptide variant" of any one of the polypeptides will have at least about 80% amino acid sequence identity, preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and most preferably at least about 99% amino acid sequence identity with a full-length native sequence as disclosed herein, such variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 300 amino acids in length, or more.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:2" encompasses the full-length human GAP and fragments thereof.

The term "prodrug" as used in this application refers to a precursor or derivative form of a pharmaceutically active substance that is less cytotoxic to tumor cells compared to the parent drug and is capable of being enzymatically activated or converted into the more active parent form. The prodrugs include, but are not limited to, phosphate-containing prodrugs, thiophosphate-containing prodrugs, sulfate-containing prodrugs, peptide-containing prodrugs, D-amino acid-modified prodrugs, glysocylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted into the more active cytotoxic free drug.

A "promoter sequence" is a DNA regulatory region capable of binding RNA polymerase in a cell and initiating transcription of a downstream (3' direction) coding sequence. The promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like. "Native" proteins or polypeptides refer to proteins or polypeptides recovered from a source occurring in nature.

"Percent (%) nucleic acid sequence identity" with respect to GAP-encoding nucleic acid sequences identified herein is defined as the percentage of nucleotides in a candidate sequence that are identical with the nucleotides in the GAP nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST software.

The term "recombinant" refers to a nucleic acid sequence, that is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so.

The term "signal peptide" refers to any peptide sequence that directs a polypeptide to which it is attached to a target cell and, preferably, directs its transport across the cell membrane. An "importation competent signal peptide sequence" is one that remains competent to translocate the attached peptide sequence across a cellular membrane.

The term "stringent conditions", as used herein, is the "stringency" that occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences. As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, that may, but does not have to, result in the regression or rejection of the tumor; and/or (7) relief, to some extent, of one or more symptoms associated with the disorder.

"Transcriptional fusions" are gene fusions in which all coding sequences are derived from the responder gene.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

"Translational fusions" are gene fusions that encode a polypeptide comprising coding information of the controller and responder genes.

"Treatment" is an intervention performed with the intention of preventing the development or altering the pathology of a disorder. Accordingly, "treatment" refers to both therapeutic treatment and prophylactic or preventative measures.

Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

"Tumor", as used herein, refers to all neoplastic cell growth and proliferation, whether malignant or benign, and all pre-cancerous and cancerous cells and tissues.

A "variant" as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "vector" is a replicon, such as a plasmid, phage, or cosmid, to which another DNA segment may be attached so as to bring about the replication of the attached segment.

DESCRIPTION OF EMBODIMENTS

One embodiment provides for novel chimeric polypeptides and nucleic acids coding for chimeric GAP proteins or polypeptides (CGP). The activities of a chimeric GAP polypeptides can be assayed, e.g., as described below in the examples or according to methods that the skilled worker would know.

One embodiment provides for chimeric polypeptides and nucleic acids coding for chimeric GAP proteins or polypeptides that are isolated fusion polypeptides comprising: a) a GAP domain peptide and b) a targeting peptide.

Preferably, the GAP domain is a peptide sequence containing the minimum structural domain necessary for GTPase activating protein activity. More preferably, the GAP is a Rho family GAP including p50RhoGAP, p190, p122-RhoGAP, p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants. Variants, GAP domains, and minimum structural domains are identified above with reference to specific GAP proteins. It is understood that, because of genetic conservation of specific domains and motifs Chimeric Peptide In one embodiment, the GAP domain peptide is a polypeptide fragment of a GAP GTPase domain from a GAP protein, wherein the fragment comprises at least 15, 20, 25, 30, 40, 50, 60, 70, 80, 90, 100, 125, 150, 170, 200, 250 or more contiguous amino acids of the amino acid sequence of a GAP protein wherein the GAP protein is a Rho family GAP including p50RhoGAP, p190, p122-RhoGAP, p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants.

In another embodiment, the targeting polypeptide is a GTPase fragment comprises at least 1, 2, 3, 4, 5, 6, 7, 8, 9, 10, 11, 12, 13, 14, 15, 16, 17, 18, 19, 20, 21, 22, 23, 24, 25, 30, or more contiguous amino acids of the C-terminus amino acid sequence of a GTPase wherein the GTPase is from the RhoGTPase family. Preferably, the C-terminus tail is from a RhoGTPase selected from the group consisting of RhoA, RhoB, RhoC, Cdc42, Rac1, Rac2, Rac3, TC10, RhoG, RhoD, Chp, WRCH1, TCL, and RIF.

In another embodiment, the GAP domain may have some short amino acid sequences added to the C and N-termini in order to provide better binding of the GAPs. Thus, in one embodiment, the GAP domain peptide is a polypeptide fragment of a GAP GTPase domain from a GAP protein, wherein the fragment comprises an amino acid sequence of the formula:

$$X_N\text{-GAP-}X_C$$

wherein "GAP" is the polypeptide fragment of a GAP GTPase domain from a GAP protein as described herein;

wherein $X_N$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40 or more contiguous amino acids of the N-terminus amino acid sequence of a GAP protein; and wherein $X_C$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more contiguous amino acids of the C-terminus amino acid sequence of a GAP protein.

Preferably $X_N$ is a polypeptide fragment wherein the fragment comprises at least 1, 2, 3, 4, 5, 6, 7, 8, 9, 10, 11, 12, 13, 14, 15, 16, 17, 18 or more contiguous amino acids of an amino acid sequence selected from the group consisting of amino acids 1-1260 of SEQ ID NO: 2, amino acids 1-256 of SEQ ID NO: 4, amino acids 1-1013 of SEQ ID NO: 6, or fragments thereof;

More preferably, $X_N$ is selected from the group consisting of amino acids 1249-1260 of SEQ ID NO: 2, amino acids 237-256 of SEQ ID NO: 4, amino acids 996-1013 of SEQ ID NO: 6, or fragments thereof.

Preferably, $X_C$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more contiguous amino acids of the amino acids 1432-1513 of SEQ ID NO:2, amino acids 427-439 of SEQ ID NO:4, amino acids 1206-1227 of SEQ ID NO:6, or fragments thereof.

More preferably, $X_C$ is selected from the group consisting of amino acids 1432-1513 of SEQ ID NO:2, amino acids 427-439 of SEQ ID NO:4, amino acids 1206-1227 of SEQ ID NO:6, or fragments thereof.

Targeting Peptide

The fusion or chimeric protein disclosed herein has a targeting peptide element which can be N-terminal to the GAP domain or alternatively C-terminal to the GAP domain. Preferably, the targeting peptide is C-terminal to the GAP domain. Generally, the targeting peptide is derived from the C-terminus amino acid sequence of a GTPase. The C-terminus amino acids sequence can be from any GTPase known to one of skill in the art, including but not limited to: the C-terminal tail of RhoGTPase, including RhoA, RhoB, RhoC, Cdc42, Rac1, Rac2, Rac3, TC10, RhoG, RhoD, Chp, WRCH1, TCL, and RIF. The targeting peptide can be any part of the C-terminus of the GTPase as long as the necessary motifs and/or domains are included such that it will still target a specific part of the cell. Such domains and motifs have been identified for a number of the GTPase family and include the membrane targeting sequences of the Rho GTPase C-terminal isoprenylation (CAAX box) and poly basic domains. In one embodiment, the C-terminal sequence of the GTPase comprises a membrane-associating isoprenylation modification. In a further embodiment, the C-terminal sequence is a lipid modified peptide. These C-terminal sequences include at least 12 amino acids, but may contain more without affecting the targeting activity of the sequence.

In another embodiment, the targeting polypeptide is a peptide fragment wherein the fragment comprises at least 1, 2, 3, 4, 5, 6, 7, 8, 9, 10, 11, 12, 13, 14, 15, 16, 17, 18 or more contiguous amino acids of the following amino acid sequences:

| | |
|---|---|
| LQARRGKKKSG---CLVL | (SEQ ID NO: 14) |
| LQKRYGSQNGCINCCKVL | (SEQ ID NO: 15) |
| LQVRKNKRRRG---CPIL | (SEQ ID NO: 16) |
| PEPKKSRRCVLL | (SEQ ID NO: 17) |
| PVKKRKRKCLLL | (SEQ ID NO: 18) |
| PTRQQKRACSLL | (SEQ ID NO: 19) |
| PVKKPGKKCTVF | (SEQ ID NO: 20) | or fragments or derivatives thereof.

More preferably, the targeting polypeptide is a targeting polypeptide fragment wherein the fragment comprises an amino acid sequence selected from the group consisting of amino acids:

| | |
|---|---|
| LQARRGKKKSG---CLVL | (SEQ ID NO: 14) |
| LQKRYGSQNGCINCCKVL | (SEQ ID NO: 15) |
| LQVRKNKRRRG---CPIL | (SEQ ID NO: 16) |
| PEPKKSRRCVLL | (SEQ ID NO: 17) |
| PVKKRKRKCLLL | (SEQ ID NO: 18) |
| PTRQQKRACSLL | (SEQ ID NO: 19) |
| PVKKPGKKCTVF | (SEQ ID NO: 20) | or fragments or derivatives thereof.

Methods of importing the biologically active chimeric peptides into intact cells are also disclosed herein. Such molecules can be engineered by forming a complex by attaching an importation competent signal peptide sequence to a selected biologically active chimeric GAP molecule and administering the complex to the cell. The complex is then imported across the cell membrane by the cell. Thus, methods are provided of importing a biologically active molecule into a cell ex vivo or in vivo comprising administering to the cell, under import conditions, a complex comprising the molecule linked to an importation competent signal peptide, thereby importing the molecule into the cell. In one embodiment, the chimeric GAP polypeptides, when linked to a signal peptide and transported into cells, induces a mobilization response in the hematopoietic stem and progenitor cells.

Suitable import conditions are exemplified herein and include cell and complex temperature between about 18° C. and about 42° C., with a preferred temperature being between about 22° C. and about 37° C. For administration to a cell in a subject, the complex, once in the subject, will of course adjust to the subject's body temperature. For ex vivo administration, the complex can be administered by any standard methods that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the complex is encapsulated, or rectal administration, particularly when the complex is in suppository form. A pharmaceutically acceptable carrier includes any material that is not biologically or otherwise undesirable, i.e., the material may be administered to an individual along with the selected complex without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like. Actual methods of preparing such dosage forms are known, or will be apparent, to those skilled in this art; for example, see Remington's Pharmaceutical Sciences.

In one embodiment, a complex comprising the selected biologically active chimeric GAP peptide linked to an importation competent signal peptide is utilized. As discussed above, the biologically active molecule can be selected from any of a variety of molecules, with its selection being dependent upon the purpose to be accomplished by importing the molecule into the selected cell.

In one embodiment, an isolated fusion polypeptide is disclosed comprising: a) a membrane-translocating peptide, b) a GAP domain peptide and c) a targeting peptide derived from the C-terminus amino acid sequence of a GTPase Generally, the membrane-translocating peptide is a peptide of about 8 to about 50 residues. Preferably, the a membrane-translocating peptide is a peptide of about 8 to about 50 residues comprising at least eight consecutive residues of SEQ ID NOs:21, 22, 23, 24, or 25. More preferably, the signal peptide is an importation competent signal peptide sequence ("membrane-translocating peptide") having about 8 to about 50 residues comprising at least eight consecutive residues of SEQ ID NOs: 21, 22, 23, 24, or 25.

An "importation competent signal peptide" or "membrane-translocating peptide", as used herein, is a sequence of amino acids generally of a length of about 8 to about 50 or more amino acid residues, many (typically about 55-60%) residues of that are hydrophobic such that they have a hydrophobic, lipid-soluble portion. Preferably, the importation competent signal peptide is a sequence of amino acids generally of a length of about 8 to about 24 or more amino acid residues. The hydrophobic portion is a common, major motif of the signal peptide, and it is often a central part of the signal peptide of protein secreted from cells. A signal peptide is a peptide capable of penetrating through the cell membrane to allow the export of cellular proteins. The signal peptides are also "importation competent," i.e., capable of penetrating through the cell membrane from outside the cell to the interior of the cell. The amino acid residues can be mutated and/or modified (i.e., to form mimetics) so long as the modifications do not affect the translocation-mediating function of the peptide. Thus the word "peptide" includes mimetics and the word "amino acid" includes modified amino acids, as used herein, unusual amino acids, and D-form amino acids. All importation competent signal peptides encompassed herein have the function of mediating translocation across a cell membrane from outside the cell to the interior of the cell. Such importation competent signal peptides could potentially be modified such that they lose the ability to export a protein but maintain the ability to import molecules into the cell. A putative signal peptide can easily be tested for this importation activity following the teachings provided herein, including testing for specificity for any selected cell type.

Chimeric GAP peptides with an importation competent signal peptide sequence attached and their use in mediating membrane-translocation and import of a polypeptide, protein domain, or full-length protein into a cell are disclosed herein. These importation competent signal peptide sequences can comprise 8-24 amino acids for protein import and also provide for a DNA sequence encoding this 8 to 24-amino acid peptide to construct a plasmid expression vector for genetically engineering proteins with cell membrane permeability by expressing the 8-24 amino acid importation competent signal peptide sequence as a fusion with a target protein for import into the cell. In a further embodiment, the membrane translocating or importation competent domain includes a lipid modified peptide and is a peptide of about 8 to about 50 residues comprising at least 8 consecutive residues of an amino acid sequence from SEQ ID Nos: 21, 22, 23, 24, 25, and fragments and variants thereof. However, the variants and fragments still contain the minimum sequence necessary for translocation. In a further embodiment, the lipid modified peptide has from about 8 to about 24 residues. In a further embodiment, at least 55% of the residues are hydrophobic such that they have a hydrophobic, lipid soluble portion.

In the preferred embodiment, the amino acid sequence of the importation competent signal peptide sequence is selected from the group consisting of Pro-Thr-Arg-Gln-Gln-Lys-Arg-Pro-Cys-Ser-Leu-Leu (SEQ ID NO:21), Pro-Gln-Pro-Thr-Arg-Gln-Gln-Lys-Arg-Pro-Cys-Ser-Leu-Leu, (SEQ ID NO:22), Gly-Arg-Arg-Arg-Arg-Arg-Arg-Arg-Gly-Thr-Arg-Gln-Gln-Lys-Arg-Pro, (SEQ ID NO:23), Gly-Arg-Arg-Arg-Arg-Arg-Arg-Arg-Gly-Arg-Pro-Arg-Gln-Thr-Gln-Lys, (SEQ ID NO:24), and Gly-Arg-Arg-Arg-Arg-Arg-Arg-Arg-Gly-Thr-Arg-Gln-Gln-Lys-Arg-Pro-Cys-Leu-Leu (SEQ ID NO:25). As used herein, however, the term "peptide" is intended to include mimetics and the term "amino acid" is intended to include D-form amino acids and modified amino acids. These substitutions may be made by someone of skill in the art, using the known structural similarities between the molecules. The membrane translocating sequence may be located immediately adjacent to, or some distance from, the cargo protein as produced by the recombinant nucleotide vector herein. Therefore, the amino acid sequence is also intended to include any peptide or protein sequence that may include additional amino acids either N-terminal or C-terminal to the listed sequence, or both. Alternative sequences are intended to include alternative amino acids, as well as additional C-terminal or N-terminal amino acids.

Signal peptides can be selected, for example, from the SIGPEP database, that also lists the origin of the signal peptide. When a specific cell type is to be targeted, such as hematopoietic cells, a signal peptide used by that cell type can be chosen. Additionally, signal peptides endogenous to the cell type can be chosen for importing biologically active molecules into that cell type. And again, any selected signal peptide can be routinely tested for the ability to translocate across the cell membrane of any given cell type according to the teachings herein. Specifically, the signal peptide of choice can be conjugated to a biologically active molecule, e.g., a functional domain of a cellular protein or a reporter construct, and administered to a cell, and the cell is subsequently screened for the presence of the active molecule. Signal peptides are known in the art, e.g., U.S. Pat. Nos. 6,573,068; 6,548,633; 6,495,518; 6,451,601; 6,432,680; 6,312,922; 6,248,558; 6,245,739; 6,043,339; 5,807,746; 5,464,822, incorporated herein by reference. Any signal peptide, however, capable of translocating across the cell membrane into the interior of the selected target cell can be used.

The presence of modified amino acids in the signal peptide can additionally be useful for rendering a complex, wherein the biologically active molecule is a peptide, polypeptide or protein, more resistant to peptidases in the subject Thus these signal peptides can allow for more effective treatment by allowing more peptides to reach their target and by prolonging the life of the peptide before it is degraded. Additionally, one can modify the amino acid sequence of the signal peptide to alter any proteolytic cleavage site present in the original signal sequence for removing the signal sequence. Cleavage sites are characterized by small, positively charged amino acids with no side chains.

By "linked" as used herein is meant that the biologically active molecule is associated with the signal peptide in such a manner that when the signal peptide crosses the cell membrane, the molecule is also imported across the cell membrane. Examples of such means of linking include (1) when the molecule is a peptide, the signal peptide (and a nuclear localization peptide, if desired) can be linked by a peptide bond, i.e., the two peptides can be synthesized contiguously; (2) when the molecule is a polypeptide or a protein, the signal peptide (and a nuclear localization peptide, if desired) can be linked to the molecule by a peptide bond or by a non-peptide covalent bond (such as conjugating a signal peptide to a protein with a crosslinking reagent); (3) for molecules that have a negative charge, such as nucleic acids, the molecule and the signal peptide (and a nuclear localization peptide, if desired) can be joined by charge-association between the negatively-charged molecule and the positively-charged amino acids in the peptide or by other types of association between nucleic acids and amino acids; (4) chemical ligation methods can be employed to create a covalent bond between the carboxy-terminal amino acid of the signal peptide (and a nuclear localization peptide, if desired) and the molecule. Methods (1) and (2) are typically preferred.

Examples of method (1) are shown below wherein a peptide is synthesized, by standard means known in the art that contains, in linear order from the amino-terminal end, a signal peptide sequence, an optional spacer amino acid region, and a biologically active amino acid sequence, e.g., the chimeric GAP peptide. Such a peptide could also be produced through recombinant DNA techniques, expressed from a recombinant construct encoding the above-described amino acids to create the peptide.

For method (2), either a peptide bond, as above, can be utilized or a non-peptide covalent bond can be used to link the signal peptide with the biologically active polypeptide or protein. This non-peptide covalent bond can be formed by methods standard in the art, such as by conjugating the signal peptide to the polypeptide or protein via a crosslinking reagent, for example, glutaraldehyde. Such methods are standard in the art. For method (3) the molecules can simply be mixed with the signal peptide and thus allowed to associate. These methods are performed in the same manner as association of nucleic acids with cationic liposomes. Alternatively, covalent (thioester) bonds can be formed between nucleic acids and peptides. Such methods are standard in the art.

For method (4), standard chemical ligation methods, such as using chemical crosslinkers interacting with the carboxy-terminal amino acid of the signal peptide, can be utilized. Such methods are standard in the art and can readily be performed to link the carboxy terminal end of the signal peptide to any selected biologically active molecule.

The complex that is administered to a subject can further comprise a liposome. Cationic and anionic liposomes are contemplated herein, as well as liposomes having neutral lipids. Cationic liposomes can be complexed with the signal peptide and a negatively-charged biologically active molecule by mixing these components and allowing them to charge-associate. Cationic liposomes are particularly useful when the biologically active molecule is a nucleic acid because of the nucleic acid's negative charge. Examples of cationic liposomes include lipofectin, lipofectamine, lipofectace and DOTAP. Anionic liposomes generally are utilized to encase within the liposome the substances to be delivered to the cell. Procedures for forming cationic liposomes encasing substances are standard in the art and can readily be utilized herein by one of ordinary skill in the art to encase the complex.

Any selected cell into which import of a biologically active molecule would be useful can be targeted by this method, as long as there is a means to bring the complex in contact with the selected cell. Cells can be within a tissue or organ, for example, supplied by a blood vessel into which the complex is administered. Additionally, the cell can be targeted by, for example, inhalation of the molecule linked to the peptide to target the lung epithelium. Some examples of cells that can be targeted by this inventive method include fibroblasts, epithelial cells, endothelial cells, blood cells and tumor cells, among many. In addition, the complex can be administered directly to a tissue site in the body. As discussed above, the signal peptide utilized can be chosen from signal peptides known to be utilized by the selected target cell, or a desired signal peptide can be tested for importing ability given the teachings herein. Generally, however, all signal peptides have the common ability to cross cell membranes due, at least in part, to their hydrophobic character. Thus, in general, a membrane-permeable signal peptide can be designed and used for any cell type, since all eukaryotic cell membranes have a similar lipid bilayer.

One particularly useful example is to import a chimeric peptide into hematopoietic cells, thereby allowing the stem cells to be mobilized by the subject. A complex comprising a biologically active molecule linked to an importation competent signal peptide and to a nuclear localization peptide is also provided herein.

One embodiment is a complex comprising an importation competent signal peptide linked to biologically active molecule selected from the group consisting of a nucleic acid, a carbohydrate, a lipid, a glycolipid and a therapeutic agent. This complex can further comprise a liposome. These complexes can be formed as described above. Liposomes can be selected as described above. The complex can be placed in a pharmaceutically acceptable carrier.

Another aspect features isolated or recombinant chimeric GAP proteins and polypeptides. In preferred embodiments, the isolated chimeric GAP includes at least one or more of the following domains: a RhoGAP domain, a membrane-targeting and/or membrane-translocation domain.

In a preferred embodiment, the chimeric GAP has an amino acid sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to the amino acid sequence selected from the group consisting of SEQ ID NO:2, SEQ ID NO:4, and SEQ ID NO:6 and includes at least one or more of the GAP domains. In another preferred embodiment, the chimeric GAP modulates GTPase activity, and includes at least one or more GAP domain.

In yet another preferred embodiment, the chimeric GAP is encoded by a nucleic acid molecule having a nucleotide sequence that hybridizes under stringent hybridization conditions to a nucleic acid molecule comprising the nucleotide sequence selected from the group consisting of SEQ ID NO:2, SEQ ID NO:4, and SEQ ID NO:6 and includes at least one or more GAP domain.

In another embodiment, fragments of the protein are provided having the amino acid sequence of SEQ ID NO:2, SEQ ID NO:4, or SEQ ID NO:6 wherein the fragment comprises at least 15, 20, 30, 40, 50, 60, 70, 80, 90, 100, 125, 150, 175, 200, 250 amino acids (e.g., contiguous amino acids) of an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13. In another embodiment, the protein has the amino acid sequence of SEQ ID NO:7, SEQ ID NO:8, SEQ ID NO:9, SEQ ID NO:10, SEQ ID NO:11, SEQ ID NO:12, or SEQ ID NO:13.

In another embodiment, an isolated chimeric GAP is featured that is encoded by a nucleic acid molecule consisting of a nucleotide sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to a nucleotide sequence selected from the group consisting of SEQ ID NO:1, SEQ ID NO:3, or SEQ ID NO:5, or a complement thereof. An isolated chimeric protein is disclosed that is encoded by a nucleic acid molecule consisting of a nucleotide sequence that hybridizes under stringent hybridization conditions to a nucleic acid molecule comprising a nucleotide sequence selected from the group consisting of SEQ ID NO:1, SEQ ID NO:3, or SEQ ID NO:5, or a complement thereof.

In another preferred embodiment, a chimeric GAP protein can be tested for an activity including, but not limited to: (1) interaction with a non-GAP protein molecule, e.g., a GTPase or a GAP ligand or substrate; (2) modulate a GAP-dependent signal transduction pathway; (3) modulate Rho GTPase-dependant signal transduction; (4) modulate Rho GTP hydrolysis activity; (5) modulate levels of GTP/GDP bound to a Rho protein.

The chimeric GAP proteins or biologically active portions thereof can be incorporated into pharmaceutical compositions, that optionally include pharmaceutically acceptable carriers.

In another aspect, a method is provided for modulating GTPase activity comprising contacting a cell with an chimeric GAP peptide that modulates GTPase activity such that GTPase activity in the cell is modulated. In one embodiment, the active compound inhibits GTPase activity. In another embodiment, the active compound stimulates GTPase activity. In another embodiment, the active compound modulates expression of GTPase by modulating transcription of a gene or translation of an mRNA. In yet another embodiment, the active compound is a nucleic acid molecule having a nucleotide sequence that is antisense to the coding strand of an mRNA or a GAP gene.

In one embodiment, the methods are used to treat a subject having a disorder characterized by aberrant or unwanted GAP protein or nucleic acid expression or activity by administering an active compound that is a GTPase modulator to the subject. In one embodiment, the GTPase modulator is a chimeric GAP protein. In one embodiment, the GTPase modulator is at least two chimeric GAP proteins, that modulate the activity of different GTPases. In another embodiment the GTPase modulator is a chimeric GAP nucleic acid molecule. In yet another embodiment, the GTPase modulator comprises one or more additional agents selected from the group consisting of a peptide, peptidomimetic, or other small molecule. In a preferred embodiment, the disorder characterized by aberrant or unwanted protein or nucleic acid expression is a GTP hydrolysis-related disorder, such as atherosclerosis, hypertension, faciogenital dysplasia, oncogenesis and metastasis, heart disease, Alzheimer's disease, cystic fibrosis and viral infection.

In another preferred embodiment, the nucleic acid molecule includes a fragment of at least 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, or more nucleotides (e.g., contiguous nucleotides) of a nucleotide sequence selected from the group consisting of SEQ ID NO:1, SEQ ID NO:3, and SEQ ID NO:5, or a complement thereof.

In another embodiment, a chimeric GAP nucleic acid molecule includes a nucleotide sequence encoding a protein having an amino acid sequence sufficiently identical to the amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13.

In a preferred embodiment, a chimeric GAP nucleic acid molecule includes a nucleotide sequence encoding a protein having an amino acid sequence at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to the entire length of an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13.

In other preferred embodiments, the nucleic acid molecule encodes a variant of a polypeptide comprising an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13., wherein the nucleic acid molecule hybridizes to a nucleotide sequence selected from the group consisting of amino acid sequence selected from the group consisting of SEQ ID NO:1, SEQ ID NO:3, and SEQ ID NO:5, or a complement thereof under stringent conditions.

Another aspect provides a vector comprising a chimeric GAP nucleic acid molecule. In certain embodiments, the vector is a recombinant expression vector. In another embodiment, a host cell is provided containing a vector. In yet another embodiment, a host cell is provided containing a nucleic acid molecule. In a further embodiment a method for producing a protein is provided by culturing a host cell in a suitable medium, e.g., a mammalian host cell such as a non-human mammalian cell, of the invention containing a recombinant expression vector, such that the protein is produced.

A further embodiment is polypeptide fragments of chimeric GAP polypeptides. The fragments are preferably biologically-active. By biologically-active, it is meant that the polypeptide fragment possesses an activity in a living system or with components of a living system. Biological-activities include: a specific binding affinity for G-proteins, in particular RhoA, RhoB, RhoC, Cdc42, Rac1, Rac2, Rac3, or acting as an agonist or antagonist of Rho GTPase activity. Such activities can be assayed routinely, e.g., according to the methods described above and below. Various fragments can be prepared.

Such a chimeric polypeptide can be prepared according to various methods, including, chemical, synthetic, quasi-synthetic, and/or recombinant methods. A chimeric nucleic acid coding for a chimeric polypeptide can contain the various domains or desired polypeptides in a continuous or interrupted open reading frame, e.g., containing introns, splice sites, enhancers, etc.

The chimeric nucleic acid can be produced according to various methods. See, e.g., U.S. Pat. No. 5,439,819. A domain or desired polypeptide can possess any desired property, including, a biological function such as catalytic, signaling, growth promoting, cellular targeting, etc., a structural function such as hydrophobic, hydrophilic, membrane-spanning, etc., receptor-ligand functions, and/or detectable functions, e.g., combined with enzyme, fluorescent polypeptide, green fluorescent protein GFP.

A polypeptide disclosed herein can be produced in an expression system, e.g., in vivo, in vitro, cell-free, recombinant, cell fusion, etc.,. Modifications to the polypeptide imparted by such system include, glycosylation, amino acid substitution (e.g., by differing codon usage), polypeptide processing such as digestion, cleavage, endopeptidase or exopeptidase activity, attachment of chemical moieties, including lipids, phosphates, etc. For example, some cell lines can remove the terminal methionine from an expressed polypeptide.

A polypeptide such as those disclosed herein can be recovered from natural sources, transformed host cells (culture medium or cells) according to the usual methods, including, ammonium sulfate or ethanol precipitation, acid extraction, anion or cation exchange chromatography, phosphocellulose chromatography, hydrophobic interaction chromatography, hydroxyapatite chromatography and lectin chromatography. It may be useful to have low concentrations (approximately 0.1-5 mM) of calcium ion present during purification (Price, et al., J. Biol. Chem., 244:917 (1969)). Protein refolding steps can be used, as necessary, in completing the configuration of the mature protein. Finally, high performance liquid chromatography (HPLC) can be employed for final purification steps. A nucleic acid comprising a nucleotide sequence coding for a polypeptide as disclosed herein can include only coding sequence of chimeric GAP; coding sequence of chimeric GAP and additional coding sequence (e.g., sequences coding for leader, secretory, targeting, enzymatic, fluorescent or other diagnostic peptides), coding sequence of chimeric GAP and non-coding sequences, e.g., untranslated sequences at either a 5' or 3' end, or dispersed in the coding sequence, e.g., introns. A nucleic acid comprising a nucleotide sequence coding without interruption for a chimeric GAP polypeptide means that the nucleotide sequence contains an amino acid coding sequence for a chimeric GAP polypeptide, with no non-coding nucleotides interrupting or intervening in the coding sequence, e.g., absent intron(s). Such a nucleotide sequence can also be described as contiguous.

A nucleic acid as disclosed herein also can comprise an expression control sequence operably linked to a nucleic acid as described above. The phrase "expression control sequence" means a nucleic acid sequence that regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, the promoter drives expression of the coding sequence. Expression control sequences can be heterologous or endogenous to the normal gene.

A nucleic acid as disclosed herein can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc.

In one embodiment, a nucleic acid or polypeptide can comprise one or more differences in the nucleotide or amino acid sequence. Changes or modifications to the nucleotide and/or amino acid sequence can be accomplished by any method available, including directed or random mutagenesis. A nucleotide sequence coding for a chimeric GAP polypeptide can contain codons found in a naturally-occurring gene, transcript, or cDNA or it can contain degenerate codons coding for the same amino acid sequences.

Modifications to a chimeric GAP sequence, e.g., mutations, can also be prepared based on homology searching from gene data banks, e.g., GenBank, EMBL. Sequence homology searching can be accomplished using various methods, including algorithms described in the BLAST family of computer programs, the Smith-Waterman algorithm, etc.

A nucleic acid as disclosed herein can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide, phosphorothioate, phosphoramidate, methylphosphonate, carbamate, etc., depending on the desired purpose, e.g., resistance to nucleases, such as RNase H, improved in vivo stability, etc. See, e.g., U.S. Pat. No. 5,378,825.

Various modifications can be made to the nucleic acids, such as attaching detectable markers (avidin, biotin, radioactive elements), moieties that improve hybridization, detection, or stability. The nucleic acids can also be attached to solid supports, e.g., nitrocellulose, nylon, agarose, diazotized cellulose, latex solid microspheres, polyacrylamides, etc., according to a desired method. See, e.g., U.S. Pat. Nos. 5,470,967, 5,476,925, 5,478,893.

A nucleic acid as disclosed herein can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for the nucleic acid. Effective conditions includes any culture conditions that are suitable for achieving production of the polypeptide by the host cell, including effective temperatures, pH, medias, additives to the media in which the host cell is cultured (e.g., additives that amplify or induce expression such as butyrate, or methotrexate if the coding nucleic acid is adjacent to a dhfr gene), cyclohexamide, cell densities, culture dishes, etc. A nucleic acid can be introduced into the cell by any effective method including, e.g., calcium phosphate precipitation, electroporation, injection, DEAE-Dextran mediated transfection, fusion with liposomes, and viral transfection. A cell into which a nucleic acid has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells, e.g., COS-7, CHO, HeLa, LTK, NIH 3T3, Rat 1 fibroblasts, yeast, insect cells, such as Sf9 (*S. frugipeda*) and *Drosophila*, bacteria, such as *E. coli, Streptococcus, bacillus*, yeast, fungal cells, plants, embryonic stem cells (e.g., mammalian, such as mouse or human), cancer or tumor cells. Sf9 expression can be accomplished in analogy to Graziani et al., Oncogene, 7:229-235, 1992. Expression control sequences are similarly selected for host compatibility and a desired purpose, e.g., high copy number, high amounts, induction, amplification, controlled expression. Other sequences that can be employed include enhancers such as from SV40, CMV, inducible promoters, cell-type specific elements, or sequences that allow selective or specific cell expression.

In addition to a chimeric GAP nucleic acid, another gene of interest can be introduced into the same host for purposes of, e.g., modulating expression chimeric GAP, elucidating chimeric GAP function or that of the gene of interest. Genes of interest include other oncogenes, genes involved in the cell cycle, etc. Such genes can be the normal gene, or a variation, e.g., a mutation, chimera, polymorphism, etc.

The modulation of GTPase activity by a chimeric GAP, or derivatives thereof, can be measured according to various known procedures, e.g., Eva and Aaronson, Nature, 316:273-275, 1985; Hart et al., J. Biol. Chem., 269:62-65, 1994. A compound can be added at any time during the method to determine its effect on the GTPase activity of chimeric GAP. Various cell lines can also be used.

Other assays for GTPase-mediated signal transduction can be accomplished according in analogy to procedures known in the art, e.g., as described in U.S. Pat. Nos. 5,141,851; 5,420,334; 5,436,128; and 5,482,954. In addition, peptides that inhibit the interaction, e.g., binding, between chimeric GAP and a G-protein, such as RhoA, can be identified and prepared according to EP 496 162.

GAP molecules play a role in GTP hydrolysis and regulation of GTP/GDP levels. As used herein, the term "GTP hydrolysis" includes the dephosphorylation of GTP, resulting in the formation of GDP or other forms of guanine. GTP hydrolysis is mediated by GTPases, e.g., Rho-GTPases, ras-GTPases, rac-GTPases, and rab-GTPases. As used herein, the term "regulation of GTP/GDP levels" includes cellular mechanisms involved in regulating and influencing the levels, e.g., intracellular levels, of GTP and GDP. Such mechanisms include the hydrolysis of GTP to GDP (GTP hydrolysis) in response to biological cues, e.g., by a GTPase. The maintenance of GTP/GDP levels is particularly important for a cell's signaling needs. Thus, the GAP molecules, by participating in GTP hydrolysis and regulation of GTP/GDP levels, may modulate GTP hydrolysis and GTP/GDP levels and provide novel diagnostic targets and therapeutic agents to control GTP hydrolysis-related disorders.

As used herein, the term "GTP hydrolysis-related disorders" includes disorders, diseases, or conditions that are characterized by aberrant, e.g., upregulated or downregulated, GTP hydrolysis and/or aberrant, e.g., unregulated or downregulated, GTP and/or GDP levels. Examples of such disorders may include cardiovascular disorders, e.g., arteriosclerosis, ischemia reperchimeric injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia.

Other examples of GTP hydrolysis-related disorders include disorders of the central nervous system, e.g., cystic fibrosis, type 1 neurofibromatosis, cognitive and neurodegenerative disorders, examples of that include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of that is incorporated herein by reference in its entirety.

Still other examples of GTP hydrolysis-related disorders include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics that differ from that of other cells, or by which a cell moves closer to or further from a particular location or stimulus. Such disorders include cancer, e.g., carcinoma, sarcoma, or leukemia; tumor angiogenesis and metastasis; skeletal dysplasia; hepatic disorders; and hematopoietic and/or myeloproliferative disorders.

Still other examples of GTP hydrolysis-related disorders include disorders of the immune system, such as Wiskott-Aldrich syndrome, viral infection, autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency. Other examples of GTP hydrolysis-related disorders include congenital malformalities, including facio-genital dysplasia; and skin disorders, including microphthalmia with linear skin defects syndrome.

The nucleic acid molecules, proteins, and derivative described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a chimeric GAP protein has one or more of the following activities: (1) it interacts with a non-GAP protein molecule, e.g., a GTPase or a GAP ligand; (2) it modulated a GAP-dependent signal transduction pathway; (3) it modulates GTP/GDP levels; and (4) it modulates GTPase signaling mechanisms, and, thus, can be used to, for example, (1) modulate the interaction with a non-GAP protein molecule, e.g., a GTPase; (2) activate a GAP-dependent signal transduction pathway; (3) modulate GTP/GDP levels; and (4) modulate GTPase signaling mechanisms.

The isolated nucleic acid molecules encoding chimeric GAP proteins or fusion proteins can be used, for example, to express chimeric GAP protein and to modulate GAP activity, as described further below. The chimeric GAP proteins can be used to treat disorders characterized by insufficient or excessive production of a GAP ligand or substrate or production of GAP inhibitors. In addition, the chimeric GAP proteins can be used to screen for naturally occurring GAP ligands or substrates to screen for drugs or compounds that modulate GAP activity, as well as to treat disorders characterized by insufficient or excessive production of GAP protein or production of GAP protein forms that have decreased, aberrant or unwanted activity compared to GAP wild type protein (e.g., GTP hydrolysis-related disorders and/or disorders related to GTP/GDP levels).

A further embodiment provides for both prophylactic and therapeutic methods of treating a subject at risk of (or susceptible to) a disorder or having a disorder associated with aberrant or unwanted GAP expression or activity, e.g., a GTP hydrolysis-related disorder.

In one aspect, a method is provided for preventing in a subject, a disease or condition associated with an aberrant or unwanted GAP expression or activity, by administering to the subject a chimeric GAP or an agent, that modulates GAP expression or at least one GAP activity. Subjects at risk for a disease that is caused or contributed to by aberrant or unwanted GAP expression or activity can be identified by, for example, any or a combination of diagnostic or prognostic assays as described herein. Administration of a prophylactic agent can occur prior to the manifestation of symptoms characteristic of the GAP aberrancy, such that a disease or disorder is prevented or, alternatively, delayed in its progression. Depending on the type of GAP aberrancy, for example, a GAP, GAP agonist or GAP antagonist agent can be used for treating the subject. The appropriate agent can be determined based on screening assays described herein.

Another aspect pertains to methods of modulating GAP expression or activity for therapeutic purposes. Accordingly, in an exemplary embodiment, the modulatory method involves contacting a cell with a GAP or active compound that modulates one or more of the activities of GAP protein activity associated with the cell. An active compound that modulates GAP protein activity can be an agent as described herein, such as a nucleic acid or a protein, a naturally-occurring target molecule of a GAP protein (e.g., a GAP ligand or substrate), a GAP agonist or antagonist, a peptidomimetic of a GAP agonist or antagonist, or other small molecule. In one embodiment, the active compound stimulates one or more GAP activities. Examples of such stimulatory active compounds include active GAP protein and a nucleic acid molecule encoding GAP that has been introduced into the cell. In another embodiment, the active compound inhibits one or more GAP activities. Examples of such inhibitory active compounds include antisense GAP nucleic acid molecules, anti-GAP antibodies, and GAP inhibitors. These modulatory methods can be performed in vitro (e.g., by culturing the cell with the active compound) or, alternatively, in vivo (e.g., by administering the active compound to a subject). As such, methods of treating an individual afflicted with a disease or disorder characterized by aberrant or unwanted expression or activity of a GAP protein or nucleic acid molecule such as a GTP hydrolysis-related disorder are provided. In one embodiment, the method involves administering an active compound (e.g., an active compound identified by a screening assay described herein), or combination of active compounds that modulates (e.g., upregulates or downregulates) GAP expression or activity. In another embodiment, the method involves administering a chimeric GAP protein or nucleic acid molecule as therapy to compensate for reduced, aberrant, or unwanted GAP expression or activity.

Stimulation of GAP activity is desirable in situations in which GAP is abnormally downregulated and/or in which increased GAP activity is likely to have a beneficial effect Likewise, inhibition of GAP activity is desirable in situations in which GAP is abnormally upregulated and/or in which decreased GAP activity is likely to have a beneficial effect.

The practice herein employs, unless otherwise indicated, conventional techniques of synthetic organic chemistry, protein chemistry, molecular biology, microbiology, and recombinant DNA technology, which are well within the skill of the art. Such techniques are explained fully in the literature.

In preferred embodiments, the chimeric GAP peptide is water soluble; or is soluble in a physiological fluid, preferably, one that is at physiological pH, for example, blood plasma.

By "derived from" is meant having an amino acid sequence identical or substantially identical to the sequence of, as used herein, a vascular-associated protein. By "substantially identical to" is meant having an amino acid sequence that differs only by conservative amino acid substitutions or by non-conservative amino acid substitutions, deletions, or insertions located at positions that do not destroy the biological activity of the peptide.

It is possible to design any number of peptide analogues, having different amino acid sequences, provided that the local charge distribution (and overall net charge) and secondary structure, and hence the biological activity is maintained. Such peptide analogues will generally differ from the native protein sequences by conservative amino acid substitutions (e.g., substitution of Leu for Val, or Arg for Lys, etc.) well known to those skilled in the art of biochemistry.

The peptides, once designed, can be synthesized by any of a number of established procedures, including, e.g., the expression of a recombinant DNA encoding that peptide in an appropriate host cell. Alternatively, these peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. The peptides so synthesized are then labeled with a reagent that enables the monitoring of the peptide after its administration to a patient.

As used herein, the term "substantially corresponds" means a peptide amino acid sequence having approximately 70% homology in amino acid sequence to a chimeric GAP peptide.

The term "chemical derivative" is meant to include any peptide derived from a peptide as disclosed herein and in which one or more amino acids have been chemically derivatized by reaction of one or more functional side groups of the amino acid residues present in the peptide. Thus, a "chemical derivative" as used herein is a peptide that is derived from the peptides identified herein by one or more chemical steps. Examples of derivatized molecules include molecules where free amino groups have been derivatized to form amine hydrochlorides, p-toluene sulfonyl groups, carbobenzoxy groups, t-butyloxycarbonyl groups, thiourethane-type derivatives, trifluoroacetyl groups, chloroacetyl groups or formyl groups. Free carboxyl groups may be derivatized to form salts, methyl and ethyl esters or other types of esters or hydrazides.

Free hydroxyl groups may be derivatized to form 0-acyl or 0-alkyl derivatives. The imidazole nitrogen of histidine may be derivatized to form N-im-benzylhistidine. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "fragment" refers to any subject peptide having an amino acid sequence shorter than that of any peptide described herein and which fragment retains the GTPase modulating properties as the subject peptides. The peptides homologues and analogs thereof may be synthesized by a number of known techniques. For example, the peptides may be prepared using the solid-phase synthetic technique or other peptide synthesis techniques well known to those skilled in the art. The peptides of the present invention might also be prepared by chemical or enzymatic cleavage from larger portions of the chimeric GAP peptide.

Additionally, the peptides may also be prepared by recombinant DNA techniques. For most of the amino acids used to build proteins, more than one coding nucleotide triplet (codon) can code for a particular amino acid residue. This property of the genetic code is known as redundancy. Therefore, a number of different nucleotide sequences may code for a particular subject eating suppressant peptide. A further embodiment also contemplates a deoxyribonucleic acid (DNA) molecule or segment that defines a gene coding for, i.e., capable of expressing, a subject polypeptide or a subject chimeric polypeptide from which a polypeptide may be enzymatically or chemically cleaved.

DNA molecules that encode the subject peptides can be synthesized by chemical techniques, for example, the phosphotriester method of Matteuccie et al., Chem. Soc. 103:3185 (1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

A further embodiment provides DNA molecules encoding the chimeric proteins. The DNA construct generally comprises a transcriptional promoter sequence followed downstream by and in proper reading frame with a DNA sequence encoding a chimeric protein, and a transcriptional terminator.

The DNA compositions may be derived from genomic DNA or cDNA, prepared by synthesis or may be a hybrid of the various combinations. Recombinant nucleic acids comprising sequences otherwise not naturally occurring are also provided. An isolated DNA sequence includes any sequence that has been obtained by primer or hybridization reactions or subjected to treatment with restriction enzymes or the like.

Novel DNA sequences, such DNA sequences as parts of expression cassettes and vectors, as well as their presence in cells are provided, where the novel sequences comprise domains that do not naturally exist together.

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene that has a high level of expression. Alternatively, promoters from mammalian expression products, such as actin, collagen, myosin, etc., may be employed. Transcriptional initiation regulatory signals may be selected that allow for repression or activation, so that expression of the genes can be modulated. Of interest are regulatory signals that are temperature-sensitive so that by varying the temperature, expression can be repressed or initiated, or that are subject to chemical regulation, e.g., metabolite.

As is widely known, translation of eucaryotic mRNA is initiated at the codon, that encodes the first methionine. For this reason, it is preferable to ensure that the linkage between a eucaryotic promoter and a DNA sequence that encodes the desired chimeric protein molecule does not contain any intervening codons that are capable of encoding a methionine (i.e., AUG). The presence of such codons results either in the formation of a different fusion protein (if the AUG codon is in the same reading frame as the desired chimeric protein molecule encoding DNA sequence) or a frame-shift mutation (if the AUG codon is not in the same reading frame as the desired chimeric protein molecule encoding sequence).

A wide variety of promoters have been described in the literature, that are constitutive or inducible, where induction may be associated with a specific cell type or a specific level of maturation. Alternatively, a number of viral promoters are known that can also be used. Promoters of interest include, but are not limited to, the beta-actin promoter, SV40 early and late promoters, immunoglobulin promoter, human cytomegalovirus promoter, the metallothionine promoter and the Friend spleen focus-forming virus promoter. The promoters may or may not be associated with enhancers, where the enhancers may be naturally associated with the particular promoter or associated with a different promoter.

The sequence of the open reading frame may be obtained from genomic DNA or cDNA, or may be synthesized, or may comprise combinations thereof. Depending upon the size of the genomic DNA and the number of introns, one may wish to use cDNA or a combination thereof. In many instances, it is found that introns stabilize the mRNA. Also, one may provide for non-coding regions that stabilize the mRNA.

The desired chimeric protein molecule encoding sequence and an operably linked promoter may be introduced into a recipient cell as a non-replicating DNA (or RNA) molecule, that may either be a linear molecule or, more preferably, a closed covalent circular molecule. Since such molecules are incapable of autonomous replication, the expression of the desired chimeric protein molecule may occur through the transient expression of the introduced sequence. Alternatively, permanent expression may occur through the integration of the introduced sequence into the host chromosome.

Using standard techniques of recombinant DNA technology, vectors for transforming suitable host cells can be constructed that contain cDNA sequences corresponding to the structural gene for the chimeric GAP fusion protein. Suitable vectors, for example, are plasmid vectors that include control and regulatory sequences operably linked to the cDNA sequence coding for the chimeric GAP protein.

DNA or cDNA molecules that encode the chimeric protein molecule can be operably linked into an expression vector and introduced into a host cell to enable the expression of the chimeric GAP protein by that cell. Two DNA sequences (such as a promoter region sequence and a desired chimeric protein molecule encoding sequence) are said to be operably linked if the nature of the linkage between the two DNA sequences does not (1) result in the introduction of a frame-shift mutation, (2) interfere with the ability of the promoter region sequence to direct the transcription of the desired chimeric protein molecule encoding gene sequence, or (3) interfere with the ability of the desired chimeric protein molecule gene sequence to be transcribed by the promoter region sequence.

A DNA sequence encoding the chimeric protein molecule may be recombined with vector DNA in accordance with conventional techniques, including blunt-ended or staggerended termini for ligation, digestion to provide appropriate termini, filling in of cohesive ends as appropriate, alkaline phosphatase treatment to avoid undesirable joining, and ligation with appropriate ligases.

Expression vectors for these cells can include expression control sequences, such as an origin of replication, a promoter, an enhancer and necessary processing information sites, such as ribosome-binding sites, RNA splice sites, polyadenylation sites, and transcriptional terminator sequences. Preferably, the enhancers or promoters will be those previously shown to be effective in the host cells of interest, although it will be understood that in many cases others will be equally or more appropriate.

Mammalian expression vectors for use herein will include a promoter capable of directing the transcription of a cloned gene or cDNA. Preferred promoters include viral promoters and cellular promoters. Preferred viral promoters include the major late promoter from adenovirus 2 (Kaufman and Sharp, Mol. Cell. Biol. 2: 1304-13199, 1982) and the SV40 promoter (Subramani et al., Mol. Cell. Biol. 1: 854-864, 1981). Preferred cellular promoters include the mouse metallothionein 1 promoter (Palmiter et al., Science 222: 809-814, 1983) and a mouse V kappa promoter (Grant et al., Nuc. Acids Res. 15: 5496, 1987). A particularly preferred promoter is a mouse VH promoter (Loh et al., ibid.). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 EIB region and the human growth hormone gene terminator (DeNoto et al., Nuc. Acids Res. 9: 3719-3730, 1981). A particularly preferred polyadenylation signal is the VH gene terminator (Loh et al., ibid.). The expression vectors may include a noncoding viral leader sequence, such as the adenovirus 2 tripartite leader, located between the promoter and the RNA splice sites. Preferred vectors may also include enhancer sequences, such as the SV40 enhancer and the mouse enhancer (Gillies, *Cell* 33: 717-728, 1983). Expression vectors may also include sequences encoding the adenovirus VA RNAs.

In general, plasmid vectors containing replication and control sequences, that are compatible with the recombinant host cells, are used as cloning vectors for the DNA molecules. A DNA sequence encoding the chimeric proteins may be inserted into a suitable eucaryotic expression vector, that in turn is used to transfect eucaryotic cells. A eucaryotic expression vector, as used herein, is meant to indicate a DNA construct containing elements that direct the transcription and translation of DNA sequences encoding chimeric proteins of interest. Such elements include promoters, enhancers, transcription terminators and polyadenylation signals. By virtue of the inclusion of these elements operably linked within the DNA constructs, the resulting eucaryotic expression vectors contain the information necessary for expression of the polypeptides of interest.

For a mammalian host, several possible vector systems are available for expression of the desired chimeric protein molecule. One class of vectors utilizes DNA elements that provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells that have stably integrated the introduced DNA into their chromosomes may be selected by also introducing one or more markers that allow selection of host cells that contain the expression vector. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals.

Retroviral vectors have been demonstrated to be particularly useful for delivery of the RhoGAP chimeras. Like other cases of retrovirus-based gene transfer approach, the copy number of the introduced RhoGAP-Rho chimeras in the host cells will likely to be important for the efficacy of their application. Although p190-RhoC-C was effective in downregulating the biochemical activity and migration phenotype of RhoC when expressed with the low copy number vector MIEG3, we have found that expression of p190-RhoA-C or p190-RhoB-C with MIEG3 is insufficient for downregulating the biochemical activity or transforming activity of RhoA-F30L or RhoB-F30L. However, expression of p190-RhoA-C with the high copy number retroviral vector, SF91-EMCV-IRES-GFP, that has been in use for gene therapy trials, can specifically decrease both the biochemical activity of F30LRhoA and the RhoA-F30L-induced transformation under conditions in which p190-RhoB-C, p190-RhoC-C or p190 alone expressed by using the same vector did not affect RhoA-F30L activity nor the RhoA-F30L-induced transformation. These results highlight the importance of dose-dependence in effectiveness and specificity when applying this method to future animal and human trials.

Such expression vectors may also contain a set of RNA splice sites located downstream from the promoter and upstream from the DNA sequence encoding the polypeptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., Nuc. Acids Res. 9:3719-3730, 1981). The expression vectors may include a noncoding viral leader sequence, such as the AdenoVirus 2 tripartite leader, located between the promoter and the RNA splice sites. Vectors may also include enhancer sequences, such as the SV40 enhancer and the mouse mu enhancer (Gillies, Cell 33: 717-728, 1983). Expression vectors may also include sequences encoding the adenovirus VA RNAs.

Once the vector or DNA sequence containing the constructs has been prepared for expression, the DNA constructs may be introduced into an appropriate host. Various techniques may be employed, such as calcium phosphate precipitated DNA transformation, electroporation, protoplast fusion, biolistics, using DNA-coated particles, transfection, and infection, where the chimeric construct is introduced into an appropriate virus, particularly a non-replicative form of the virus, or the like. After the fusion, the cells are grown in media and screened for appropriate activities. Expression of the sequence results in the production of the chimeric GAP protein.

In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. A particularly preferred amplifiable marker is the DHFRr cDNA (Simonsen and Levinson, Proc. Natl. Acad. Sci. USA 80: 2495-2499, 1983). Selectable markers are reviewed by Thilly (Mammalian Cell Technology, Butterworth Publishers, Stoneham, Mass.) and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (See, e.g., Levinson and Simonsen, U.S. Pat. No. 4,713,339). It may also be advantageous to add additional DNA, known as "carrier DNA" to the mixture that is introduced into the cells.

In one embodiment, a vector is employed that is capable of integrating the desired gene sequences into the host cell chromosome. Cells that have stably integrated the introduced DNA into their chromosomes can be selected by also introducing one or more markers that allow for selection of host cells that contain the expression vector. The marker may complement an auxotrophy in the host, biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells that do not contain the vector; the number of copies of the vector that are desired in a particular host; and whether it is desirable to be able to "shuttle" the vector between host cells of different species.

Once one has established that the transformed host is capable of expressing the chimeric protein as a cytoplasmic or surface membrane protein in accordance with the desired regulation and at a desired level, one may then determine whether the protein is functional in the host to provide for the desired signal induction. Since the effect of signal induction of the particular cytoplasmic domain will be known, one may use established methodology for determining induction to verify the functional capability of the chimeric protein. Of course, it is important to know that ancillary signals are not required from other proteins in conjunction with the particular cytoplasmic domain, so that the failure to provide transduction of the signal may be attributed solely to the inoperability of the chimeric protein in the particular target host.

If the cells are transfected in vitro, the transfected mammalian cells are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable selectable marker, the drug concentration may be increased in a stepwise manner to select for increased copy number of the cloned sequences, thereby increasing expression levels.

Host cells containing DNA constructs are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will generally select for cells containing the DNA construct by, for example, drug selection or deficiency in an essential nutrient in which the cells are complemented by the selectable marker on the DNA construct or co-transfected with the DNA construct. The pH of the medium is preferably maintained at a pH greater than about 2 and less than about 8, including but not limited to a pH of 2.5, 3, 3.5, 4, 4.5, 5, 5.5, 6, 6.5, 7, 7.5 and 7.8. Methods for maintaining a stable pH include buffering and constant pH control, preferably through the addition of sodium hydroxide. Preferred buffering agents include succinic acid and Bis-Tris (Sigma Chemical Co., St. Louis, Mo.). Cultured mammalian cells are generally grown in commercially available serum-containing or serum-free media. Selection of a medium appropriate for the particular cell line used is within the level of ordinary skill in the art.

Any peptide disclosed herein can be used in the form of a pharmaceutically acceptable salt. Suitable acids that are capable of forming salts with the peptides include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the subject peptides include inorganic bases such as sodium hydroxide, ammonium hydroxide, potassium hydroxide and the like; and organic bases such as mono-, di- and tri-alkyl amines (e.g., triethyl amine, diisopropyl amine, methyl amine, dimethyl amine and the like) and optionally substituted ethanolamines (e.g. ethanolamine, diethanolamine and the like).

In determining the therapeutically effective amount or dose, the effective GTPase modulating amount or dose of a chimeric GAP peptide, derivative or fragment thereof, a number of factors are considered by the attending diagnostician, including, but not limited to: the species of the mammal; its size, age, and general health; the response of the individual patient; the particular compound administered; the mode of administration; the bioavailability characteristics of the preparation administered; the dose regimen selected; the use of concomitant medication; and other relevant circumstances.

The chimeric GAP proteins can be incorporated into pharmaceutical compositions and administered to a subject in vivo. Use of chimeric GAP proteins can be useful therapeutically for the treatment of disorders caused by, for example, (i) aberrant modification or mutation of a gene encoding a GAP protein; (ii) mis-regulation of the GAP gene; and (iii) aberrant post-translational modification of a GAP protein.

The chimeric GAP nucleic acid molecules and chimeric GAP proteins (also referred to herein as "active compounds") can be incorporated into pharmaceutical compositions suitable for administration. Such compositions typically comprise the nucleic acid molecule, protein, or other active agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or derivative can include a single treatment or, preferably, can include a series of treatments.

The nucleic acid molecules disclosed herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

However, it is understood that the present invention is not limited by any particular theory or proposed mechanism to explain its effectiveness in an end-use application.

In effecting treatment of a patient, a chimeric GAP peptide, derivative, analog, homolog, fragment and mixtures thereof can be administered in any form or mode, that makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the relevant circumstances.

A chimeric GAP peptide, derivative, analog, homolog, fragment and mixtures thereof can be administered in the form of pharmaceutical compositions or medicaments that are made by combining a chimeric GAP peptide, derivative, analog, homolog, fragment and mixtures thereof with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient can be a solid, semi-solid, or liquid material, that can serve as a vehicle or medium for the active ingredient. Suitable carriers or excipients are well known in the art. The pharmaceutical composition can be adapted for oral or parenteral use and can be administered to the patient in the form of tablets, capsules, suppositories, solution, suspensions, or the like.

The pharmaceutical compositions can be administered orally, for example, with an inert diluent or with an edible carrier. They can be enclosed in gelatin capsules or compressed into tablets. For the purpose of oral therapeutic administration, a chimeric GAP peptide, derivative or fragment thereof can be incorporated with excipients and used in the form of tablets, troches, capsules, elixirs, suspensions, syrups, wafers, chewing gums and the like. These preparations should contain at least 4% of a chimeric GAP peptide, derivative or fragment thereof the active ingredient, but can be varied depending upon the particular form and can conveniently be between 4% to about 70% of the weight of the unit. The amount of the active ingredient present in compositions is such that a unit dosage form suitable for administration will be obtained.

The tablets, pills, capsules, troches and the like can also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin can be added or flavoring agents, such as peppermint, methyl salicylate or orange flavoring. When the dosage unit form is a capsule, it can contain, in addition to materials of the above type, a liquid carrier such as polyethylene glycol or a fatty oil. Other dosage unit forms can contain other various materials that modify the physical form of the dosage unit, for example, as coatings. Thus, tablets or pills can be coated with sugar, shellac, or other enteric coating agents. A syrup can contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a chimeric GAP peptide, derivative, analog, homolog, fragment or mixtures thereof can be incorporated into a solution or suspension. These preparations should contain at least 0.1% of a compound disclosed herein, but can be varied to be between 0.1 and about 50% of the weight thereof. The amount of the active ingredient present in such compositions is such that a suitable dosage will be obtained.

When administered intravenously, the peptide compositions can be combined with other ingredients, such as carriers and/or adjuvants. The peptide can also be covalently attached to a protein carrier, such as albumin, so as to minimize clearing of the peptides. There are no limitations on the nature of the other ingredients, except that they must be pharmaceutically acceptable, efficacious for their intended administration and cannot degrade the activity of the active ingredients of the compositions. The peptide compositions can also be impregnated into transdermal patches or contained in subcutaneous inserts, preferably in a liquid or semi-liquid form in which the patch or insert time releases therapeutically effective amounts of one or more of the subject peptides.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutanol, phenol, sorbic acid or thimerosal. Further, isotonic agents such as sugars or sodium chloride can be incorporated in the subject compositions.

Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The solutions or suspensions can also include one or more of the following adjuvants depending on the solubility and other properties of a chimeric GAP peptide, derivative or fragment thereof: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose.

The parenteral preparation can be enclosed in ampules, disposable syringes or multiple dose vials made of glass or plastic.

The pharmacological composition will preferably comprise a chimeric GAP peptide or derivative or fragment thereof along with a pharmaceutically acceptable carrier, fillers or excipients. The administering step can comprise administering a pharmacological composition comprising a chimeric GAP peptide, derivative or fragment thereof along with pharmaceutically acceptable carrier, fillers or excipients.

The methods can be by oral administration of the GTPase modulating composition or a pharmaceutically acceptable salt or derivative thereof into said mammal. The methods also allow the administration of the chimeric molecule is administered in a unitary dose of from about 1 to about 1000 mg. A unitary dose is generally administered from about 1 to about 3 times a day.

The administering step can comprise parenteral administration of the chimeric compound or a pharmaceutically acceptable salt or derivative thereof into said mammal. This administration can be by transdermal administration, subcutaneous injection, intravenous injection, intraperitoneal injection, intramuscular injection, intrasternal injection, intrathecal injection, intracerebroventricular injection and infusion techniques.

The method of also comprises administering chimeric compound or a pharmaceutically acceptable salt or derivative thereof along with a lipophilic compound, such as a lipophilic solvent or carrier. The lipophilic solvent or carrier can be an organic solvent, phosphatidyl choline and cholesterol.

The pharmaceutical compositions can be formulated for the oral, sublingual, subcutaneous, intravenous, transdermic or rectal administrations in dosage units and in admixture with pharmaceutical excipients or vehicles. Convenient dosage forms include, among those for oral administration, tablets, powders, granulates, and, among those for parenteral administration, solutions especially for transdermal administration, subcutaneous injection, intravenous injection, intraperitoneal injection, intramuscular injection, intrasternal injection, intrathecal injection and infusion techniques.

The dosage can vary widely as a function of the age, weight and state of health of the patient, the nature and the severity of the ailment, as well as of the administration route. These doses can naturally be adjusted for each patient according to the results observed and the blood analyses previously carried out.

Various methods and compositions are disclosed in the following United States Provisional applications which are incorporated by reference in their entirety: 60/527,589 (Methods of Enhancing Stem Cell Engraftment), filed Dec. 5, 2003, 60/494,718 (Mobilization of Hematopoietic Cells), filed Aug. 13, 2003, and 60/523,599 (GTPase inhibitors and Methods of Use), filed Nov. 20, 2003.

EXAMPLES

Embodiments of the chimeric or fusion polypeptides will now be described with reference to the following examples. The methods that are provided are used in all of the examples unless a variation or alternative method is set out.

Example 1

Distinct Roles of RhoA, RhoB and RhoC in Cell Transformation and Migration

Among the three closely related Rho proteins, RhoA, RhoB and RhoC, RhoA is the best characterized one and has been shown to regulate actin stress fiber and focal complex formation, to promote cell growth and to transform NIH 3T3 fibroblasts. By contrast, the function of RhoB or RhoC in fibroblasts has not been examined in detail and has not been directly compared with that of RhoA. To make comparisons of the cellular roles of RhoA, RhoB and RhoC, two sets of activating mutants were generated for each of the Rho proteins: the fast-cycling Rho-F30L and the GTPase-defective Rho-Q63L. Both types of mutants result in the net enhancement of the active Rho-GTP species in cells but involved distinct mechanisms: Rho-F30L proteins contained significantly increased intrinsic GDP/GTP exchange activity and remained responsive to RhoGAP stimulation to cycle between the GDP- and GTP-bound states, while the Rho-Q63L mutants could not hydrolyze bound GTP and were locked into the GTP-bound active conformation. These mutants were introduced into NIH 3T3 cells and generated mutant-expressing stable clones. Western blots showed that the two mutant forms of all three Rho GTPases expressed well in the cells.

Staining of the cells with fluorescently labeled phalloidin or anti-vinculin antibody revealed that under serum-free conditions, both active forms of RhoB and RhoC stimulated the actin stress fiber and focal adhesion plaque formation, effects similar to that induced by the active RhoA mutants or by 10% CS stimulation. Since the amino acid sequences of the three Rho proteins are over 85% identical overall and are almost 100% identical in the switch I effector domain, it is likely that they utilize the same set of effector targets to mediate actin structural changes and focal adhesion assembly.

Although RhoB has been suggested to be involved in Ras-mediated oncogenic transformation, RhoA is the only one among the three that has been shown to possess transforming activity. When the transformation ability of the RhoA, RhoB and RhoC mutants were directly compared in a foci forming assay, RhoB displayed a potent transforming activity similar to RhoA in both RhoB-F30L and RhoB-Q63L forms. In contrast, neither active forms of RhoC were able to transform cells. RhoA was previously shown to be involved in fibroblast cell movement by mediating cell body contraction. When the migration rates of the cells expressing the active mutants of RhoA, RhoB or RhoC were compared in a wound healing assay, RhoC, but not RhoA or RhoB, was able to significantly increase migration of the cells from the edge of the wound to the open space in the middle of the wound. These results indicate that individual Rho proteins have unique functions in the two aspects related to tumorigenesis—transformation and migration. RhoA, in particular, is important for cell growth control and transformation, while RhoC might be a key player in mediating cell movement. Although RhoB is capable of transforming cells under the overexpression conditions, it can serve as a sensor for DNA damage signals and mediate apoptotic responses of the cells based on the genetic evidence. The functional differences of these Rho proteins might be attributed to the sequence divergence in their C-terminal hypervariable region, an area that is known to be involved in their distinct intracellular distribution.

The Rho Mutants were Produced Using Site-Directed Mutagenesis as Follows:

Site-directed mutants of human RhoA, RhoB and RhoC were generated by polymerase chain reactions using the Pfu polymerase, with primers that contained the desired mutations following the published protocols (Li, et al. 1997, J. Biol. Chem. 272, 32830-5, herein incorporated by reference in its entirety). The mutant cDNAs were subcloned into the BamHI and EcoRI sites of mammalian expression vector pCEFL-GST and the mutants were expressed as glutathione S-transferase (GST) fusions (Vanni, et al. 2002, J. Biol. Chem. 277, 19745-19753, herein incorporated by reference in its entirety). The sequences of mutagenized DNA inserts were confirmed by automated sequencing. All point mutants used are described by single-letter amino acid denominations.

Cell Culture and Transfection.

NIH 3T3 cells were cultured in DMEM supplemented with 10% calf serum (CS) in a 5% $CO_2$ incubator at 37° C. Cos-7 cells and the retroviral packaging *Phoenix* cells were cultured in DMEM with 10% fetal bovine serum (FBS). The A375 and HME tumor cell lines were maintained as described (8; 8; 9). To generate stable transfectants, NIH 3T3 cells were seeded in 6-well plate at a density of $1.5 \times 10^5$ cells in DMEM medium supplemented with 10% CS. These cells were transfected with the pCEFL-GST-Rho constructs in the next day using LipofectAMINE Plus (Life Technologies) following the manufacturer's instructions. Selection of stable transfectants was carried out by adding 0.35 mg/ml of G418 to the culture medium 48 hr after transfection. After ~2 weeks culturing in the selection medium, the surviving cell clones were examined for the expression of GST fusion proteins by anti-GST immunoblotting.

Transformation Assay.

Measurements of the anchorage independent growth of mutant Rho protein-expressing cells or tumor cells were carried out as described (38, 39). Briefly, $2 \times 10^4$ cells were suspended in the 10% FBS-supplemented Ham's F-12 complete medium with growth factors and 0.3% agarose and were plated on top of a solidified, 0.6% agarose. The cells were fed weekly by the addition of 1 ml of medium. Three weeks after plating, the colonies grown larger than 50 µm in diameter were scored under a microscope. To measure cell transforming activity, 5×10³ cells transfected with various Rho constructs were mixed with 5×10⁴ wild type NIH 3T3 cells and were plated in 100-mm dishes in a medium containing DMEM supplemented with 10% CS. The cells were fed every other day, and the visible foci were scored 14 days post-plating.

Wound Healing and Migration Assays.

For wound healing assays, cells were plated at 2×10⁶/dish density in 60-mm diameter dishes. A plastic pipette tip was drawn across the center of the plate to produce a clean 1-mm-wide wound area after the cells have reached confluency. After a 12 hr culturing in DMEM supplemented with 0.5% CS, cell movement into the wound area was examined at different time points using a phase-contrast microscope. The distances between the leading edge of the migrating cells and the edge of the wound were compared (Guo, et al. J. Biol. Chem. 2003, in press).

Cell migration was also measured by using a Transwell plate inserted with a 6.5-mm polycarbonate membrane (8.0-μm pore size, Costar Corporation). Briefly, 5×10⁴ cells were suspended in 0.2 ml of culture medium and were added to the upper chamber. 10% FBS in culture medium was used as chemoattractant in the lower chamber. The cells were incubated for 16 hr in a humidified $CO_2$ incubator at 37° C. The cells that traversed the 8.0-μm membrane pores and spread to the lower surface of the membrane were stained with 5% Giemsa solution and the cells retained in the membrane were counted in at least 6 different fields. Each experiment was carried out in triplicate, and the error bars represent the mean standard error.

Invasion Assay.

Cell invasion assays were performed using the 6.4-mm Biocoat Matrigel invasion chambers equipped with the 8.0-μm pore sized PET membrane filters (Becton-Dickinson) according to the manufactory's instructions. Briefly, 2.5×10⁴ cells were suspended in 0.5 ml of culture medium and were added to the upper chamber. 10% FBS in the culture medium was plated in the lower chamber as chemo-attractant. Cells in the invasion chambers were incubated in a humidified incubator. The cells that traversed the Matrigel matrix and the 8-μm membrane pores and spread to the lower surface of the filters were stained with 5% Giemsa solution for visualization. Each data point of the invasion test was derived from triplicate chambers, and error bars represent the mean standard error.

Example 2

Targeting Individual Rho GTPase Activities by p190-Rho Chimeras

The commonly used biochemical tools to implicate the involvement of a Rho protein in a particular signaling pathway include the dominant negative mutant of the Rho protein and certain bacterial toxins that can modify the Rho protein function. These reagents are limited by their non-specific nature in interfering with Rho GTPase functions (Geig, et al. 1999, Nat. Cell. Biol. 1, E25-E27, herein incorporated by reference in its entirety) and can have limited therapeutic value in targeting specific Rho proteins. In order to specifically inhibit individual Rho protein function, we hypothesize that the negative regulatory role of RhoGAPs, the RhoGAP domain in particular, could be exploited to downregulate Rho protein activity if it is directed to where the active Rho GTPase substrates reside in cells. The RhoGAP domain of p190 has previously been demonstrated as a catalyst to specifically stimulate GTP-hydrolysis of Rho, not Rac or Cdc42, but it cannot distinguish among the RhoA, RhoB and RhoC subtypes (Zhang, et al. 1998 Biochemistry 37, 5249-5257, and Settleman, et al. 1992, Cell 69, 539-49, both of which are herein incorporated by reference int their entirety). When introduced into cells by microinjection, it is mostly cytosolic and readily disassembled the actin stress fiber structure (Ridley, et al. 1993, EMBO J. 12, 5151-60). In cells the RhoGAP domain is likely to be tightly regulated by other structural motifs in full-length p190 and both of its catalytic activity and intracellular location can be altered by phosphorylation and protein-protein interaction in response to extracellular stimuli (Prendergast, et al. 2001 Nature Review Cancer 1, 162-168, Feig, et al. 1999, Nat. Cell Biol. 1, E25-E27, and Wang, et al. 1997 Cancer Res. 57, 2478-2484, all of which are herein incorporated by reference in their entirety). On the other hand, the C-terminal polybasic hypervariable region of Rho proteins, including the CAAX isoprenylation motif, appears to determine the subcellular distribution of respective Rho GTPases (Yoshioka, et al. 1998, J. Biol. Chem., 273, 5146-5154, herein incorporated by reference in its entirety). It seemed therefore logical that by fusing the RhoGAP domain with the C-terminal region of individual Rho protein we would provide the catalytic, GTP-hydrolyzing domain with a specific Rho targeting signal. When expressed at a low level in a controlled manner, such a GAP-Rho chimera might constitute an effective and specific inhibitor of individual Rho activity. Thus, we have generated a set of p190 GAP domain and the C-terminus of RhoA, RhoB or RhoC chimeric constructs to test this hypothesis.

The p190-Rho chimeric cDNAs were generated by fusing the cDNAs encoding the RhoGAP domain of rat p190 and the cDNAs encoding the C-terminus of human RhoA, RhoB, or RhoC after PCR amplification of the respective sequences. The primer sequences for RhoA C-terminus are 5' GCGAAT-TCTCACAAGACAAGGCAACCA-GATTTTTCTTCCCACGTCTAGCTTG C AGAGAAGA-CAACTGATTTTCCTGC 3' (SEQ ID NO:26), for RhoB C-terminus are 5' GCGAATTCTCATAGCACCTTGCAG-CAGTTGATGCAGCCGTTCTGGGAGCCGTA GCTTCT-GCAGAGAAGACAACTGATTTTCCTGC 3' (SEQ ID NO:27), and for RhoC C-terminus are 5' GCGAATTCTCA-GAGAATGGGACAGCCCCTCCGACGCT-TGTTCTTGCGGACCTG GAGAGAAGACAACT-GATTTTCCTGC 3' (SEQ ID NO:28). The ligation products of cDNAs encoding p190RhoGAP domain and the respective Rho sequences were cloned into the MIEG3-(HA)₃ retroviral vector that expresses the chimeras as (HA)₃-fusions together with the enhanced green fluorescent protein (EGFP) bicistronically (Jordan, et al. 1999, Oncogene 18, 6835-6839, herein incorporate by reference in its entirety) as well as the pCEFL-GST vector for transient expression in mammalian cells.

Example 3

Comparison of GAP Activities of Fusion Proteins In Vitro

To ensure that the C-terminal sequences of various Rho proteins fused to the GAP domain of p190 do not interfere with the GAP function of p190, we expressed the GST-tagged p190 and p190-Rho chimeras in Cos-7 cells, purified them by glutathione-agarose affinity beads and compared their GAP activities in vitro. Under similar doses, p190-RhoA-C, p190-RhoB-C and p190-RhoC-C displayed comparable GAP activities as p190 GAP domain alone on the RhoA substrate to stimulate [$\gamma^{32}$P]GTP-hydrolysis in a time dependent manner, indicating that all four p190 and p190-Rho chimera proteins are functional. To evaluate the efficacy and specificity of the chimeric constructs in cells, we employed the above described fast-cycling mutant Rho-F30L and GTPase-defective mutant Rho-Q63L expressing cells as testing systems, taking advantage of the facts that the F30L mutant form of the Rho GTPases is fully responsive to GAP stimulation while the GTPase-defective Rho-Q61L mutants would not be affected by the RhoGAP treatment, but both mutant forms behave similarly in eliciting cellular effects such as induction of transformation or migration. We chose the retroviral MIEG3 expression vector for delivery of the constructs because it allows stable introduction of a single copy of gene of interests into a host cell and contains a bicistronically expressed EGFP as a marker that permits quick and semi-quantitative isolation of the p190 expressing cells base on the EGFP fluorescence (Gu, et al, 2001, J. Biol. Chem. 276, 15929-15938, and Yang, et al. 2001, PNAS, USA, 98, 5614-5618, both of which are herein incorporated by reference in their entirety). When the FACS purified EGFP positive cells were examined for the expression of HA-tagged p190-Rho chimeras by Western blotting, all constructs were found to be expressed at a similar level.

GTPase Activity Assay.

The intrinsic and p190GAP-stimulated GTPase activities of RhoA were measured as described (Li, et al, 1997, *J. Biol. Chem.* 272, 32830-5, herein incorporated by reference in its entirety) by the nitrocellulose filter-binding method. Briefly, recombinant RhoA were preloaded with [$\gamma$-$^{32}$P]GTP (10 $\mu$Ci, 6000Ci/mmol, NEN) in a 100 $\mu$l buffer containing 50 mM HEPES, pH 7.6, 0.2 mg/ml BSA, and 0.5 mM EDTA for 10 min at ambient temperature before the addition of MgCl$_2$ to a final concentration of 5 mM. An aliquot of the [$\gamma$-$^{32}$P]GTP-loaded RhoA was mixed with GAP assay buffer containing 50 mM HEPES, pH 7.6, 100 mM NaCl, 0.2 mg/ml BSA, and 5 mM MgCl$_2$ in the presence or absence of various GAPs. At different time points the reaction was terminated by filtering the reaction mixture through nitrocellulose filters. The radioactivity retained on the filters were then subjected to quantitation by scintillation counting.

Retroviral Gene Transfer.

Various p190-Rho chimeras were expressed in NIH 3T3 cells or tumor cells by the retroviral infection method. Production of recombinant retrovirus in the retroviral packaging *Phoenix* cells and subsequent host cell infection were carried out according to the described protocols (Suwa, et al. 1998, Br. J. Cancer 77, 147-152, herein incorporated by reference in its entirety. The infected cells were harvested 72 hr post infection. EGFP-positive cells (typically 10%~50%) were isolated by fluorescence activated cell sorting (FACS) and were used for further analysis.

Example 4

Specificity of Cellular Localization by C-Terminal Sequences

To determine if the C-terminal sequences of Rho proteins in the chimeras could indeed dictate intracellular localization of the fused p190 GAP domain, the localization patterns of p190-RhoA-C, p190-RhoB-C and p190-RhoC-C were examined by immunofluorescence and comparisons were made with those of the respective Rho-F30L proteins expressed in these cells. p190-RhoA-C was found mostly in the cytosol with a small proportion localized at the plasma membrane. This is similar to that of the GST-F30LRhoA distribution pattern revealed by anti-GST immunostaining. p190-RhoB-C was found in the intracellular vesicles reminiscent of endosomes, similar to the RhoB-F30L locations. Likewise, p190-RhoC-C displayed a similar localization pattern to RhoC-F30L with a uniquely diffused but punctuated pattern. These results suggest that the different C-terminal sequences of the Rho proteins can direct the p190-Rho chimeras to distinct locations similar to the Rho GTPases themselves.

Immunofluorescence—

Cells grown on coverglasses were fixed with 3.7% formaldehyde in phosphate buffered saline (PBS) for 15 min and washed with PBS once followed by permeablization with 0.1% Triton X-100 for 20 min. The cells were then blocked with 2% bovine serum albumin (BSA) for 20 min. For actin staining, the cells were incubated with rhodamine-phalloidin. For vinculin staining, the cells were labeled with anti-vinculin monoclonal antibody (Sigma, Inc.) followed by incubation with a rhodamine-conjugated goat anti-mouse secondary antibody. To determine the intracellular localization of various Rho proteins or p190-Rho chimeras, the FACS isolated, EGFP positive cells were labeled either with anti-HA monoclonal antibody or with anti-GST polyclonal antibody followed by rhodamine-conjugated secondary antibody staining. The stained cells were mounted onto slides in Aquamount and viewed with a Zeiss LSM510 confocal microscopy or a Leica fluorescence microscopy equipped with the deconvolution software (Improvision, Inc.).

Example 5

Can Chimeras Specifically Target Rho GTPase Activities In Vitro

To examine whether the p190-Rho chimeras can be used to specifically target individual Rho GTPase activities, the GTP-bound form of RhoC-F30L in cells co-expressing RhoC-F30L and p190, p190-RhoA-C, p190-RhoB-C or p190-RhoC-C were probed by affinity precipitation with immobilized His-Rhotekin. p190-RhoC-C, but not p190, p190-RhoA-C nor p190-RhoB-C, specifically downregulated the RhoC-F30L activity. Moreover, in cells expressing the GTPase-defective form of RhoC, RhoC-Q63L, p190-RhoC-C did not affect the amount of RhoC-Q63L-GTP precipitated from the cell lysates by Rhotekin. Thus, the p190-Rho chimeras, p190-RhoC-C in particular, can specifically downregulate individual Rho protein activities depending on the C-terminal sequences of the Rho protein fused to the RhoGAP domain.

Rho Effector Pull-Down Assay.

To determine the RhoA, RhoB, or RhoC activity in cells, the effector pull-down assay (Zhu, et al., 2000 *J. Biol. Chem.* 275, 25993-26001, herein incorporated by reference in its entirety) was carried out in the respective cells that have been serum-starved for 20 hours. The effector probe for Rho-GTP, recombinant (His)$_6$-Rhotekin, was expressed and purified from *E. coli* and immobilized on the Ni-NTA-agarose beads. The beads-associated (His)$_6$-Rhotekin (about 1 $\mu$g/sample) was incubated with the respective cell lysates expressing various GST-Rho proteins for 45 minutes at 4° C. and the co-precipitates were analyzed by Western blotting with anti-GST monoclonal antibody.

Example 6

Migration Phenotype of Cells Transfected with Chimeras

To demonstrate the functional outcome of p190-Rho chimera application, the migration phenotype caused by expression of RhoC-F30L was examined in cells co-expressing RhoC-F30L and various chimeras. FIG. 6 shows that the RhoC-F30L-stimulated cell migration can be specifically reverted by p190-RhoC-C, but not by the vector control, p190GAP, p190-RhoA-C or p190-RhoB-C. In contrast, p190-RhoC-C, as well as the other chimeras, had no effect on the RhoC-Q63L induced cell migration. These results further suggest that the p190-Rho chimeras are useful tools to functionally revert cellular phenotypes caused by elevation of individual Rho activity.

Example 7

Reversal of Tumor Cell Transformation and/or Invasion by p190-RhoC-C Chimera To identify whether the p190-Rho chimeras could demonstrate a function outcome, they were applied to human cancer cells that show characteristics of transformation and/or invasion due to overexpression or upregulation of specific Rho GTPase. Previously it was demonstrated that the human mammary epithelial cells (HME) acquired the transformation and invasion activities by overexpression of RhoC, resulting in phenotypes similar to that of inflammatory breast cancer cells (van Golen, et al. 2000 Cancer Res. 60, 5832-8, herein incorporated by reference in its entirety). In the soft-agar based growth assay, very few colonies grew in the control retrovirus-treated HME cells (FIG. 1A). Upon introduction of RhoC, the colony-forming activity of the cells (HME-RhoC) increased dramatically. As shown in FIG. 7A, the colony-forming activity of HME-RhoC cells was inhibited by ~5 fold upon treatment with the retrovirus expressing p190-RhoC-C while it was not affected by the control EGFP expressing virus, or virus expressing p190, p190-RhoA-C or p190-RhoB-C. Moreover, the invasive activity of HME-RhoC was also specifically inhibited by p190-RhoC-C, but not by EGFP alone or by p190, p190-RhoA-C or p190-RhoB-C (FIG. 1B).

Figure 2A:
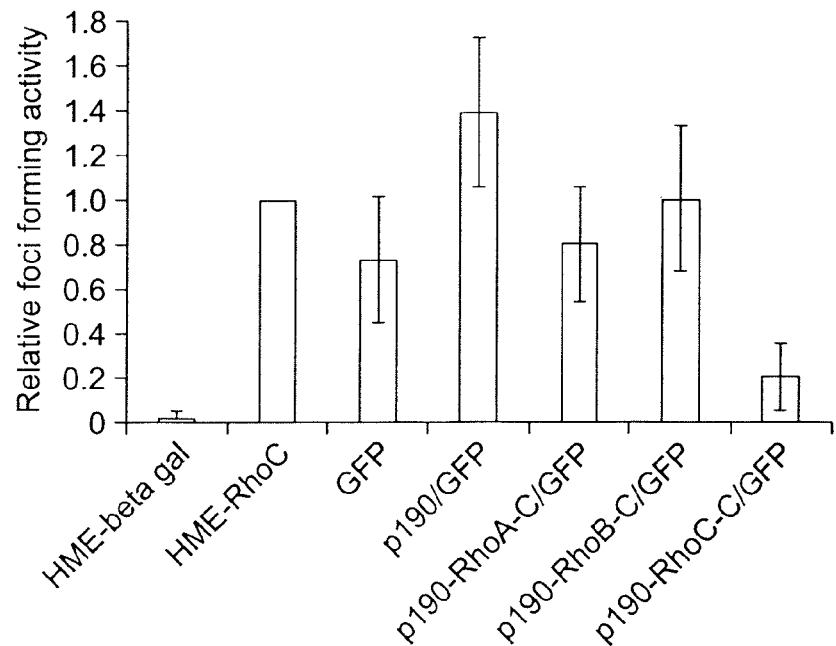
FIG. 2 is a graph showing the effect of p190-RhoC-C on the anchorage independent growth and invasion properties of the human breast cancer cells HME-RhoC. A, the abilities of HME, HME-RhoC, and HME-RhoC transduced with various p190-Rho chimeras with MIEG3 vector to grow on soft agar were compared three weeks after plating the cells on 0.3% of soft agar. B, the invasive activity of the HME-RhoC cells and those transduced with various p190-Rho chimeras were assayed in a Matrigel coated transwell. The cells that succeeded in invasion into the Matrigel were quantified 16 hrs after plating.
Figure 2B:
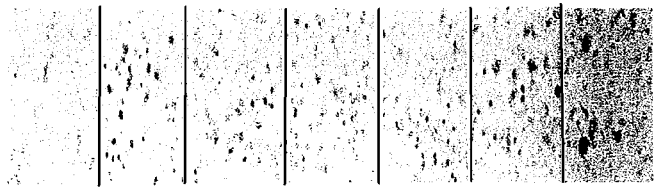
Figure 2B:
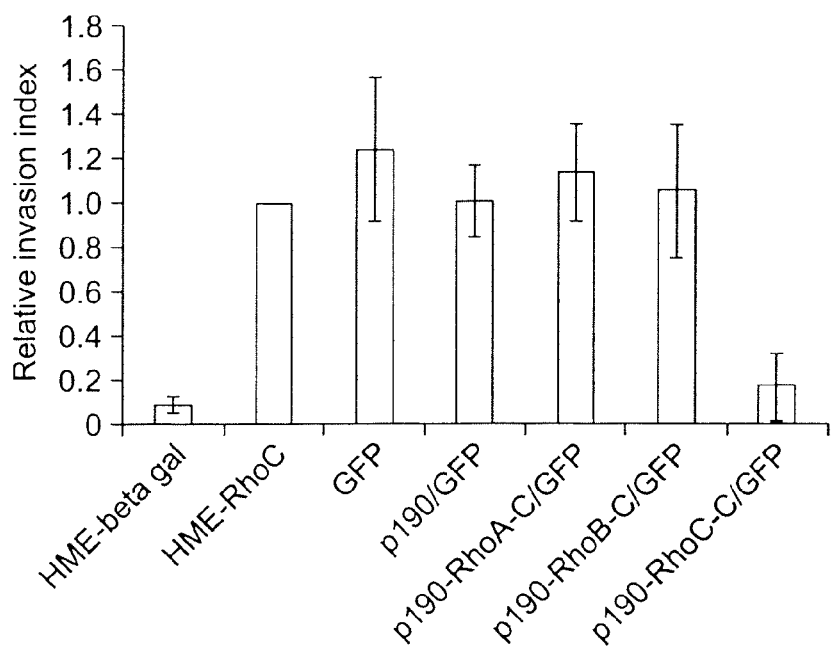
Figure 3:
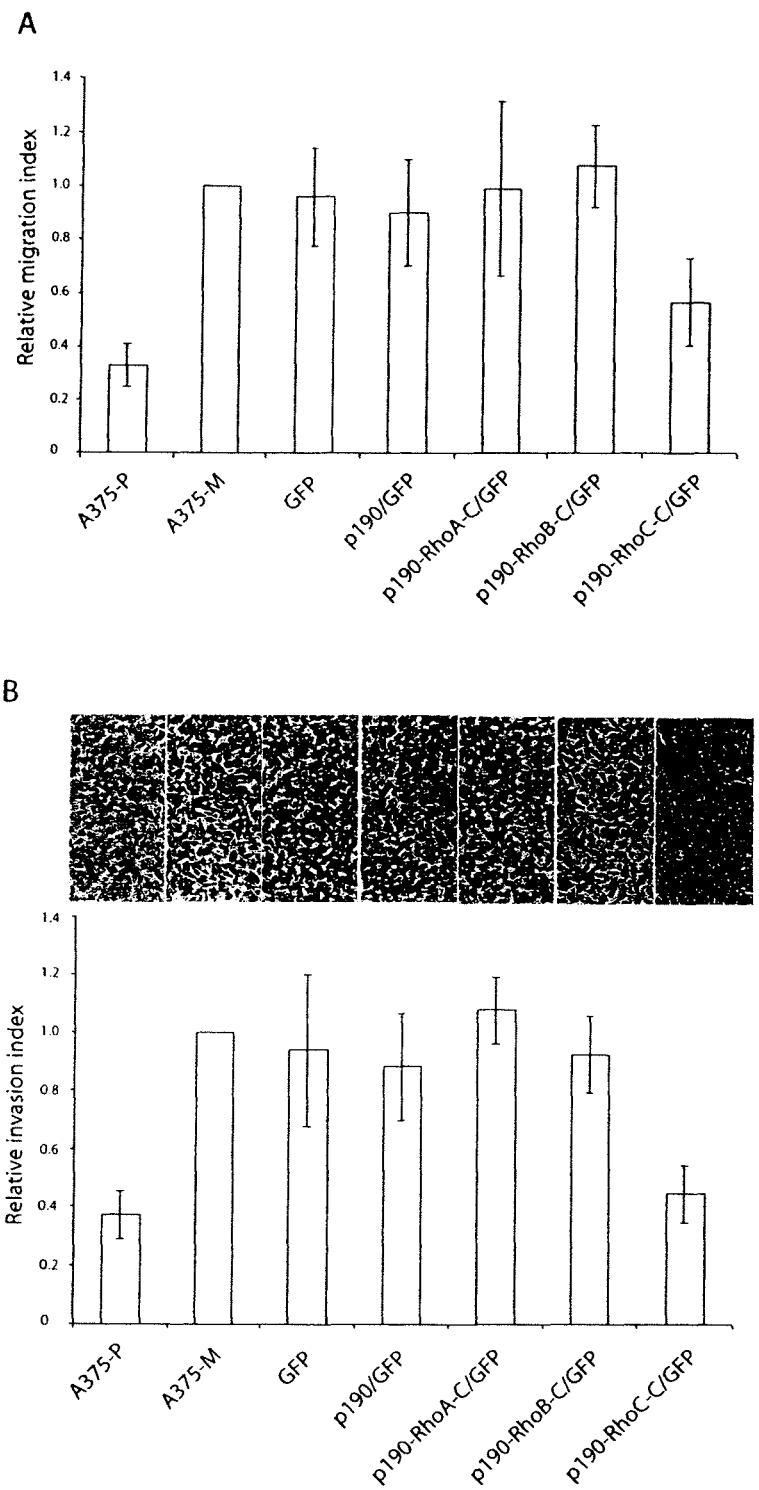
FIG. 3 is a graph showing the p190-RhoC-C chimera was effective in reversing the migration and invasion phenotypes of the metastatic human melanoma A375-M cells. A, the migration ability of the A375 parental cells and the metastatic A375-M cells transduced with the retrovirus encoding the MIEG3 vector alone, p190GAP, or various p190-Rho chimeras was assayed in a transwell. The cells that moved into the pore of the transwell membranes after a 16 hr incubation were quantified. B, the cells were induced to invade the matrigel-coated membranes by 10% FBS in a transwell for 48 hrs. The number of cells invaded into the matrigel was counted. The quantitative results were derived from experiments carried out in triplicates.

In a previous gene array screening, the mRNA level of RhoC was found to be significantly elevated in the highly metastatic human melanoma A375-M cells compared with the non-invasive parental A375 cells (Clark, et al. 2000 *Nature*, 406, 532-5, herein incorporated by reference in its entirety). The invasive and metastatic properties of A375-M were attributed in part to the increased RhoC activity (Clark, et al. 2000 *Nature*, 406, 532-5, herein incorporated by reference in its entirety). When the set of p190-Rho chimeras were applied to the A375-M tumor cells, the p190-RhoC-C chimera was found to significantly reduce both the migration and the invasion activities of A375-M (FIGS. 2A and 2B), similar to the extent caused by forced expression of excess amount of dominant negative RhoA (Clark, et al. 2000 *Nature*, 406, 532-5, herein incorporated by reference in its entirety). Again, p190, p190-RhoA-C or p190-RhoB-C as well as the retrovirus expressed EGFP, had no detectable effect on the migration or invasion property of the tumor cells. Thus, it appears that the p190-Rho chimeras can be applied to human tumor cells to specifically downregulate individual Rho GTPase activities and to reverse the growth and/or invasion phenotypes associated with overexpression of a distinct subtype of Rho GTPase.

These results validify the RhoGAP based approach to specifically downregulate the biochemical and biological activity of individual Rho subtypes in cells. The p190-Rho based method appears to work exceptionally well at the tumor cell level in specifically downregulating the activity of an individual Rho subtype and in reversing the tumor cell phenotypes.

In addition to p190, the GAP domain of Bcr has been shown to be specific for Rac but can not distinguish among Rac1, Rac2 and Rac3 subtypes (Zhang, et al. 1998 *J. Biol. Chem.* 273, 8776-8782, herein incorporated by reference in its entirety), whereas Cdc42GAP favors catalyzing the GTP-hydrolysis of Cdc42 but remains quite active toward other Rho proteins. Like that of RhoA, RhoB and RhoC, the C-terminal sequences of Rac1, 2, 3 and Cdc42, including the lipid modification CAAX motif, have been known to direct their distinct intracellular localization patterns (Michaelson, et al. 2001, J. Cell Biol. 152, 111-26, herein incorporated by reference in its entirety). These RhoGAP based constructs also provide valuable tools for the cell biological studies of individual Rho protein functions that might not have been appreciated previously by the dominant negative mutant approach or the toxin treatment.

Example 8

RhoGTPase Rac2 is Required for In Vivo Transformation Activity by p210 Bcr-Abl Fusion Oncogene Bcr-Abl, the translocation product of the Philadelphia chromosome implicated in human chronic myelogenous leukemia (CML), is a kinase affecting hematopoietic stem cell (HSC) behavior with respect to proliferation, apoptosis, adhesion and migration. Rho GTPases, particularly the Rac subfamily, have been shown to regulate these same cell functions in normal HSC and also regulate gene expression in many mammalian cells. BCR contains a "GTPase-activating protein" domain and a guanine nucleotide exchange domain, the latter or that is preserved in p210 Bcr-Abl. Since HSC functions regulated by Bcr-Abl and Rac are similar, the potential involvement of Rac activation in Bcr-Abl signaling cascade was studied. Human CML samples demonstrate baseline activation of Rac proteins that is reversed by in vitro treatment with ST1571. To study the specific involvement of Rac2, a gene targeted mouse model with Rac2 null bone marrow was used (see Table 1). Using retrovirus-mediated gene transfer, p210 Bcr-Abl was introduced in the MSCV vector into wild-type or Rac2−/− HSC/P and the behavior of these cells was studied in vitro and in vivo.

TABLE 1

| | Gene-targeted mouse model with Rac2 null bone marrow | | | |
|---|---|---|---|---|
| | WILD TYPE | | Rac2$^{-/-}$ | |
| | I. EMPTY VECTOR | MSCV-p210 | Empty vector | MSCV-p210 |
| II. PROLIFERATION (CPM) | | | | |
| Medium | 562 ± 278 | 16,207 ± 1605* | 819.7 ± 363 | 3,135.5 ± 498** |
| SCF (100 ng/ml) | 856 ± 187 | 23,226 ± 2203* | 853.7 ± 524 | 3,756.8 ± 207** |
| Cytokines (SCF, GCSF, MGDF) | 8011 ± 1412 | 42,711 ± 13393* | 4833 ± 1019 | 3,614.5 ± 1982** |
| III. MIGRATION (%) | | | | |
| Fibronectin | 7 ± 0.4 | 38 ± 1.9* | 0.4 ± 0.0 | 0.8 ± 0.1** |
| SDF-1α | 30 ± 2.8 | 13 ± 1.1* | 0.5 ± 0.0 | 0.6 ± 0.0** |
| Adhesion (%) | | | | |
| Fibronectin | 76 ± 2.9 | 40 ± 3* | 4 ± 0.4 | 10 ± 0.1** |

*$p < 0.01$ vs WT-MIEG3,
**$p < 0.01$ vs WT-p210 bcr-abl.

Irradiated recipient mice injected with LDBM cells transduced with p210 developed a uniformly fatal myeloproliferative syndrome (Median survival: 45 days, N=12), while mice injected with p210 transduced Rac2-/- LDBM cells (N=12, 2 independent exp.) had 100% survival and no development of leukocytosis, splenomegaly or organ infiltration of hematopoietic cells. These data suggest that Rac GTPases are involved in the transformation of HSC by Bcr-Abl and provide an additional therapeutic target for intervention in CML.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A chimeric polypeptide, comprising:
a guanosine triphosphatase-activating protein (GAP) activity domain consisting of amino acids 1014 to 1205 of SEQ ID NO: 6 or a fragment thereof having GAP activity; and
at least one targeting domain comprising the amino acid sequence of SEQ ID NO: 19 or a fragment thereof which targets at least one specific guanosine triphosphatase (GTPase) protein.

2. The chimeric polypeptide of claim 1, wherein said targeting domain is a C-terminal sequence from a GTPase.

3. The chimeric polypeptide of claim 1, wherein the chimeric polypeptide further comprises a membrane translocating protein domain or a membrane-translocating peptide.

4. The chimeric polypeptide of claim 1, wherein the chimeric polypeptide further comprises 6-12 amino acids at either end of the chimeric polypeptide.

5. The chimeric polypeptide of claim 1, wherein the chimeric polypeptide comprises the amino acid sequence of SEQ ID NO:12.

6. The chimeric polypeptide of claim 5, the chimeric polypeptide consists of the amino acid sequence of SEQ ID NO: 12.

7. The chimeric polypeptide of claim 1, wherein the targeting domain is N-terminal to the GAP activity domain.

8. The chimeric polypeptide of claim 1, wherein the targeting domain is C-terminal to the GAP activity domain.

9. A composition comprising the chimeric polypeptide according to claim 1 in a pharmaceutically acceptable carrier.

10. The chimeric polypeptide of claim 3, wherein the membrane-translocating peptide comprises a membrane-associating isoprenylation modification.

11. The chimeric polypeptide of claim 3, wherein said membrane translocating protein comprises a lipid-modified peptide.

12. The chimeric peptide of claim 3, wherein said membrane translocating protein is a peptide of about 8 to about 50 residues.

13. The chimeric polypeptide of claim 3, wherein the membrane-translocating peptide is an amino acid sequence having about 8 to about 24 residues comprising at least eight consecutive residues of an amino acid sequence selected from the group consisting of: SEQ ID NO:21, SEQ ID NO:22, SEQ ID NO:23, SEQ ID NO:24, SEQ ID NO:25, and fragments thereof.

14. A method of treating a disease related to up-regulation of GTPase activity in a mammal, comprising administering to the mammal a composition in an amount effective to reduce the GTPase activity,
wherein the composition comprises:
(i) a chimeric polypeptide comprising a guanosine triphosphatase-activating protein (GAP) activity domain consisting of amino acids 1014 to 1205 of SEQ ID NO: 6 or a fragment thereof having GAP activity, and at least one targeting domain comprising the amino acid sequence of SEQ ID NO: 19 or a fragment thereof which targets at least one specific guanosine triphosphatase (GTPase) protein; and
(ii) a pharmaceutically acceptable carrier.

15. A method for modulating GTPase activity in a cell, comprising:
contacting said cell with an active compound that modulates GTPase activity,
wherein the active compound is a chimeric polypeptide comprising a guanosine triphosphatase-activating protein (GAP) activity domain consisting of amino acids 1014 to 1205 of SEQ ID NO: 6 or a fragment thereof having GAP activity; and at least one targeting domain comprising the amino acid sequence of SEQ ID NO: 19 or a fragment thereof which targets at least one specific guanosine triphosphatase (GTPase) protein.

16. A method for the treatment of cancer in a patient, comprising administering a composition to said patient in an amount effective to inhibit GTPase activity,
wherein the composition comprises:
(i) a chimeric polypeptide comprising a guanosine triphosphatase-activating protein (GAP) activity domain consisting of amino acids 1014 to 1205 of SEQ ID NO: 6 or a fragment thereof having GAP activity, and at least one targeting domain comprising the amino acid sequence of SEQ ID NO: 19 or a fragment thereof which targets at least one specific guanosine triphosphatase (GTPase) protein; and
(ii) a pharmaceutically acceptable carrier.

17. The chimeric polypeptide of claim 16, wherein the cancer is selected from the group consisting of: squamous cell cancer, head and neck cancer, and breast cancer.

* * * * *

UNITED STATES PATENT AND TRADEMARK OFFICE
CERTIFICATE OF CORRECTION

PATENT NO.         : 8,674,075 B2                           Page 1 of 1
APPLICATION NO.    : 13/584745
DATED              : March 18, 2014
INVENTOR(S)        : Yi Zheng and David A. Williams It is certified that error appears in the above-identified patent and that said Letters Patent is hereby corrected as shown below:

In the Claims:

In Column 97, line 45, claim 12, delete "The chimeric peptide" and insert -- The chimeric polypeptide --

Signed and Sealed this
Twenty-second Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,674,075 B2
APPLICATION NO.   : 13/584745
DATED             : March 18, 2014
INVENTOR(S)       : Yi Zheng and David A. Williams Page 1 of 1

It is certified that error appears in the above-identified patent and that said Letters Patent is hereby corrected as shown below:

In the Specification

Column 1, after Line 22, please include the following paragraph:
--STATEMENT REGARDING FEDERALLY SPONSORED RESEARCH OR DEVELOPMENT
This invention was made with government support under grant number GM060523 awarded by the National Institutes of Health. The Government has certain rights in the invention.--

Signed and Sealed this
Seventh Day of April, 2020

Andrei Iancu
*Director of the United States Patent and Trademark Office*